(12) United States Patent
Zaborsky

(10) Patent No.: US 12,115,268 B2
(45) Date of Patent: Oct. 15, 2024

(54) DISINFECTING METHODS AND APPARATUS

(71) Applicant: Inikoa Medical, Inc., Newark, CA (US)

(72) Inventor: Brett M. Zaborsky, Newark, CA (US)

(73) Assignee: INIKOA MEDICAL, INC., Newark, CA (US)

( * ) Notice: Subject to any disclaimer, the term of this patent is extended or adjusted under 35 U.S.C. 154(b) by 1130 days.

(21) Appl. No.: 16/887,667

(22) Filed: May 29, 2020

(65) Prior Publication Data
US 2020/0289689 A1 Sep. 17, 2020

Related U.S. Application Data

(63) Continuation of application No. 16/012,182, filed on Jun. 19, 2018, now Pat. No. 10,765,767.

(51) Int. Cl.
*A61L 2/10* (2006.01)
*A61L 2/08* (2006.01)
(Continued)

(52) U.S. Cl.
CPC .............. *A61L 2/10* (2013.01); *A61L 2/084* (2013.01); *A61M 16/0465* (2013.01);
(Continued)

(58) Field of Classification Search
CPC ... A61L 2/08; A61L 2/084; A61L 2/10; A61L 2/0047; A61L 2/0052; A61L 2202/11;
(Continued)

(56) References Cited

U.S. PATENT DOCUMENTS

| 4,412,834 A | 11/1983 | Kulin et al. |
| 5,260,020 A | 11/1993 | Wilk et al. |

(Continued)

FOREIGN PATENT DOCUMENTS

WO 2014159874 A1 10/2014

OTHER PUBLICATIONS

International Preliminary Report on Patentability received in international app. no. PCT/US2019/030597, dated Dec. 30, 2020 (7 pages).

(Continued)

*Primary Examiner* — Kendra D Carter
*Assistant Examiner* — Jaeick Jang
(74) *Attorney, Agent, or Firm* — Edell, Shapiro & Finnan, LLC

(57) ABSTRACT

According to one implementation an apparatus for bacterially disinfecting a surface is provided. The apparatus includes a flexible body that contains therein at least one radially emitting optical fibers that is configured to emit bacterial disinfecting light. The radially emitting fibers having an axial and/or radial freedom of movement within a channel in which it is housed inside the flexible body such that when the flexible body changes shape the axial and/or radial freedom of movement reduces the amount of tensile stress applied along the length of the radially as compared to an amount of tensile stress that would otherwise be applied to the radially emitting fiber in an absence of the axial and/or radial freedom of movement of the radially emitting fiber inside the channel.

22 Claims, 54 Drawing Sheets

(51) Int. Cl.
*A61M 16/04* (2006.01)
*A61M 16/08* (2006.01)
*A61M 39/02* (2006.01)
*F21V 8/00* (2006.01)
*G02B 6/04* (2006.01)

(52) U.S. Cl.
CPC .... *A61M 16/0493* (2014.02); *A61M 16/0816* (2013.01); *A61L 2202/11* (2013.01); *A61L 2202/24* (2013.01); *A61M 16/0497* (2013.01); *A61M 16/0833* (2014.02); *A61M 2039/0285* (2013.01); *A61M 2205/053* (2013.01); *A61M 2209/10* (2013.01); *G02B 6/0005* (2013.01); *G02B 6/04* (2013.01)

(58) Field of Classification Search
CPC .............. A61L 2202/24; A61M 16/04; A61M 16/0461; A61M 16/0463; A61M 16/0465; A61M 16/0493; A61M 16/0497; A61M 2209/10; A61M 2039/0285; A61M 2205/0238; A61M 2205/053; A61M 2205/11; A61M 2207/00; A61M 16/0816; A61M 16/0833; A61M 16/0875; A61M 16/0883; G02B 6/0005; G02B 6/0006; G02B 6/0008; G02B 6/001; G02B 6/028; G02B 6/02; G02B 6/04; G02B 6/102; B01D 2257/91; B01D 2259/802; B01D 2259/804
See application file for complete search history.

(56) References Cited

U.S. PATENT DOCUMENTS

| | | | |
|---|---|---|---|
| 5,637,877 A | 6/1997 | Sinofsky | |
| 5,695,482 A | 12/1997 | Kaldany | |
| 5,855,203 A * | 1/1999 | Matter | A61M 16/08 128/207.14 |
| 6,443,147 B1 | 9/2002 | Matter | |
| 6,461,569 B1 | 10/2002 | Boudreaux | |
| 6,524,529 B1 | 2/2003 | Horton, III | |
| 6,564,087 B1 | 5/2003 | Pitris et al. | |
| 7,274,844 B2 | 9/2007 | Walt et al. | |
| 7,686,839 B2 | 3/2010 | Parker | |
| 8,197,087 B2 | 6/2012 | Sobue et al. | |
| 8,431,910 B1 | 4/2013 | Perry | |
| 8,556,950 B2 | 10/2013 | Rioux et al. | |
| 8,574,490 B2 | 11/2013 | Haytman et al. | |
| 8,632,576 B2 | 1/2014 | Quisenberry | |
| 8,702,640 B2 | 4/2014 | Dacey, Jr. et al. | |
| 8,706,211 B2 | 4/2014 | Dacey, Jr. et al. | |
| 8,953,914 B2 | 2/2015 | Genier | |
| 9,259,513 B2 | 2/2016 | Bedwell et al. | |
| 9,278,148 B2 | 3/2016 | Fewkes et al. | |
| 9,295,742 B2 | 3/2016 | Rasooly et al. | |
| 9,618,672 B2 * | 4/2017 | Kuchinisky | G02B 6/001 |
| 9,925,285 B1 | 3/2018 | Zaborsky | |
| 10,245,424 B2 * | 4/2019 | Cohen | A61M 39/16 |
| 10,870,015 B2 * | 12/2020 | Barneck | A61M 16/04 |
| 2002/0025097 A1 | 2/2002 | Cooper et al. | |
| 2002/0037133 A1 | 3/2002 | Unsworth | |
| 2003/0017073 A1 | 1/2003 | Eckhardt et al. | |
| 2005/0175658 A1 | 8/2005 | Dimauro et al. | |
| 2005/0279354 A1 | 12/2005 | Deutsch et al. | |
| 2006/0140562 A1 | 6/2006 | Joseph et al. | |
| 2006/0206997 A1 | 9/2006 | Chiang et al. | |
| 2011/0291995 A1 | 12/2011 | Shr et al. | |
| 2012/0321509 A1 | 12/2012 | Bak | |
| 2013/0035629 A1 | 2/2013 | Soltz et al. | |
| 2013/0115131 A1 | 5/2013 | Hegg et al. | |
| 2013/0267888 A1 | 10/2013 | Rhodes et al. | |
| 2014/0119915 A1 | 5/2014 | Ruijter | |
| 2015/0043875 A1 | 2/2015 | Bookbinder et al. | |
| 2015/0126976 A1 | 5/2015 | Tang et al. | |
| 2015/0148734 A1 | 5/2015 | Fewkew et al. | |
| 2015/0231287 A1 | 8/2015 | Lin et al. | |
| 2015/0335773 A1 | 11/2015 | Bauco | |
| 2016/0001038 A1 | 1/2016 | Romo et al. | |

OTHER PUBLICATIONS

International Search Report and Written Opinion in corresponding PCT Application No. PCT/US2019/030597, mailed on Jul. 19, 2019, 8 pages.

* cited by examiner

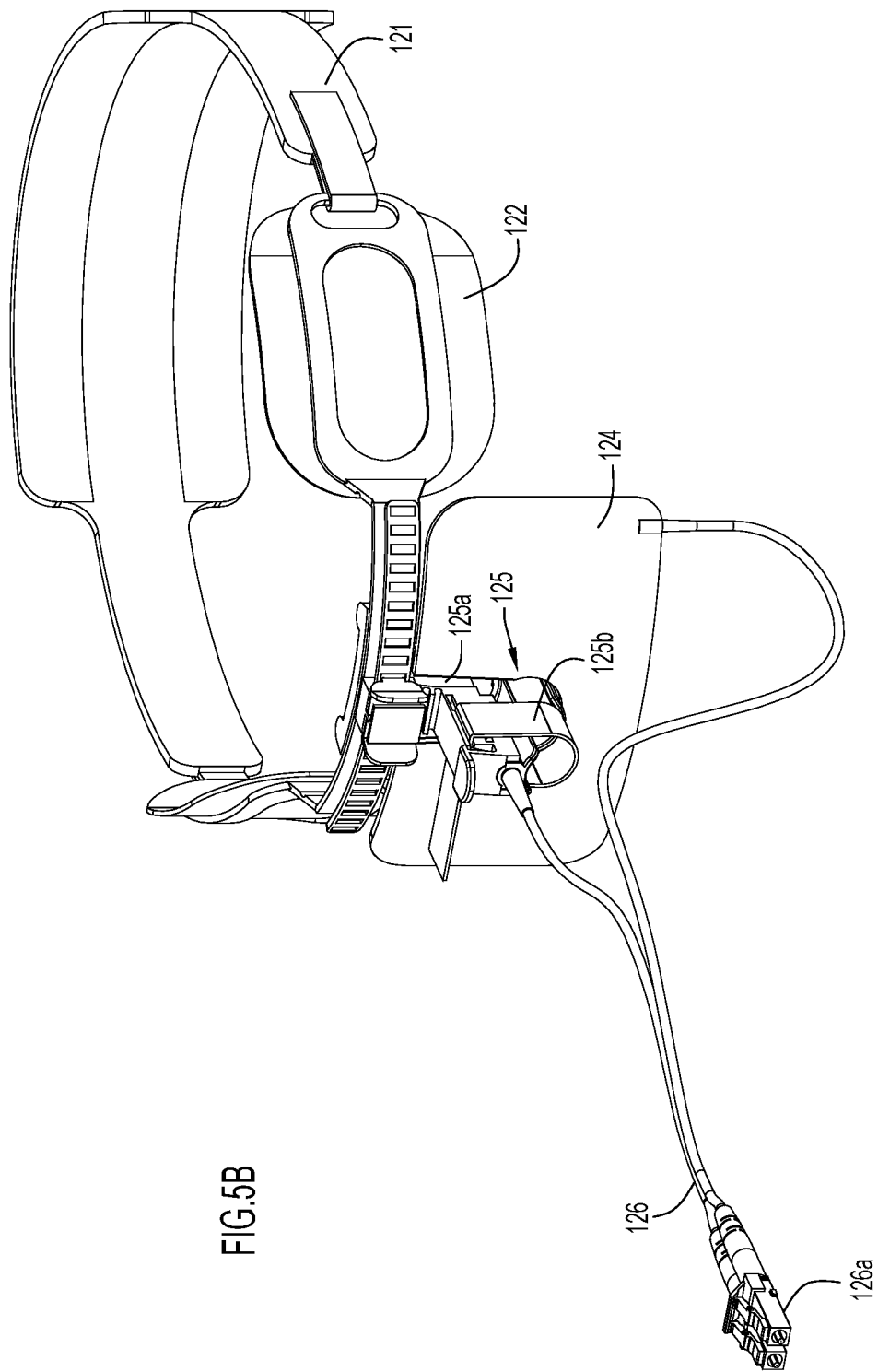

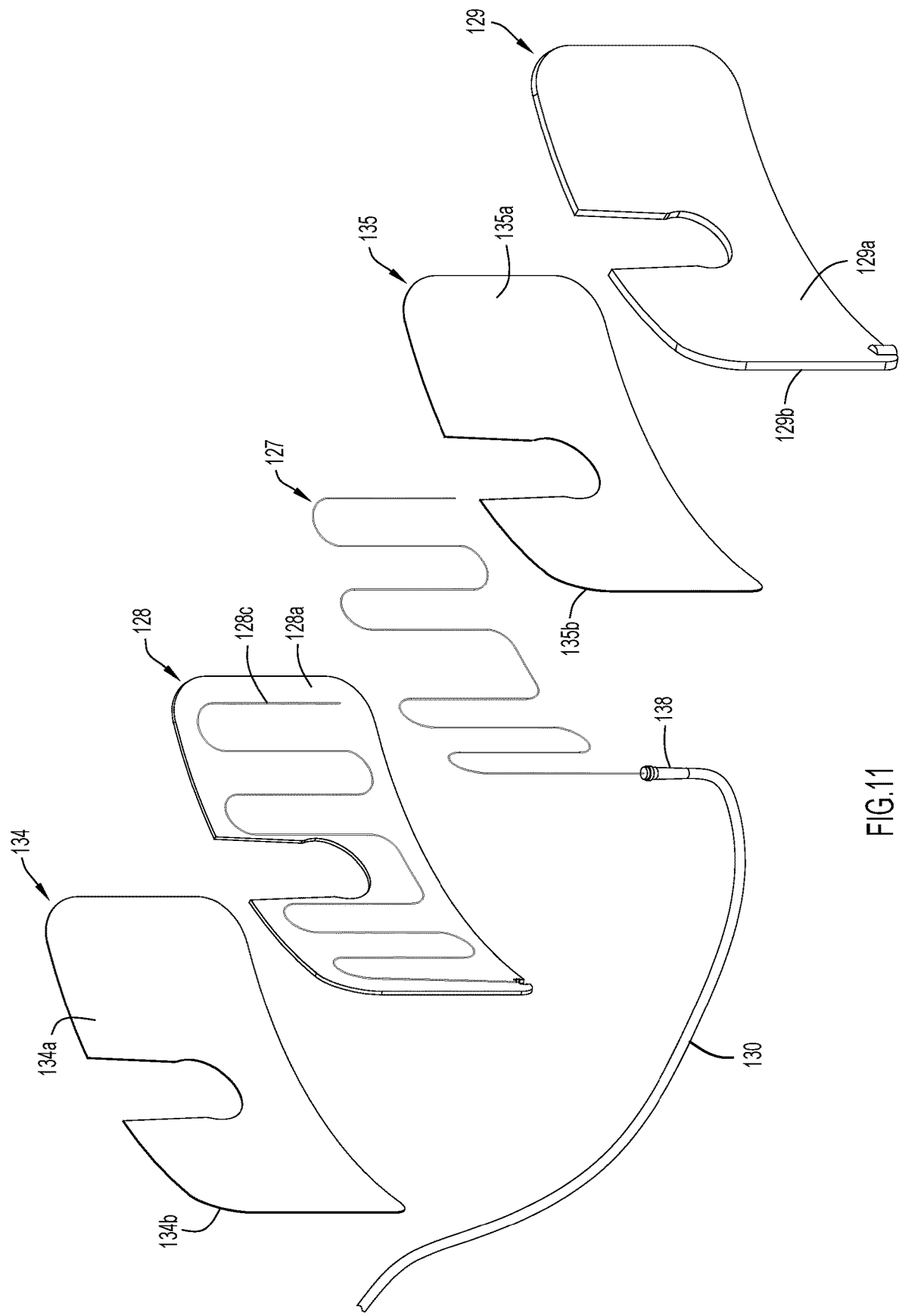

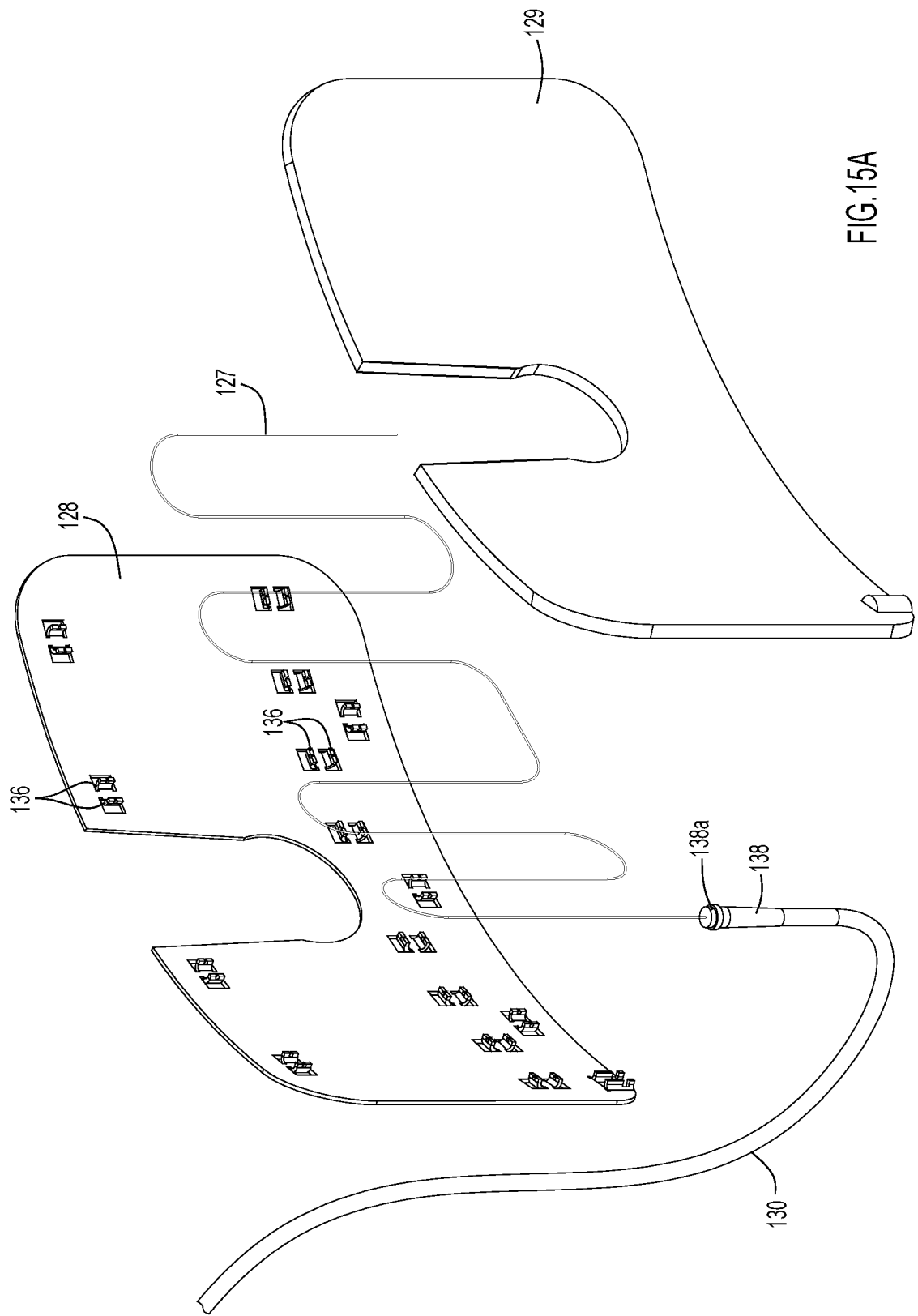

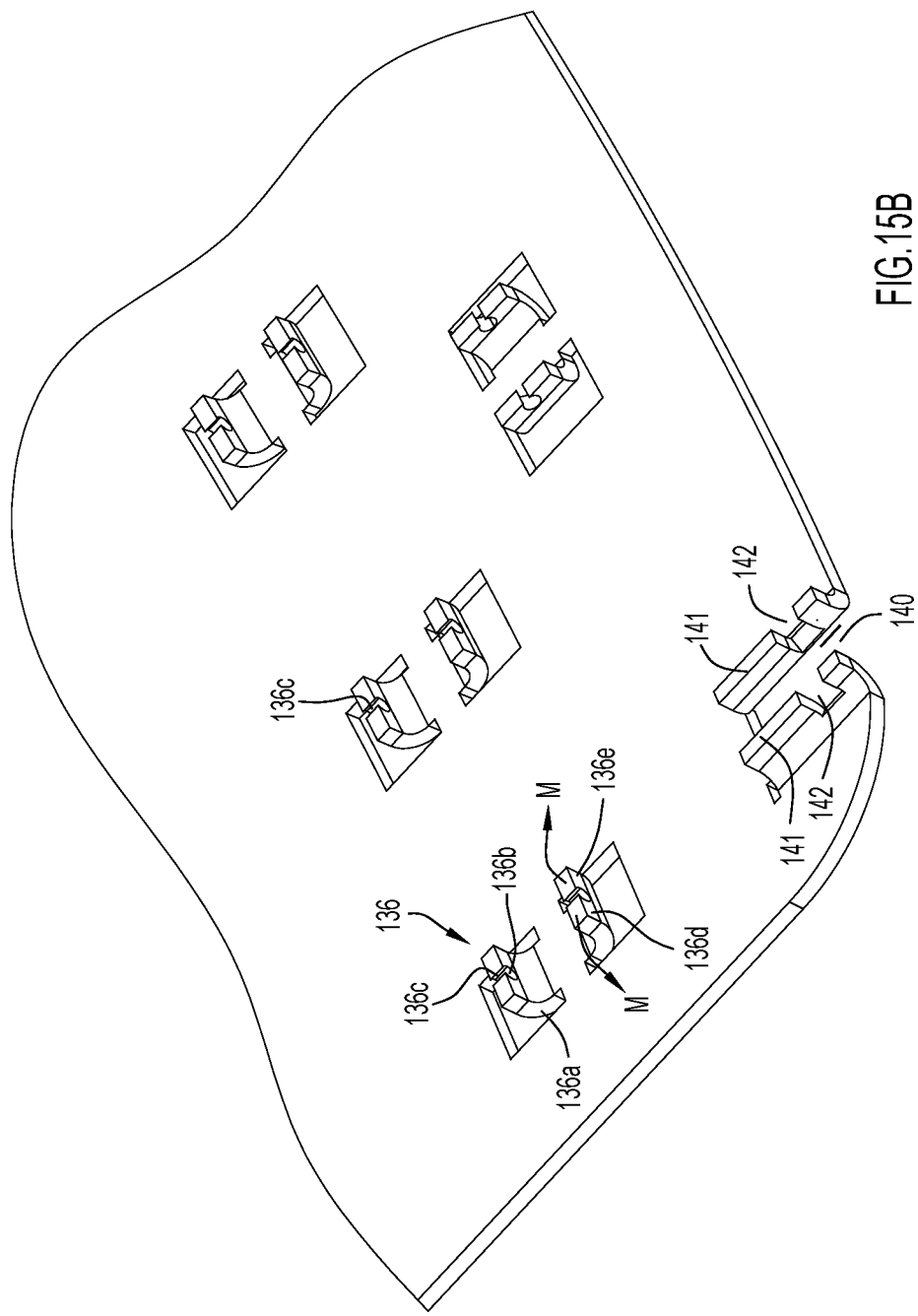

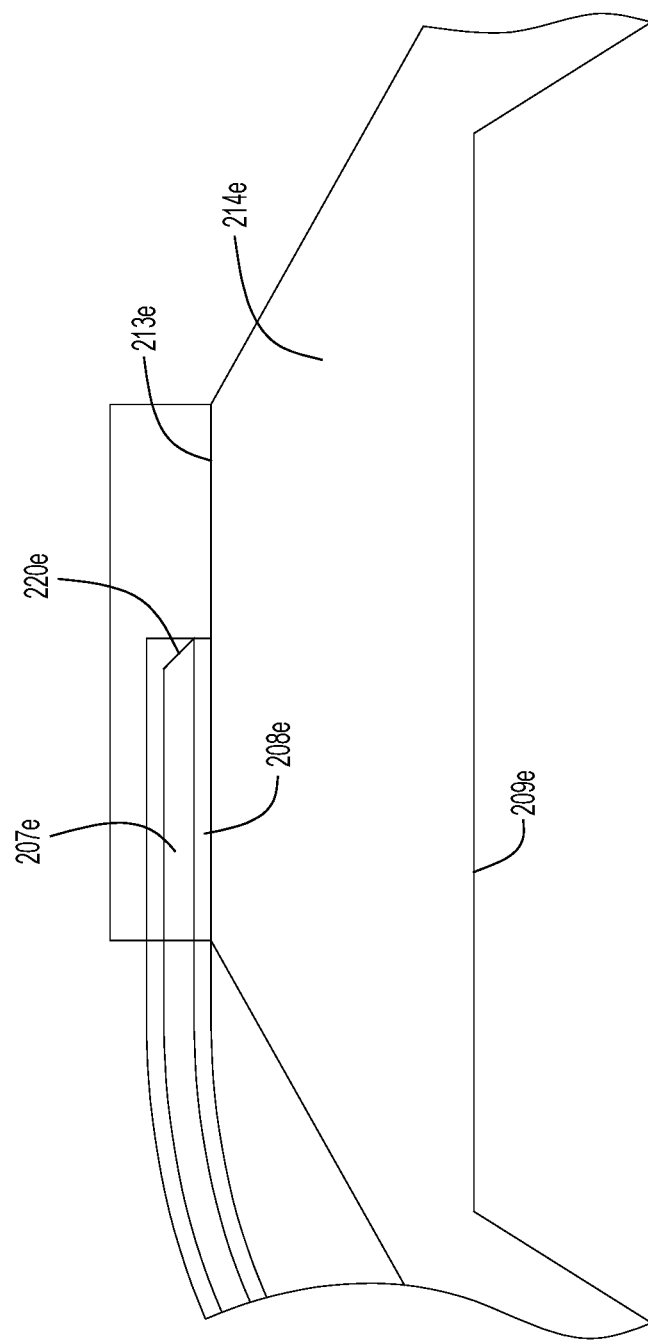

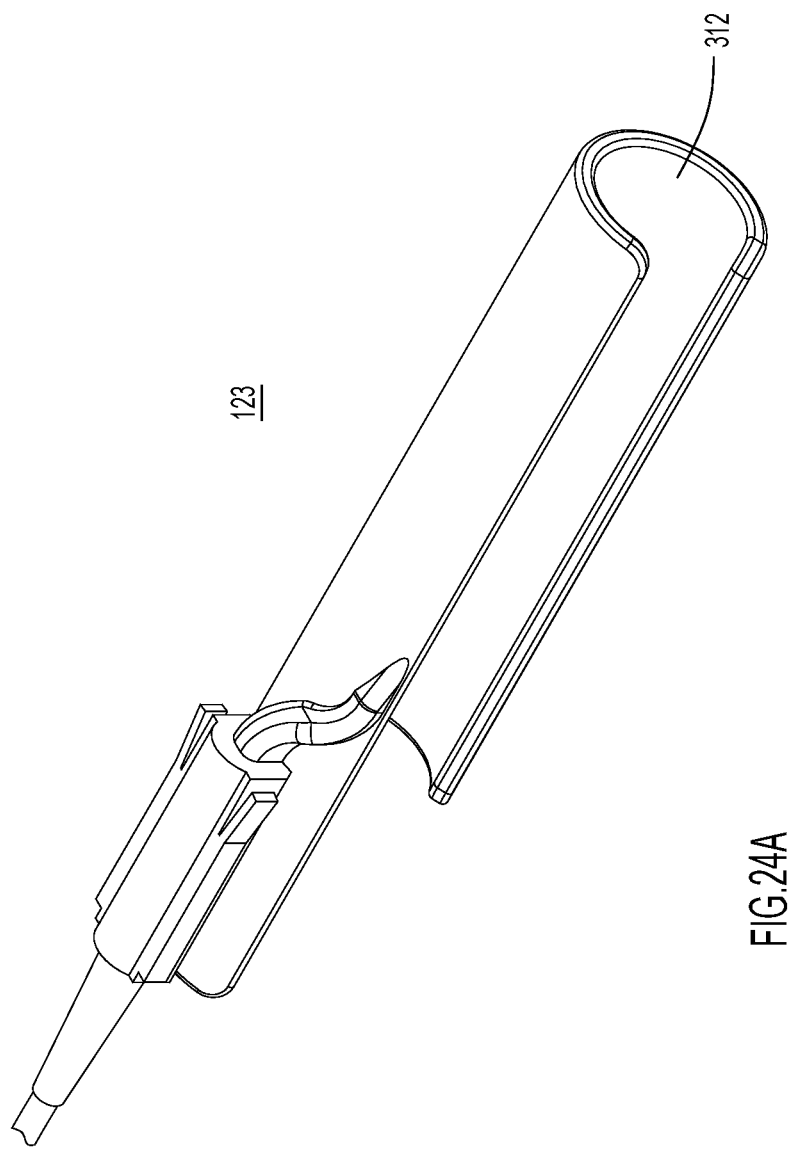

DISINFECTING METHODS AND APPARATUS

CROSS-REFERENCE TO RELATED APPLICATIONS

This application is a continuation of application Ser. No. 16/012,182, filed Jun. 19, 2018.

TECHNICAL FIELD

The present disclosure relates to devices having disinfecting capabilities and to methods for disinfecting any of a host of devices or surfaces including, for example, devices used in the medical treatment of patients.

BACKGROUND

Unwanted and dangerous bacteria growth can occur on or in devices that are commonly used to treat patients. These devices may include tracheal intubation devices that are susceptible to bacteria growth at the intubation tube and ventilator tubing set connection location, and externally on the external surface of the intubation tube, bite block and ventilator tube holder. Hospital acquired infections account for a substantial yearly expense to hospitals and insurance companies, and are a major cause of extending hospital stays for patients.

Unwanted and dangerous bacteria growth can occur on or in devices outside the medical field. Examples of non-medical devices include equipment or components of water processing plants, food processing plants, dairies, livestock habitation facilities, etc.

SUMMARY OF THE DISCLOSURE

According to some implementations disclosed herein are devices and assemblies associated with intubation tubes wherein at least some of the components of the assemblies possess optical fibers adapted to deliver bacterial disinfecting light for the purpose of disinfecting said components and areas in close proximity thereto.

According to some implementations the assemblies include a bite block through which the intubation tube is configured to pass when in use. According to some implementations the bite block has embedded therein one or more radially emitting fibers that are each connectable to a bacterial disinfecting light source, such as a laser. The light may be any wavelength of light that is capable of killing bacteria, such as, for example, ultra violet (UV) light and blue light.

According to some implementations the assemblies include a lip guard through which a bite block passes. The inner face of the lip guard is configured to face the mouth region of the patient. According to some implementations the lip guard has embedded therein one or more radially emitting fibers that are connectable to a bacterial disinfecting light source.

According to some implementations the proximal end of the intubation tube is provided with a male connector that is coupled to a female connector associated with a ventilator tube set. Bacterial growth in areas of stagnation within and around the connectors can occur. For this reason, according to some implementations one or both of the male and female connectors have embedded therein one or more optical fibers that are configured to direct bacterial disinfecting light internal to the connectors. According to some implementations the one or more optical fibers are radially emitting fibers, whereas according to other implementations the one or more optical fibers are side firing optical fibers and/or end emitting fibers.

According to some implementations, internal disinfection of the male and female connectors is accomplished through the use of a collar having embedded therein one or more optical fibers that fully, or at least partially, surround said connectors. According to some implementations the one or more optical fibers are radially emitting fibers, whereas according to other implementations the one or more optical fibers are side firing optical fibers and/or end emitting fibers.

The light emitted by the various optical fibers disclosed herein may be any wavelength of light that is capable of killing bacteria, such as, for example, ultra violet (UV) light and blue light. An advantage of using light to kill bacteria is that it is not susceptible to the danger of antimicrobial resistance that can occur with the use of pharmacologic or chemical agents. Another advantage is that there are severe side effects associated with many pharmacologic or chemical agents are avoided.

It is important to note that although the forthcoming disclosure is directed primarily to tracheal intubation devices, it is in no way limited to such devices. For example, the apparatus and methods disclosed herein related to killing bacteria with light are applicable to other types of medical devices and non-medical devices. The use of embedded optical fibers in connectors and/or collars that surround them can also be applied to other medical and non-medical devices in which connectors are used. Examples of non-medical devices include equipment or components of water processing plants, food processing plants, dairies, livestock habitation facilities, etc.

According to some implementations a flexible bacterial disinfecting apparatus is provided that is configured to bacterially disinfect surfaces of different shapes, the apparatus comprising:

a flexible body capable of assuming different shapes, the flexible body being made of a material that is transparent to light and having formed therein a channel/recess;

a radially emitting fiber having a length and being disposed in the channel/recess, the radially emitting fiber having a longitudinal axis and configured to radially emit bacterial disinfecting light, at least a portion of the radially emitting fiber having an axial and/or radial freedom of movement inside the channel/recess when the flexible body changes shape, the axial and/or radial freedom of movement reducing the amount of tensile stress applied along the length of the radially emitting fiber when the flexible body transitions between the planar and non-planar states as compared to an amount of tensile stress that would otherwise be applied to the radially emitting fiber in an absence of the axial and/or radial freedom of movement of the radially emitting fiber inside the channel/recess.

According to some implementations a method of making an apparatus for bacterially disinfecting a surface is provided that comprises:

obtaining a light transparent body that has a front face and a back face with there being a channel/recess formed in the front face;

applying to the back face of the body a light reflecting element that is configured to reflect light in a direction toward the front face of the body;

inserting a radially emitting fiber into the channel/recess to form a subassembly that includes the light transparent body, the light reflecting element and the radially emitting fiber, the radially emitting fiber being configured to radially emit bacterial disinfecting light; and injection molding a light transparent liner over at least the front face of the light transparent body.

According to some implementations a method for making an apparatus for bacterially disinfecting a surface is provided that comprises:

obtaining a light transparent body that has a front face and a back face with there being a channel/recess formed in the front face;

applying to the back face of the body a light reflecting element that is configured to reflect light in a direction toward the front face of the body, the light reflecting element having a back face and a front face that faces the back face of the body;

inserting a radially emitting fiber that is configured to radially emit bacterial disinfecting light into the channel/recess;

applying an optical diffuser element over the front face of the body and the radially emitting fiber to form a subassembly that includes the light transparent body, the light reflecting element, the radially emitting fiber and the optical diffuser element.

injection molding a light transparent liner over at least the front face of the optical diffuser.

According to some implementations a method for making an apparatus for bacterially disinfecting a surface is provided that comprises:

obtaining a light transparent body that has a front face and a back face with there being a channel/recess formed in the front face;

applying to the back face of the light transparent body a light reflecting element that is configured to reflect light in a direction toward the front face of the light transparent body, the light reflecting element having a back face and a front face that faces the back face of the light transparent body;

inserting a radially emitting fiber into the channel/recess to form a first subassembly that includes the light transparent body, the light reflecting element and the radially emitting fiber, the radially emitting fiber being configured to radially emit bacterial disinfecting light;

injection molding a light transparent first liner over the first subassembly, the first liner including a first portion that lies over the front face of the light transparent body and a second portion that lies over the back face of the light reflecting element, applying an optical diffuser element over the first portion of the first liner to form a second subassembly that includes the light transparent body, the light reflecting element, the radially emitting fiber, the first liner and the optical diffuser; and injection molding a light transparent second liner over the second subassembly.

According to some implementations an apparatus for bacterially disinfecting a surface is provided that comprises:

a tube-like body having a length and including an inner face, an outer face and a through opening, the through opening extending along the length of the tube-like body, the tube-like body being made of a material that is transparent to light and having formed in the outer face a channel/recess;

a radially emitting fiber having a longitudinal axis that is disposed in the channel/recess of the tube-like body, the radially emitting fiber having a length and configured to radially emit a bacterial disinfecting light along a majority of the length of the radially emitting fiber, the radially emitting fiber having an inner side that faces the toward the through opening and an outer side that faces away from the through opening; and a light reflecting element disposed over the outer face of the tube-like surface and the outer side of the radially emitting fiber, the light reflecting element configured to reflect the bacterial disinfecting light emitted from the outer side of the radially emitting fiber in a direction toward the through opening of the tube-like body.

According to some implementations an apparatus for bacterially disinfecting a surface is provided that comprises:

a tube-like body having a length and including an inner face, an outer face and a through opening, the through opening extending along the length of the tube-like body, the tube-like body being made of a material that is transparent to light and having formed in the outer face a channel/recess;

a radially emitting fiber having a longitudinal axis that is disposed in the channel/recess of the tube-like body, the radially emitting fiber having a length and configured to radially emit a bacterial disinfecting light along a majority of the length of the radially emitting fiber, the radially emitting fiber having an inner side that faces the toward the through opening and an outer side that faces away from the through opening; and a light reflecting element disposed over the outer face of the tube-like surface and the outer side of the radially emitting fiber, the light reflecting element configured to reflect the bacterial disinfecting light emitted from the outer side of the radially emitting fiber in a direction toward the through opening of the tube-like body.

These and other advantages and features will become evident in view of the drawings and detailed description.

BRIEF DESCRIPTION OF THE DRAWINGS

FIG. 5B shows an assembled perspective view of the endotracheal tube support assembly shown in FIG. 5A.

FIG. 11 is an exploded perspective view of a lip guard according to another implementation.

FIG. 15A is an exploded perspective view of a lip guard according to another implementation.

FIG. 15B shows in detail some of the clip connectors of the lip guard of FIG. 15A.

FIG. 20A is a partial cross-sectional top view of the first part shown in FIG. 19B with a side firing fiber located inside an air filled cavity.

FIG. 24A is a perspective view of an assembled bite block according to one implementation.

DETAILED DESCRIPTION

Figure 1A:
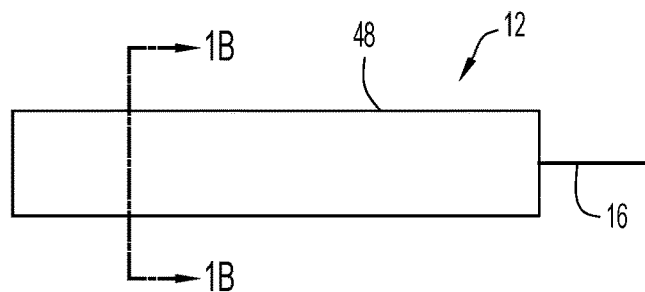
FIGS. 1A and 1B respectively show a side view and cross-section view of a radially emitting optical fiber according to one implementation.
Figure 1B:
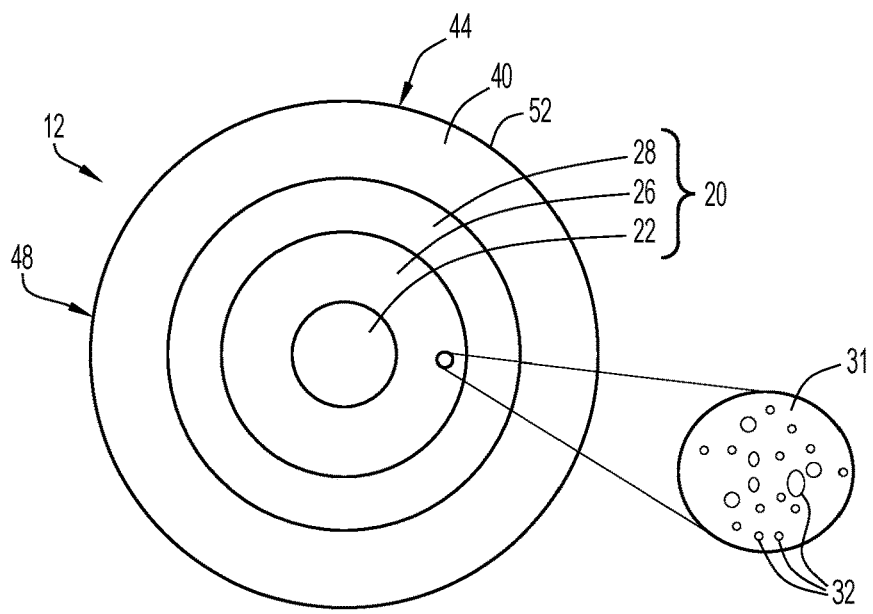

FIG. 1A is a schematic side view of a radially emitting fiber with a plurality of voids in the core of the radially emitting optical fiber 12 having a central axis 16. FIG. 1B is a schematic cross-section of a radially emitting optical fiber 12 as viewed along the direction 1B-1B in FIG. 1A. Radially emitting fiber 12 can be, for example, an optical fiber with a nano-structured fiber region having periodic or non-periodic nano-sized structures 32 (for example voids). In an example implementation, fiber 12 includes a core 20 divided into three sections or regions. These core regions are: a solid central portion 22, a nano-structured ring portion (inner annular core region) 26, and outer, solid portion 28 surrounding the inner annular core region 26. A cladding region 40 surrounds the annular core 20 and has an outer surface. The cladding 40 may have low refractive index to provide a high numerical aperture. The cladding 40 can be, for example, a low index polymer such as UV or thermally curable fluoroacrylate or silicone.

An optional coating 44 surrounds the cladding 40. Coating 44 may include a low modulus primary coating layer and a high modulus secondary coating layer. In at least some implementations, coating layer 44 comprises a polymer coating such as an acrylate-based or silicone based polymer. In at least some implementations, the coating has a constant diameter along the length of the fiber.

In other exemplary implementations, coating 44 is designed to enhance the distribution and/or the nature of radiated light that passes from core 20 through cladding 40. The outer surface of the cladding 40 or the of the outer of optional coating 44 represents the sides 48 of fiber 12 through which light traveling in the fiber is made to exit via scattering, as described herein.

A protective jacket (not shown) optionally covers the cladding 40.

In some implementations, the core region 26 of radially emitting fiber 12 comprises a glass matrix 31 with a plurality of non-periodically disposed nano-sized structures (e.g., voids) 32 situated therein, such as the example voids shown in detail in the magnified inset of FIG. 1B. In another example implementation, voids 32 may be periodically disposed, such as in a photonic crystal optical fiber, wherein the voids may have diameters between about $1 \times 10^{-6}$ m and $1 \times 10^{-5}$ m. Voids 32 may also be non-periodically or randomly disposed. In some exemplary implementations, glass 31 in region 26 is fluorine-doped silica, while in other implementations the glass may be an undoped pure silica.

The nano-sized structures 32 scatter the light away from the core 20 and toward the outer surface of the fiber. The scattered light is then diffused through the outer surface of the fiber 12 to provide the desired illumination. That is, most of the light is diffused (via scattering) through the sides of the fiber 12 and along the fiber length without the need to remove any portion of the cladding 40.

According to some implementations the nano-sized structures 32 are formed in the cladding 40 of the fiber in lieu of or in conjunction with providing nano-sized structures in the core 12.

According to some implementations the core 20 has a diameter in the range of 125-300 μm and the overall diameter of the fiber system, including the protective jacket, is in the range of 700 to 1200 μm. According to some implementation, the outer diameter of the fiber 12 without a jacket is in the range of 200-350 μm.

A detailed description of exemplary radially emitting optical fibers may be found in Reissue Pat. No. RE46,098 whose content is incorporated herein by reference in its entirety.

An example of a radially emitting optical fiber is the Fibrance® Light Diffusing Fiber manufactured by Corning® Incorporated located in Corning, New York The Fibrance® Light Diffusing Fiber has many of the attributes of the radially emitting fiber 12 described above. An advantage of the Fibrance® Light Diffusing Fiber is that it emits light essentially along its entire length and has a small functional bend radius of around 5 millimeters which allows it be easily bent to assume a host of shapes. Breakage of the fiber typically occurs when it is bent to a bend radius of less than about 2 millimeters.

Radially emitting fibers like those disclosed in Reissue Pat. No. RE46,908 do not require the removal of a light reflective component or light reflective element to enable the emission of light radially from the optical fiber.

Figure 2:
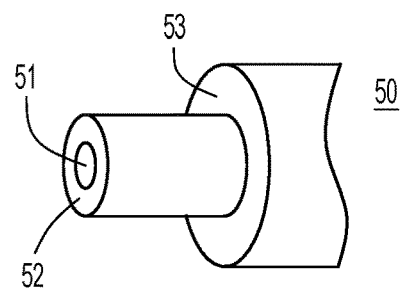
FIG. 2 is a perspective view of an end emitting optical fiber according to one implementations.

An end emitting optical fiber is an optical fiber that emits light from a terminal end of the fiber. Such emitted light is referred to herein as "end emitted light". A multimode optical fiber 50, like that shown in FIG. 2, is one example of an end emitting optical fiber wherein light is guided down the center of the fiber through the core 51 and out the end thereof. The fiber 50 includes a core 51 surrounded by a cladding 52. The cladding 52 has a lower index of refraction than the core 51 and traps the light in the core using an optical technique called "total internal reflection." The fiber 50 itself may include a coated "buffer" to protect the fiber from moisture and physical damage. The core 51 and cladding 52 are usually made of ultra-pure glass, although some fibers are all plastic or a glass core and plastic cladding. According to some implementations the core 51 has a diameter in the range of 50-250 μm and the diameter of the cladding 52 is typically around 100-500 μm. The overall diameter of the fiber system, including the buffer coating 53, is typically around 150-750 μm. Breakage of the fiber typically occurs when it is bent to a bend radius of less than about 2 millimeters.

A "transport fiber" as used herein, refers to an optical fiber that transports light longitudinally through its core to an end of the fiber with little loss. That is, the vast majority (e.g., ≥90%) of the light fed into a proximal end of the transport fiber is delivered to the terminal end of the fiber. As explained in more detail below, transport fibers are used in a variety of the implementations disclosed and contemplated herein to couple a light source (e.g., a laser) to a radially emitting optical fiber and/or end emitting fiber. According to some implementations, the transport fibers disclosed herein are multimode optical fibers.

It is important to note that a radially emitting optical fiber, like the examples discussed above, may also emit light from the core 20 at a terminal end of the radially emitting optical fiber 12. Thus, according to some implementations a disinfecting of a device may occur as a result of bacterial disinfecting light being emitted from both the circumference and the end of a radially emitting fiber. An optical fiber designated for this use is referred to herein as a "dual emitting fiber".

Blue light and ultra-violet light have been shown to kill or curtail the growth of certain types of unwanted bacteria that is hazardous and potentially fatal to mammalian life. Examples of such bacteria are *Staphylococcus aureus, Pseudomonas aeruginosa, Leuconostoc mesenteroides, Bacillus atrophaeus, Escherichia coli*, Coagulase-negative staphylococci etc. In treatments involving a mammal, blue light is preferred over ultra-violet light due to detrimental effects of ultra-violet light on mammalian cells and possible damage to host tissue. In accordance with some implementations disclosed herein blue light at a wavelength of between 400-495 nm and an exposure of between 100-1,000 Joules/cm$^2$ is employed to kill the unwanted bacteria. According to other implementations, ultra-violet light at a wavelength of 10-400 nm and exposure up to 6 J/cm$^2$ is employed to kill unwanted bacteria.

It is important to note that the present disclosure is in no way limited to the use of blue light and ultra-violet light to kill unwanted bacteria. As briefly explained above, the present disclosure contemplates the use of any type of light that is susceptible to killing unwanted bacteria.

Figure 3A:
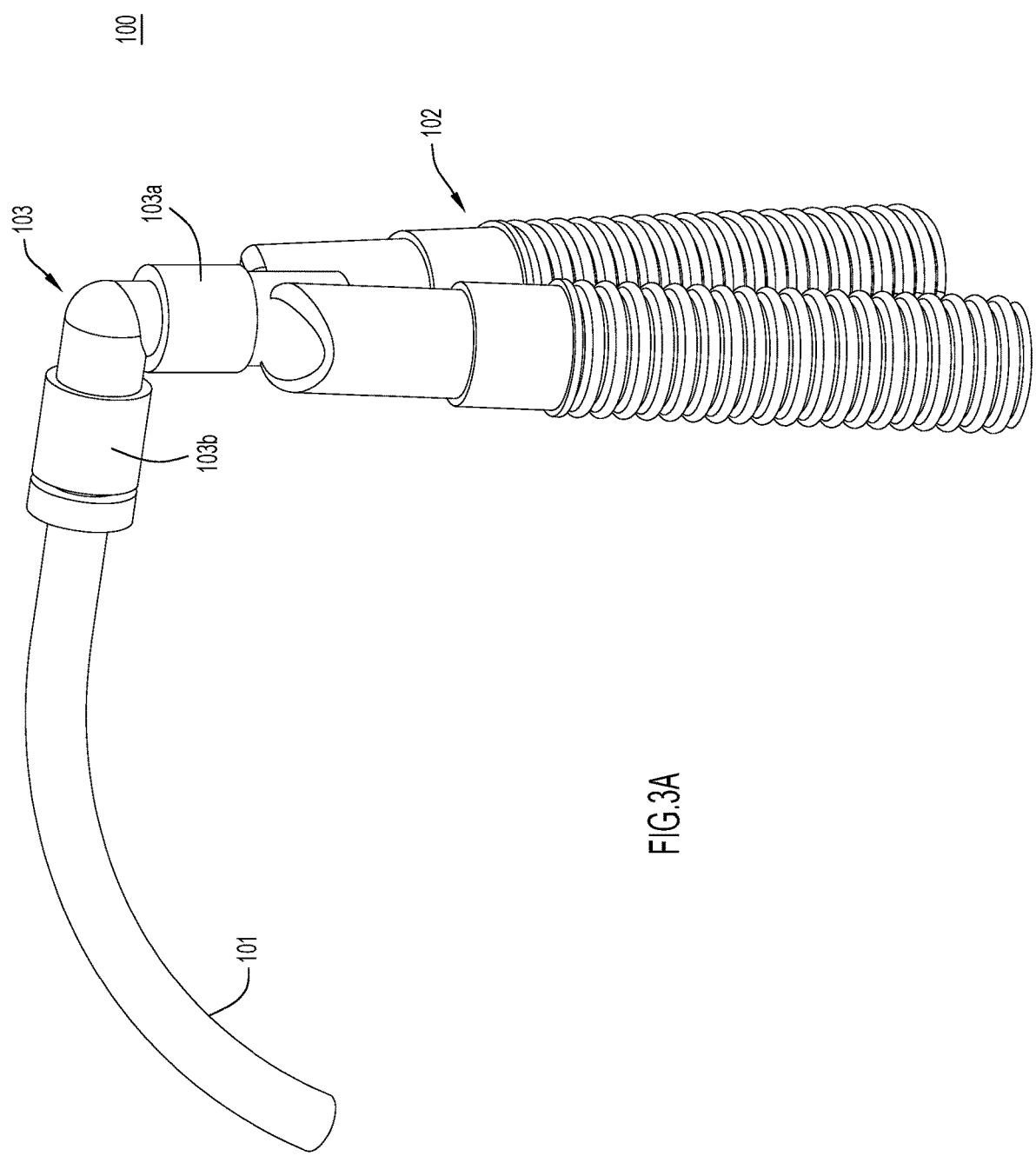
FIG. 3A is a perspective view of an endotracheal tube assembly.
Figure 3B:
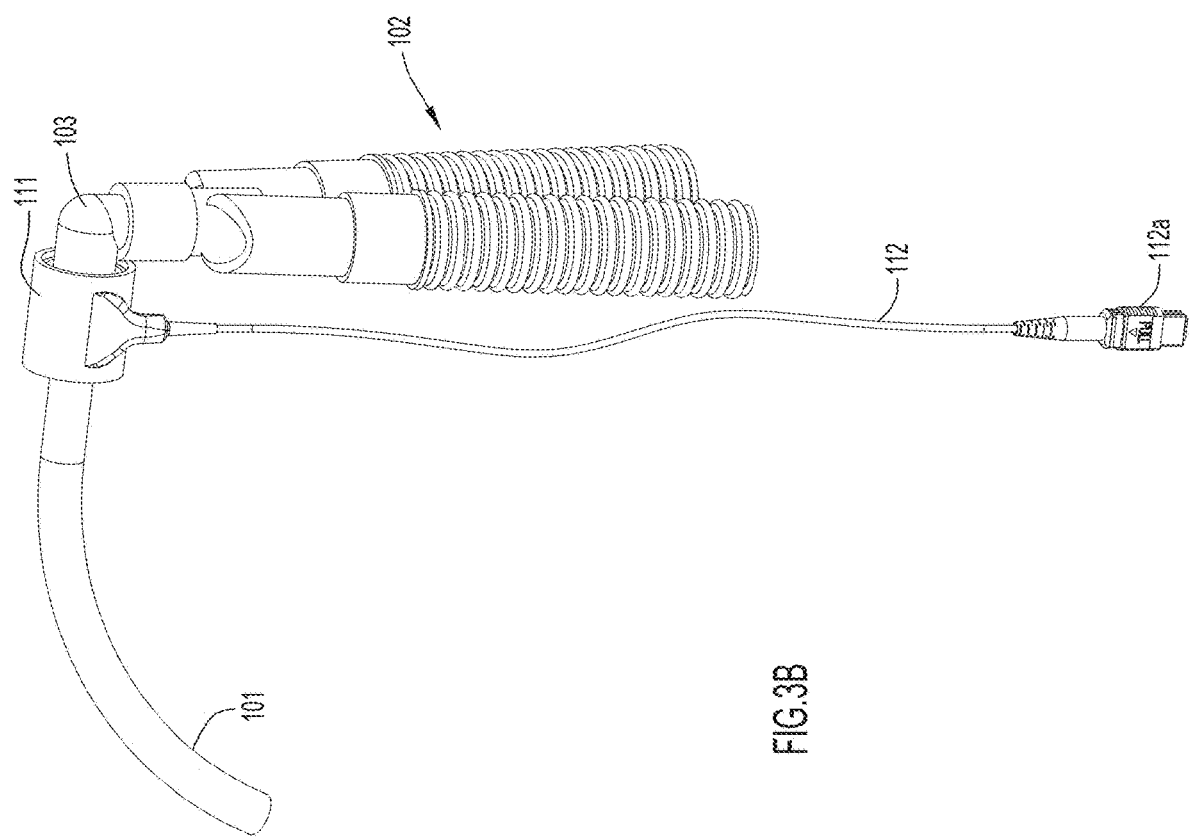
FIG. 3B illustrates the endotracheal tube assembly of FIG. 3A having a light disinfecting element disposed about a connector that connects a ventilator tube set to an intubation tube.
Figure 3C:
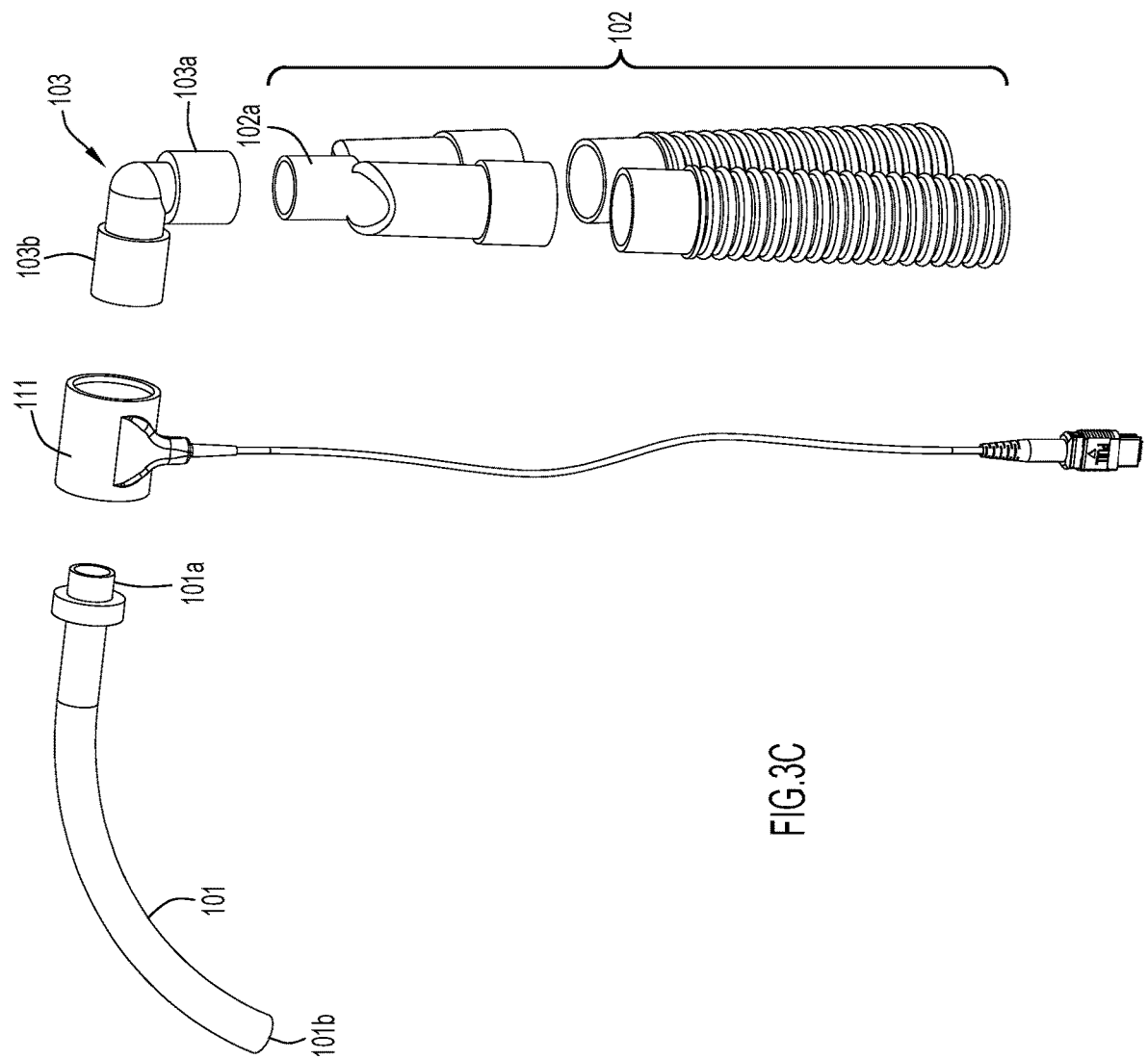
FIG. 3C is an exploded perspective view of the endotracheal tube assembly shown in FIG. 3B.

FIGS. 3A-C depict perspective views of an endotracheal tube assembly (ETA) 100 according to one implementation. The ETA includes an intubation tube 101 that is connected to a ventilator tube set 102 via a connector 103. The intubation tube has a proximal end portion 101a for connection to the connector 103 and a distal end portion 101b that is configured for placement in the trachea of a patient. According to one implementation, the connector 103 is L-shaped and includes first and second ends 103a and 103b, each in the form of a female part. In such an implementation, an end 102a of the ventilator tube set 102 resides inside the first end 103a of the connector and the proximal end portion of 101a of the intubation tube 100 resides inside the second end 103b of the connector 103. It is appreciated that any of a variety of connection schemes may be employed to facilitate a fluid/air connection of the proximal end of the intubation tube 101 to the ventilator tube set 102.

According to one aspect, one or more light disinfecting features are integrated in the connector 103 or are disposed about the connector 103 to effectuate a disinfecting of one or both of the connection locations of the intubation tube 101 with the connector 103 and the ventilator tube set 102 with the connector 103. According to one implementation, as shown in FIGS. 3B and 3C, the light disinfecting feature includes a light disinfecting collar 111 disposed about an area of the connector 103 where the proximal end portion 101a of the intubation tube 101 is connected to the second end 103b of the connector. The light disinfecting collar 111 includes one or more lighting features disposed therein that are configured to deliver bacterial disinfecting light inward toward the connection location of the proximal end of the intubation tube 101 with the connector 103. According to one implementation bacterial disinfecting light is delivered to the light disinfecting collar 111 from a light source via an optical fiber set 112 that includes one or more optical fibers located inside a jacket and connected to an optical connector 112a. According to one implementation the optical connector 112a is an MPO connector that is configured for attachment to a laser light source. Other types of connectors, such as LC connectors, may also be used. As noted above, according to some implementations the one or more light disinfecting features may alternatively be disposed on or in the connector 103 itself obviating the need for a separate collar. That is, one or more light features, such as radially emitting fibers, end emitting fibers and side firing fibers may be disposed about an outer surface of the connecter 103 (e.g.

about one or both of the first and second end parts 103*a* and 103*b*) and/or integrated/embedded inside the connector 103.

Figure 4A:
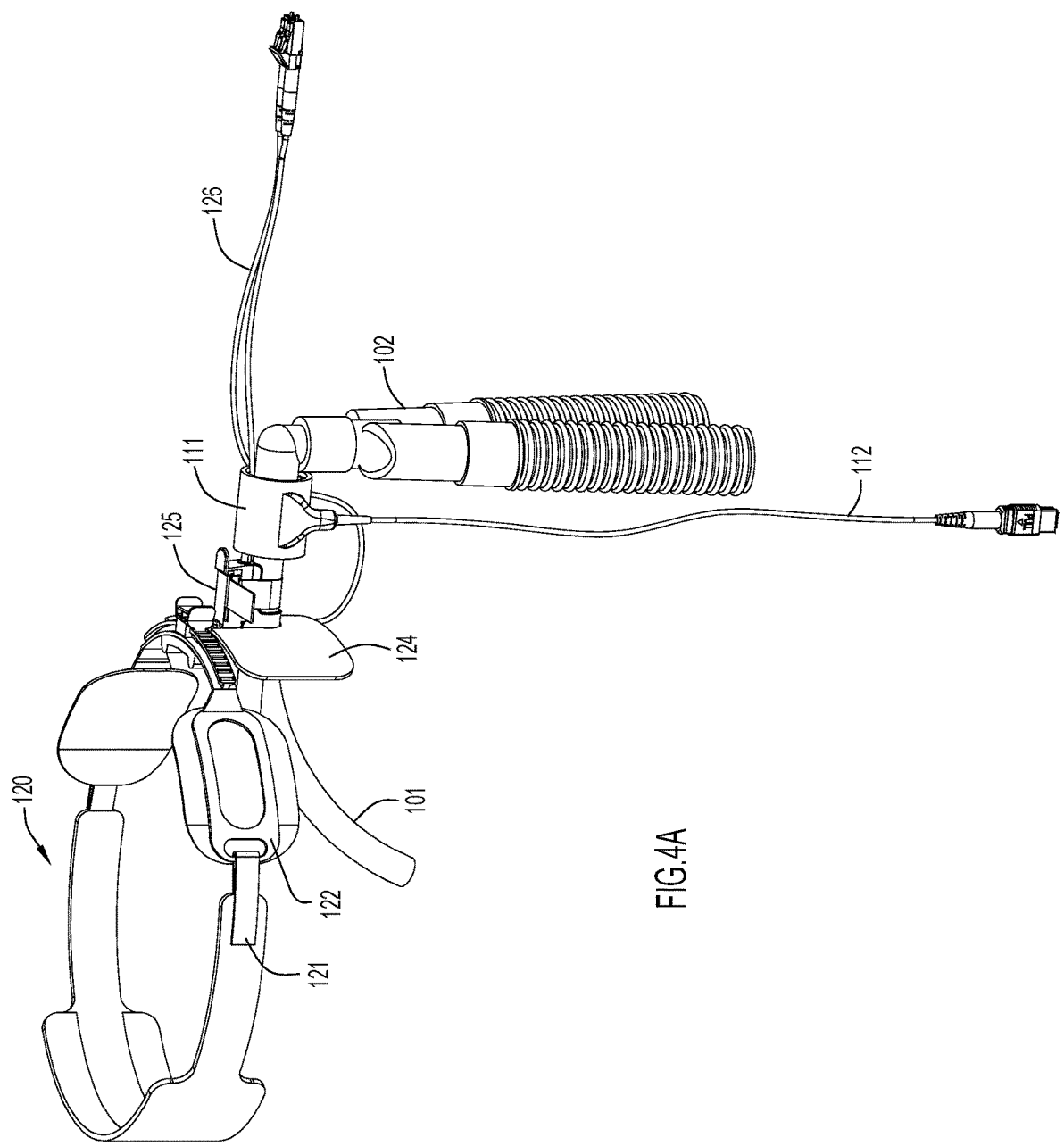
FIGS. 4A and 4B show perspective views of an endotracheal tube support assembly according to one implementation.
Figure 4B:
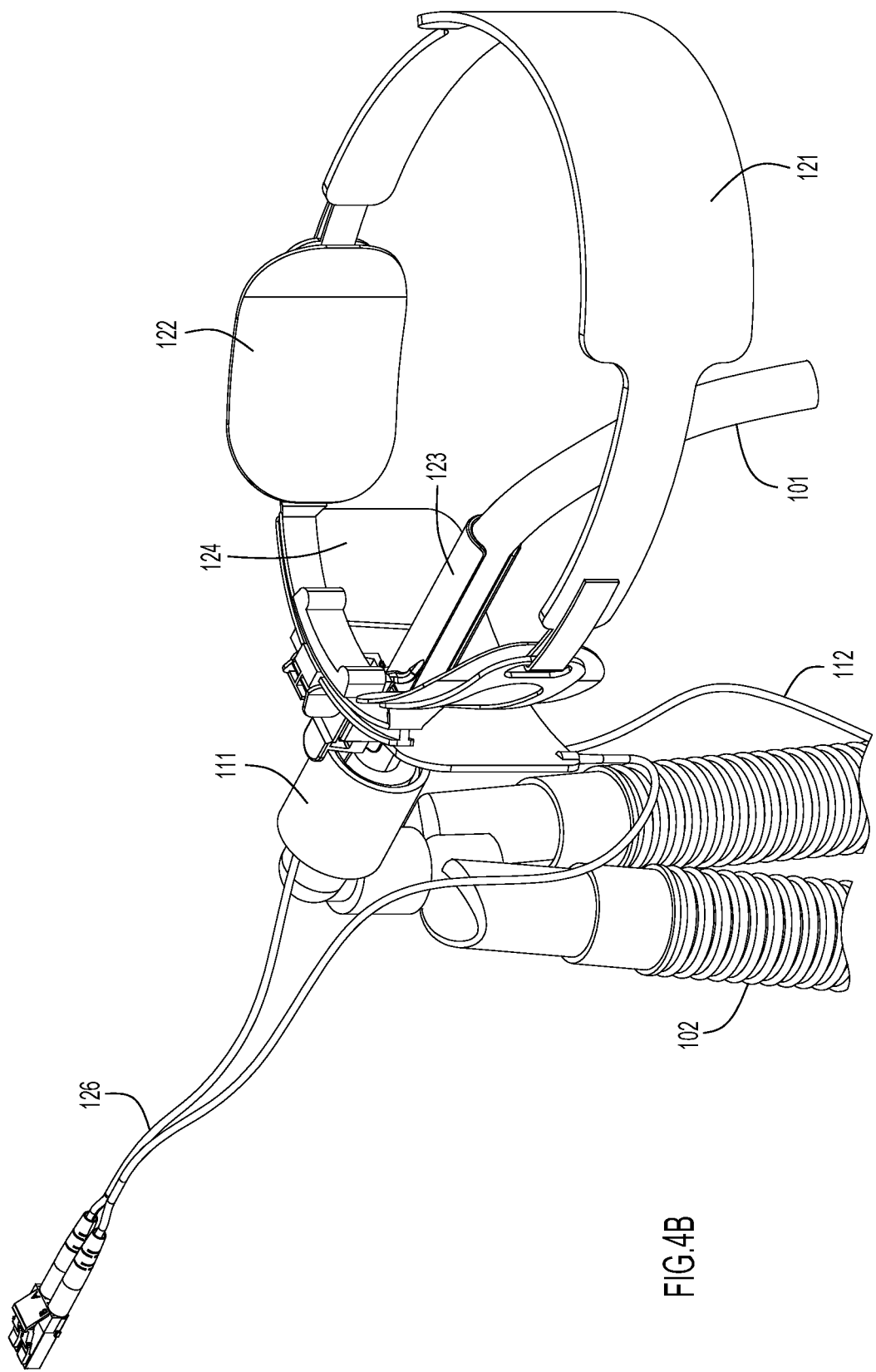

FIGS. 4A and 4B show perspective views of the ETA 100 of FIG. 3B coupled with an endotracheal tube support assembly 120 according to one implementation. In the example shown, the support assembly 120 includes an adjustable headband 121 configured for placement about the head of a patient. According to some implementations face pads 122 are secured to the headband 121 to assist in stabilizing the support assembly on the patient. The support assembly 120 also includes a bite block 123 through which a proximal portion of the intubation tube 101 passes and is supported. According to some implementations a lip guard 124 is also provided to protect and disinfect the mouth region of the patient during intubation. As will be discussed in more detail below, one or both of the bite block 123 and lip guard 124 may be equipped with one or more bacterial disinfecting light features that are disposed on and/or integrated therein for the purpose of impeding bacterial growth on the devices during intubation. According to one implementation when both the bite block 123 and lip guard 124 are equipped with disinfecting light features, a dual optical fiber set 126 having a duplex LC connector 126*a* may be used to connect the respective disinfecting light elements to a bacterial disinfecting light source.

According to one implementation, a tube holder 125 configured to support the bite block 123 is attached to the headband 121. According to one implementation the tube holder 125 includes a frame 125*a* attached to and slideable on the headband 121 and an adjustable flexible band 125*b* coupled with the frame 125*a*. In use, the bite block 123 is passed through the flexible band 125*b* with the flexible band being tightened about the outer surface of the bite block. The flexible band 125*b* may thereafter be loosened to facilitate a removal of the bite block 123 from the tube holder 125.

Figure 5A:
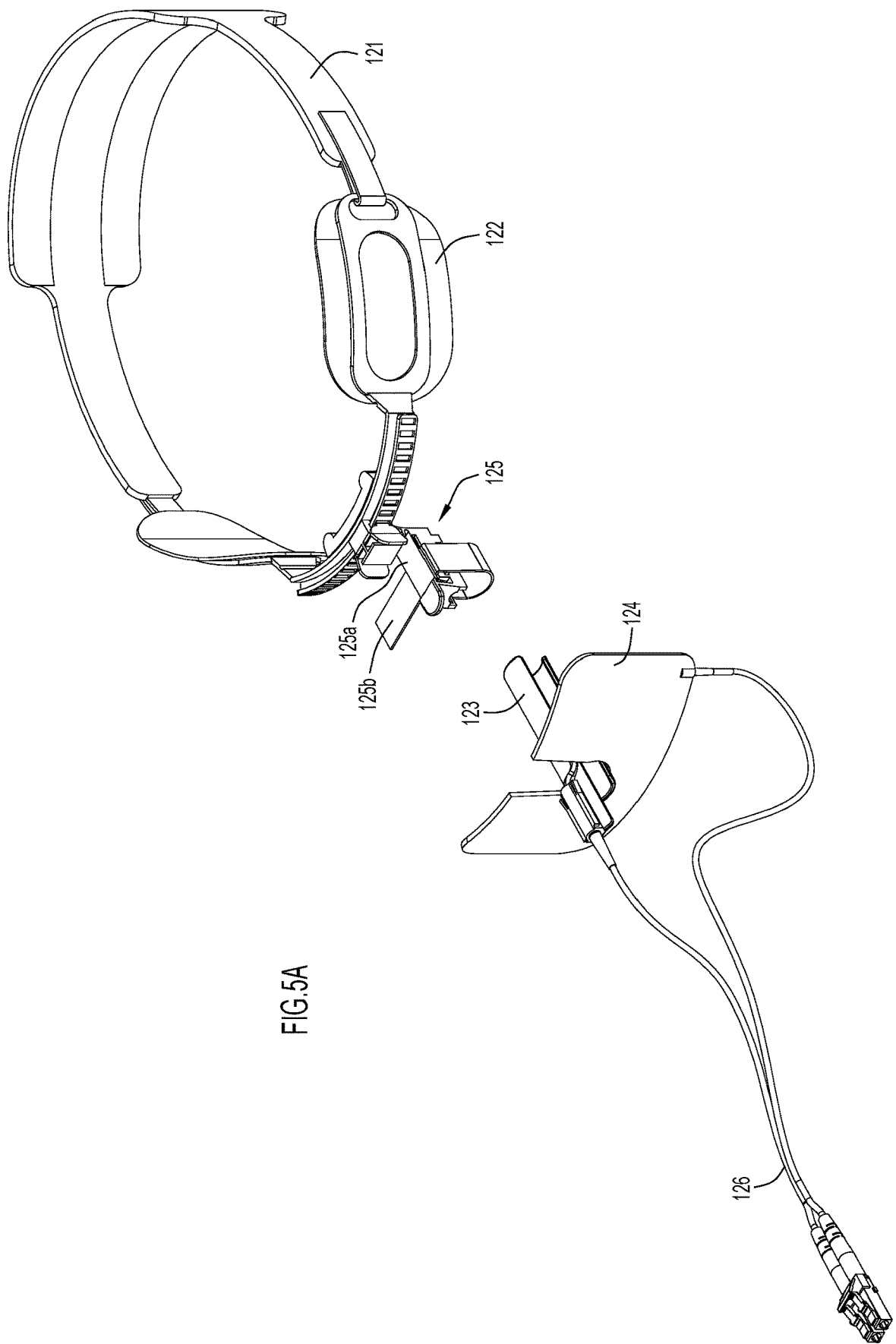
FIG. 5A shows an exploded perspective view of an endotracheal tube support assembly according to one implementation.

FIGS. 5A and 5B respectively show an exploded perspective view and a perspective view of the endotracheal tube support assembly 120 according to one implementation.

Figure 6A:
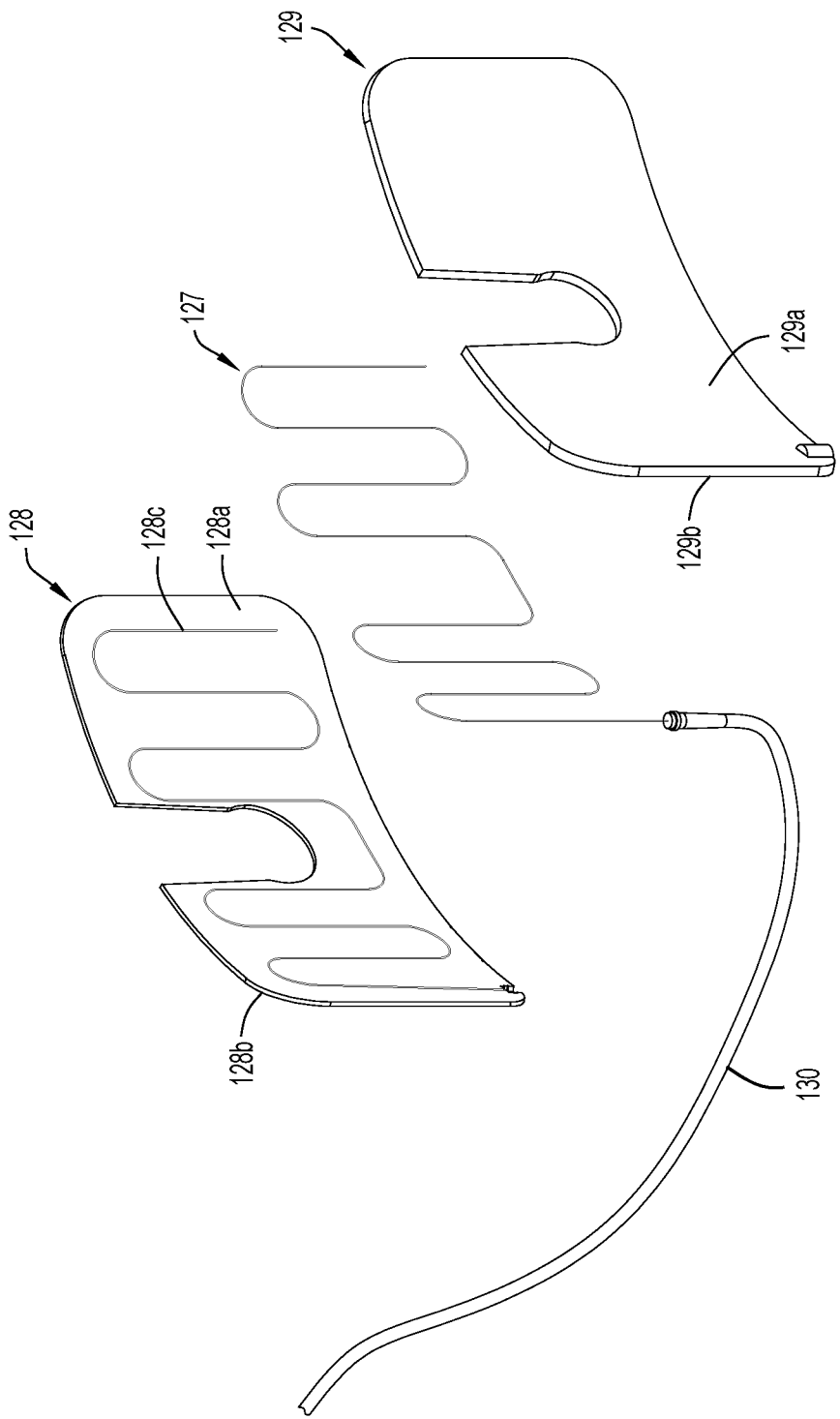
FIG. 6A shows an exploded perspective view of a lip guard according to one implementation.
Figure 6B:
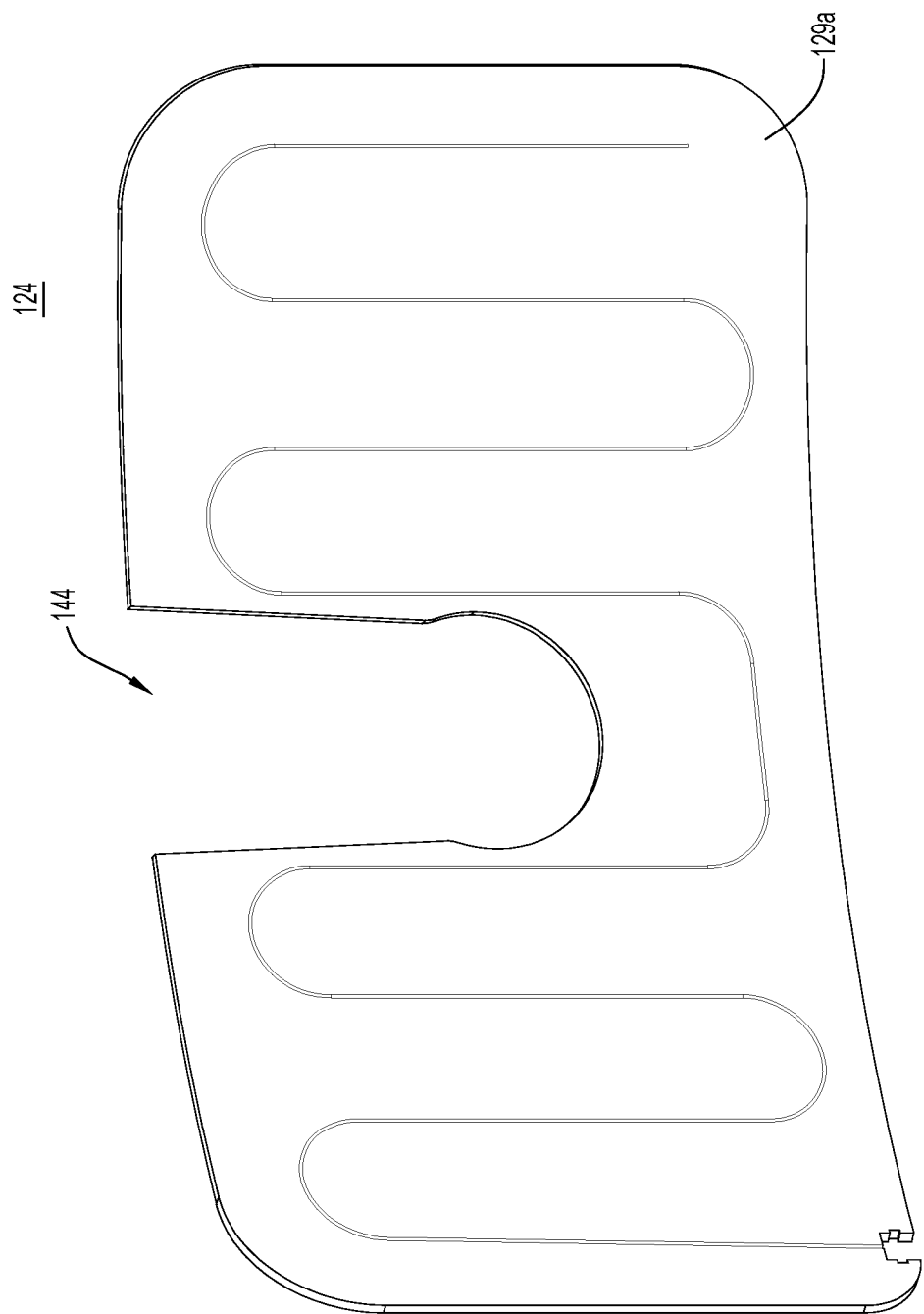
FIG. 6B shows an assembled front perspective view of the lip guard shown in FIG. 6A.

As discussed above, according to some implementations the lip guard 124 is equipped with one or more light disinfecting features (e.g. one or more radially emitting fibers) that are configured to emit light to bacterially disinfect the mouth region of a patient during an intubation. FIG. 6A illustrates an exploded perspective view of a lip guard according to one implementation. The lip guard 124 is comprised of a radially emitting fiber 127 sandwiched between a flexible substrate 128 and a liner 129. The radially emitting fiber 127 is connected to a transport fiber 130 that is coupleable to a bacterial disinfecting light source. The flexible substrate 128 has a front face 128*a* and a back face 128*b*. Likewise, the liner 129 has a front face 129*a* and a back face 129*b*. According to some implementations the flexible substrate 128 is made of a polymer (e.g. rubber) or a flexible sheet of metal. The liner 129 is also composed of a flexible material and is transparent to light at least in the visible spectrum. The lip guard includes an opening 144 to accommodate a passage of a bite block that is discussed in more detail below. According to other implementations one or both of the substrate 128 and liner 129 are not flexible.

Figure 8A:
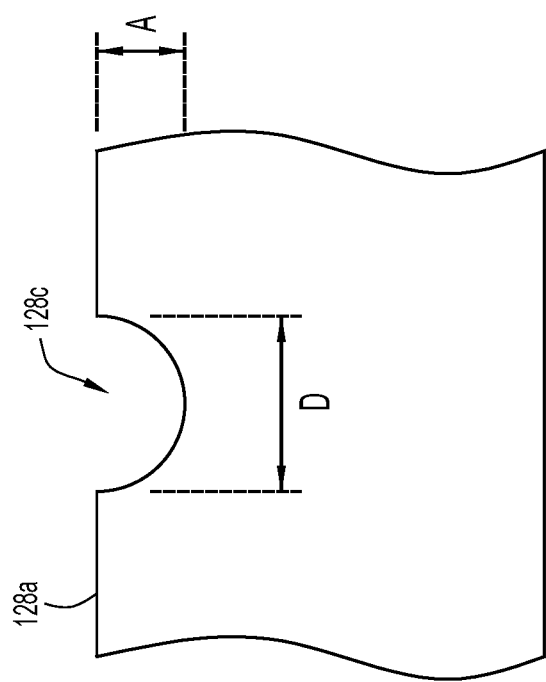
FIGS. 8A-D show cross-sectional views of a recesses formed in a substrate of a lip guard, the recesses being configured to house at least partially encompass a radially emitting fiber.

The parts of the lip guard 124 may be made and assembled in a variety of ways. According to one implementation the front face 128*a* of the flexible substrate 128 and the back face 129*b* of the liner 129 are adhesively attached to one another with each pressing against a meandering radially emitting fiber 127 disposed between them. According to some implementations, recesses 128*c* are formed in the inner face 128*a* of the flexible substrate 128 for housing the radially emitting fiber 27. FIG. 8A shows a U-shaped recess 128*c* that is configured to receive and house a radially emitting fiber 127. According to some implementations the recesses 128*c* are structured to hold the meandering radially emitting fiber 127 to the flexible substrate 128 prior to an attachment of the liner 129 to the flexible substrate 128. An example of such recesses is discussed below in conjunction with FIGS. 8B and 8C. According to other implementations the radially emitting fiber 127 is secured to the flexible substrate 128 by the use of an optically transparent adhesive prior to the liner 129 being attached to the flexible substrate 128. According to one such implementations, the radially emitting fiber 127 is adhered to the front face 128*a* in a meandering pattern without the use of recesses formed in the front face to house the fiber. According to another such implementation, the flexible substrate 128 is provided with a meandering recess 128*c*, like for example the U-shaped recess shown in FIG. 8A, with the radially emitting fiber being adhered to the flexible substrate inside the recess.

Figure 10A:
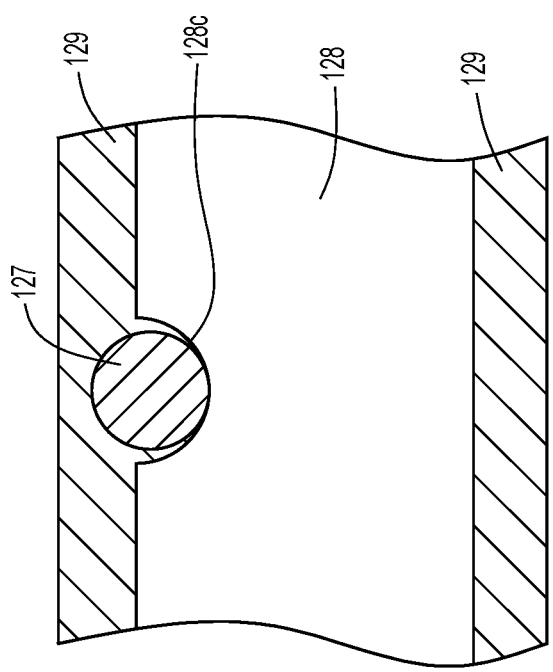
FIGS. 10A-D show cross-sectional views of lip guards according to various implementations.

According to some implementations an injection molding process is used to form the flexible substrate 128 in a manner that produces recesses 128*c* arranged in a meandering pattern in the front face 128*a* of the flexible substrate. Upon the flexible substrate 128 being formed as shown in FIG. 6A, the radially emitting fiber 127 is positioned within the recesses 128*c* to form a subassembly. Thereafter, the liner 129 is injection molded over portions of or the entirety of the subassembly such that the flexible substrate 128 containing the radially emitting fiber 127 is partially or fully enveloped by the liner 129 like that shown in the examples of FIGS. 10A-10C. As noted above, the liner 129 comprises a material, such as a polymer, that is transparent to light at least in the visible spectrum. According to some implementations, the material from which the flexible substrate 128 is made is also transparent to light at least in the visible spectrum.

Figure 8B:
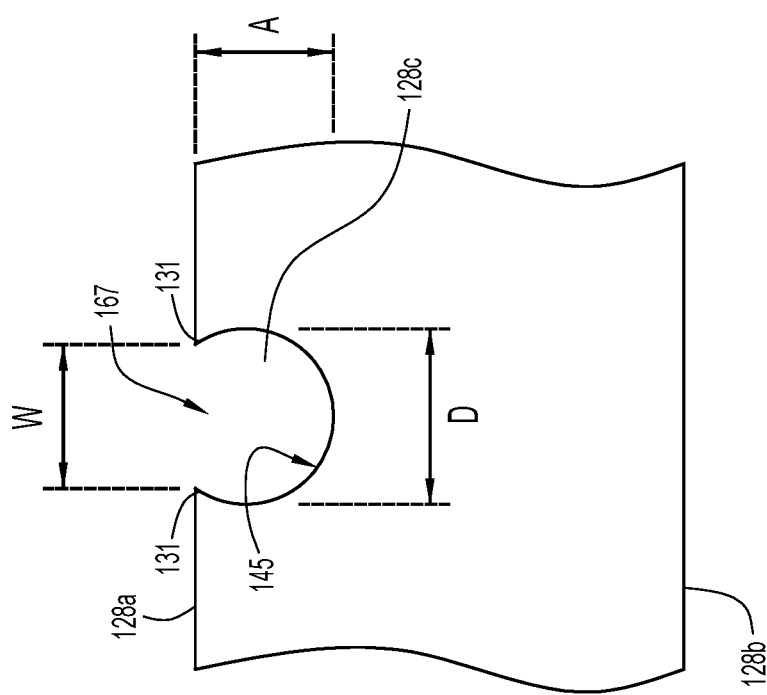

As noted above, according to some implementations the recesses 128*c* in the flexible substrate 128 are structured to hold the radially emitting fiber 127 to the flexible substrate 128 without the need of an adhesive. FIG. 8B illustrates a cross-sectional view of a portion of the flexible substrate 128 that shows a configuration of a recess 128*c* that is capable by itself to hold the radially emitting fiber 127 inside the front face 128*a* of the flexible substrate 128 prior to the liner 129 being formed over the substrate 128. In the implementation of FIG. 8B, the recess 128*c* comprises a semi-circular wall 145 that spans greater than 180 degrees and less than 360 degrees so that the recess opening 167 at the inner face 128*a* has a width W that is smaller than the diameter of the radially emitting fiber 127. As shown in FIG. 8B, such a construction results in the formation of flexible lips 131 located on both sides of the opening.

Figure 10B:
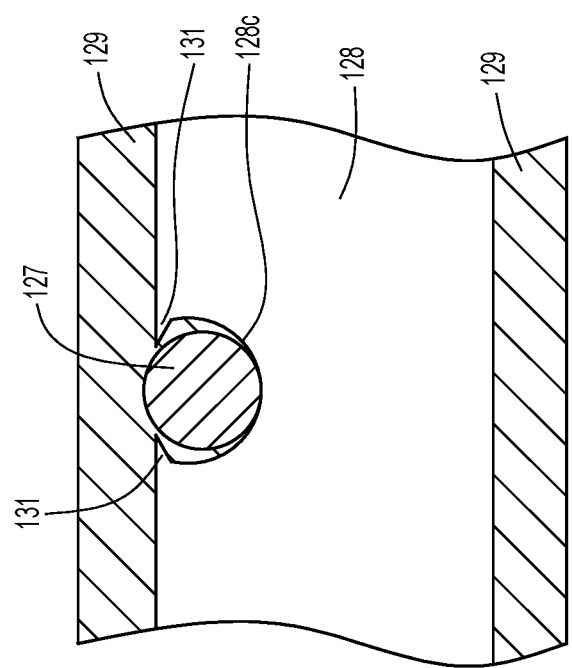
Figure 10C:
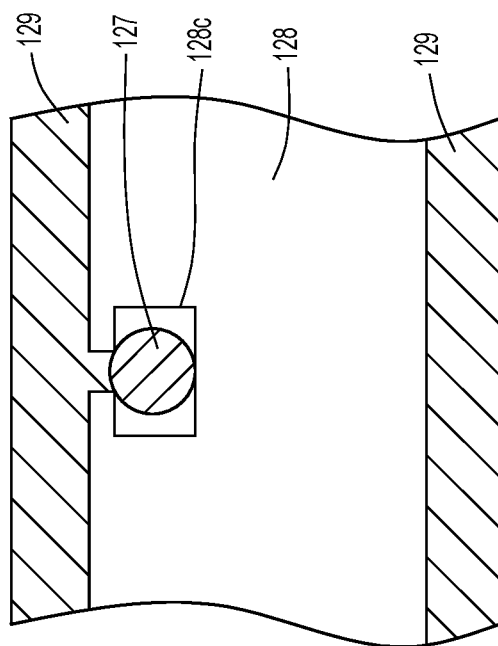
Figure 10D:
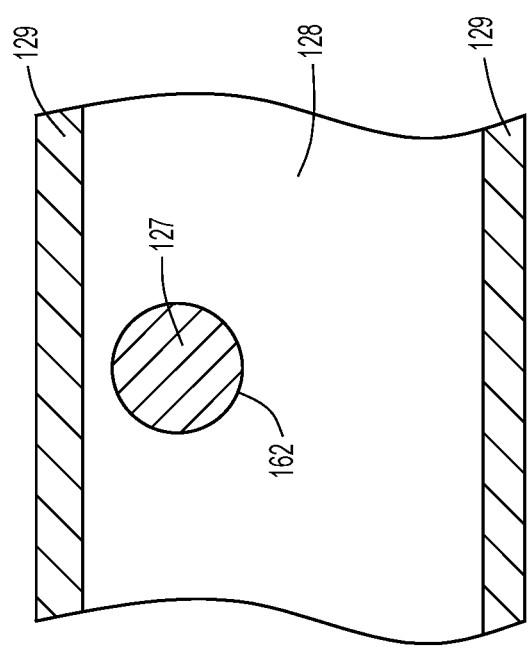

According to some implementations the flexible substrate 128 is formed of a material that enables the lip portions 131 of the wall that form the recesses 128*c* to flex inward sufficiently to allow passage of the radially emitting fiber 127 into the recess when a force is applied along a length of the fiber. The recess 128*c* is configured such that upon the radially emitting fiber 127 being positioned inside the recess, the lips 131 flex outward as shown in FIG. 10B to lock the fiber inside the recess without the need of an adhesive or other fixation means. According to such an implementation the radially emitting fiber 127 can therefore be considered to be snapped into the recess 128*c*. According to some implementations the height dimension H of the recess 128*c* is less than or equal to the diameter of the radially emitting fiber 127. According to such an implementation the flexible substrate 128 is preferably made of a material that is transparent to the bacterial disinfecting light emitted by the radially emitting fiber 127 so that the disinfecting light may pass through the lip regions 131. According to one implementation the diameter D of the circular portion of the recess 128c and the depth A of the recess are each sufficiently greater than the diameter of the radially emitting fiber 127 to enable an axial freedom of movement of the fiber inside the recess to enable it to be threaded through the recess by a pushing or pulling of the fiber through the recess. According to implementations wherein the radially emitting fiber 127 is threaded into the meandering recess 128c, the recess opening 167 at the inner face 128a of the substrate 128 provides visualization and access to the fiber to facilitate an easy and proper placement of the fiber along the length of the recess.

Figure 8C:
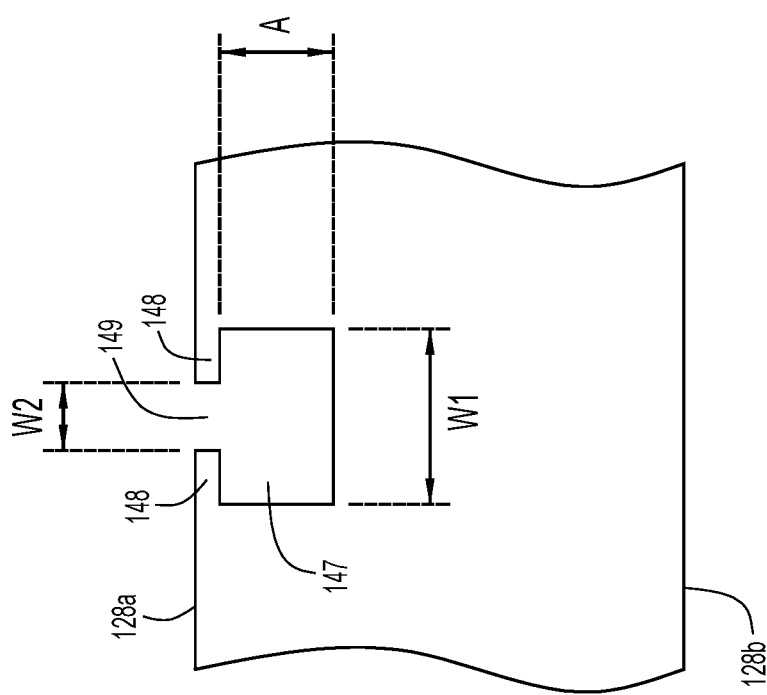

It is important to note that the cross-sectional shape of the recess 128c need not be semi-circular. For example, as shown in FIG. 8C the recess may comprise an inner cavity 147 having a rectangular shape that has a width W1 and depth A that are each equal to or greater than the diameter dimension of the radially emitting fiber 127. A through opening 149 extends from the front face 128a of the substrate 128 into the cavity 147 and is delimited by the side walls of lips 148 that are configured to hold the radially emitting fiber 127 inside the cavity 147. The opening 149 has a width W2 dimension that is less than the diameter dimension of the radially emitting fiber 127. As with the lips 131 of the implementation of FIG. 8B, the lips 148 may be endowed with the ability to flex inward and then outward to facilitate a side loading of the radially emitting fiber 127 into the cavity 147.

According to some implementations the radially emitting fiber 127 and the recesses 128c are arranged in a meandering pattern in a manner that protects the radially emitting fiber from being overstressed to the point of breaking when the lip guard is flexed. According to some implementations, the flexible substrate 128 and/or liner 129 is sufficiently rigid to prevent a flexing of the lip guard 124 beyond an amount that would result in a breakage of the radially emitting fiber 127.

Figure 8D:
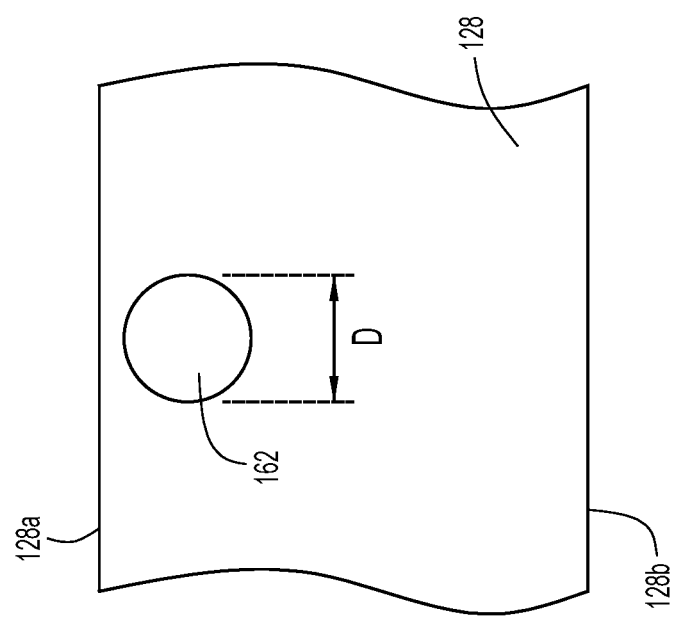

As shown in FIG. 8D, according to some implementations the substrate 128 comprises an internal channel 162 that is configured to receive and house the radially emitting fiber 127. According to one implementation, the diameter D of the channel 162 is sufficiently greater than the diameter of the radially emitting fiber 127 such that the fiber possesses axial and/or radially freedom of movement inside the channel. By being fully surrounded by the walls of the channel 162, freedom of movement of the radially emitting fiber 127 is not affected when the liner 129 is injection molded over the substrate 128. The freedom of movement of the radially emitting fiber 127 protects against its breakage when the lip guard is flexed or otherwise bent during use.

In use, the lip guard may periodically be manipulated by a clinician. This manipulation can result in a bending of the lip guard and of the radially emitting fiber 127 disposed therein. This bending may induce bending and tensile stresses in the optical fiber particularly when the radially emitting fiber 127 is fixed inside the lip guard 124 without axial and/or radial freedom of movement. According to some implementations the lip guard 124 is constructed to limit or prevent a bending of the radially emitting fiber 127 beyond a minimum bending radius of the radially emitting fiber 127. The minimum bending radius may be that established by a manufacturer of the fiber 127. The minimum bending radius may be associated with a function limit or a breaking limit of the optical fiber. A functional minimum bending radius may be specified by the manufacturer of the optical fiber to denote a bending radius of the optical fiber beyond which the optical fiber is unable to properly function. A breakage minimum bending radius may be specified by the manufacturer of the optical fiber to denote a bending radius beyond which a breaking of the core and/or cladding occurs. Alternatively, the functional minimum bending radius may simply be considered to be an actual bending radius of the radially emitting fiber 127 beyond which the optical fiber is unable to properly function and the breakage minimum bending radius may be considered the actual bending radius of the radially emitting fiber 127 beyond which a breaking of the core and/or cladding occurs. The term "minimum bending radius" as used herein refers to any one of the aforestated definitions. In conjunction with or independent from the material selection, the thickness and geometry of the various components of the lip guard 124 may be selected to achieve, or assist in achieving a rigidity of the lip guard sufficient to inhibit a bending of the radially emitting fiber 127 beyond its minimum bending radius.

According to some implementations the lip guard 124 is 1) constructed so that the radially emitting fiber 127 is able to slide within the recesses 128c or channels 162, and/or 2) constructed to limit or prevent the radially emitting fiber 127 from bending beyond its minimum bending radius.

Figure 7A:
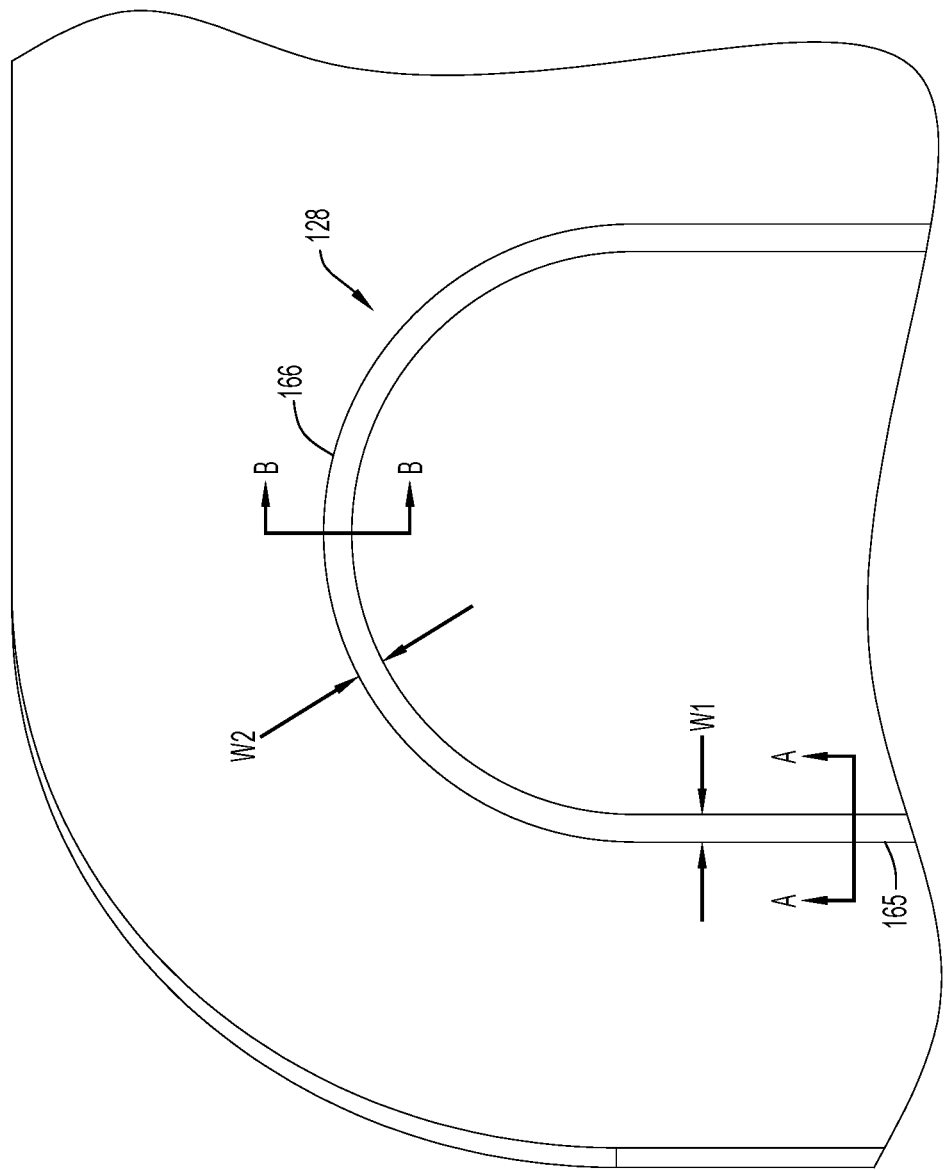
FIG. 7A shows a top view of a lip guard substrate having formed therein a recess of uniform cross-section.
Figure 7B:
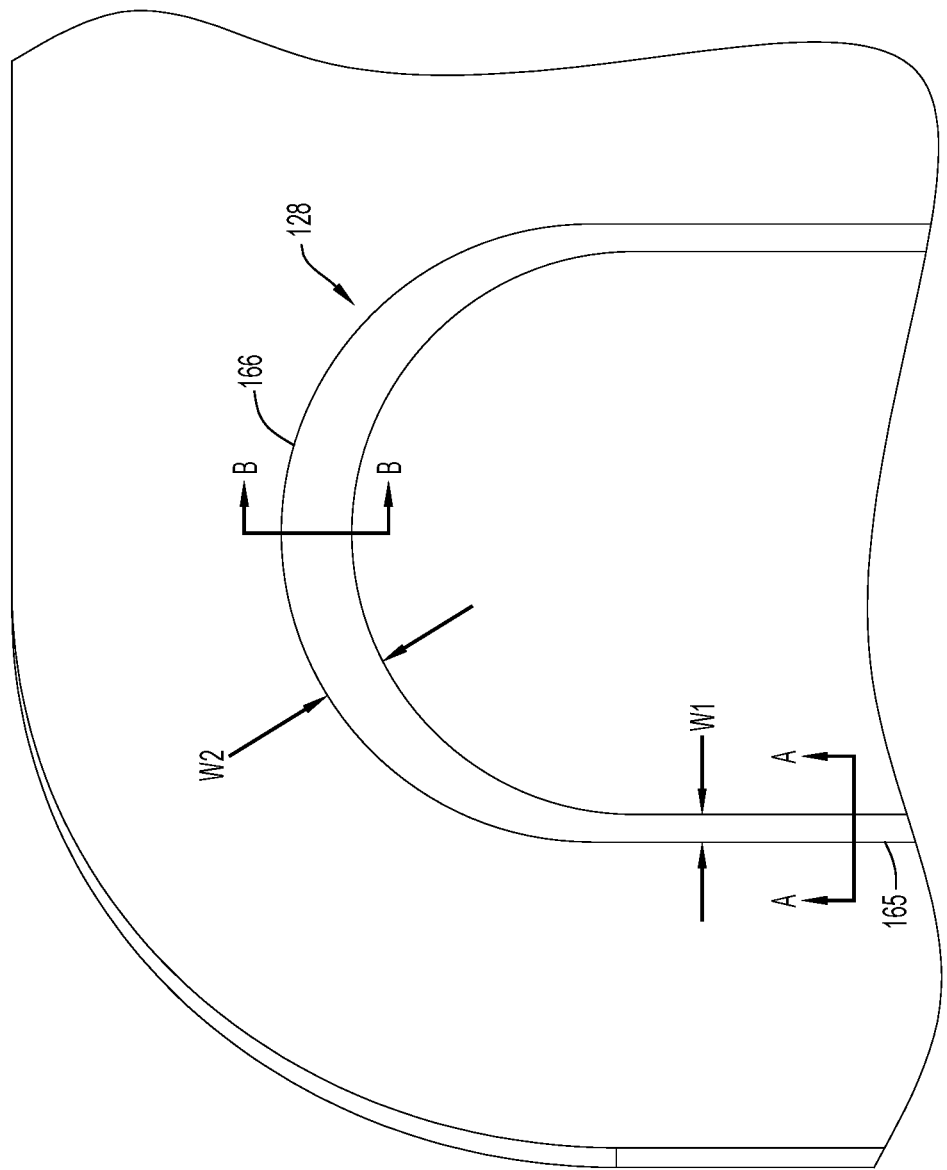
FIG. 7B shows a top view of a lip guard substrate having formed therein a recess of varying cross-section.

As shown in FIGS. 7A and 7B, according to some implementations the recesses 128 formed in the inner face 128a of the substrate 128 include both straight sections 165 and bend sections 166. As shown in FIG. 7A, according to some implementations the width dimension W1 of the straight sections 165 and the width dimension W2 of the bend sections are the same, or substantially the same. As shown in FIG. 7B, according to some implementations the widest width dimension W1 of the straight sections 165 is less than the width dimension W2 of the bend sections. According to some implementations the recesses 128c in the straight sections 165 differ from those on the bend sections 166. For example, according to one implementation the recesses in the straight sections have a configuration like that of FIG. 8B or FIG. 8C while the recesses of the bend sections 166 have a configuration like that of FIG. 8A.

Figure 9A:
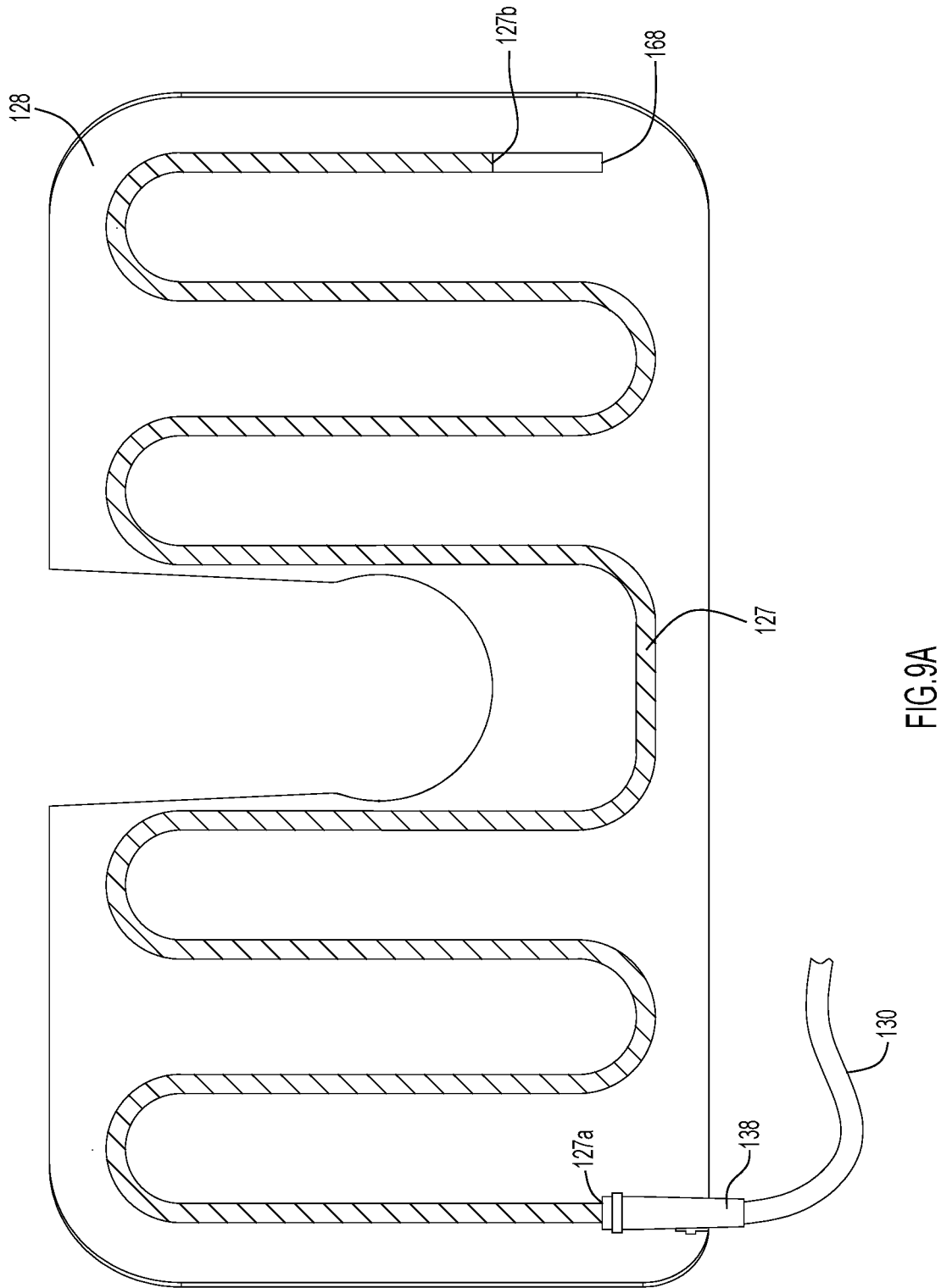
FIGS. 9A-C show top views of lip guard substrates having housed in recesses formed therein a radially emitting fiber.
Figure 9B:
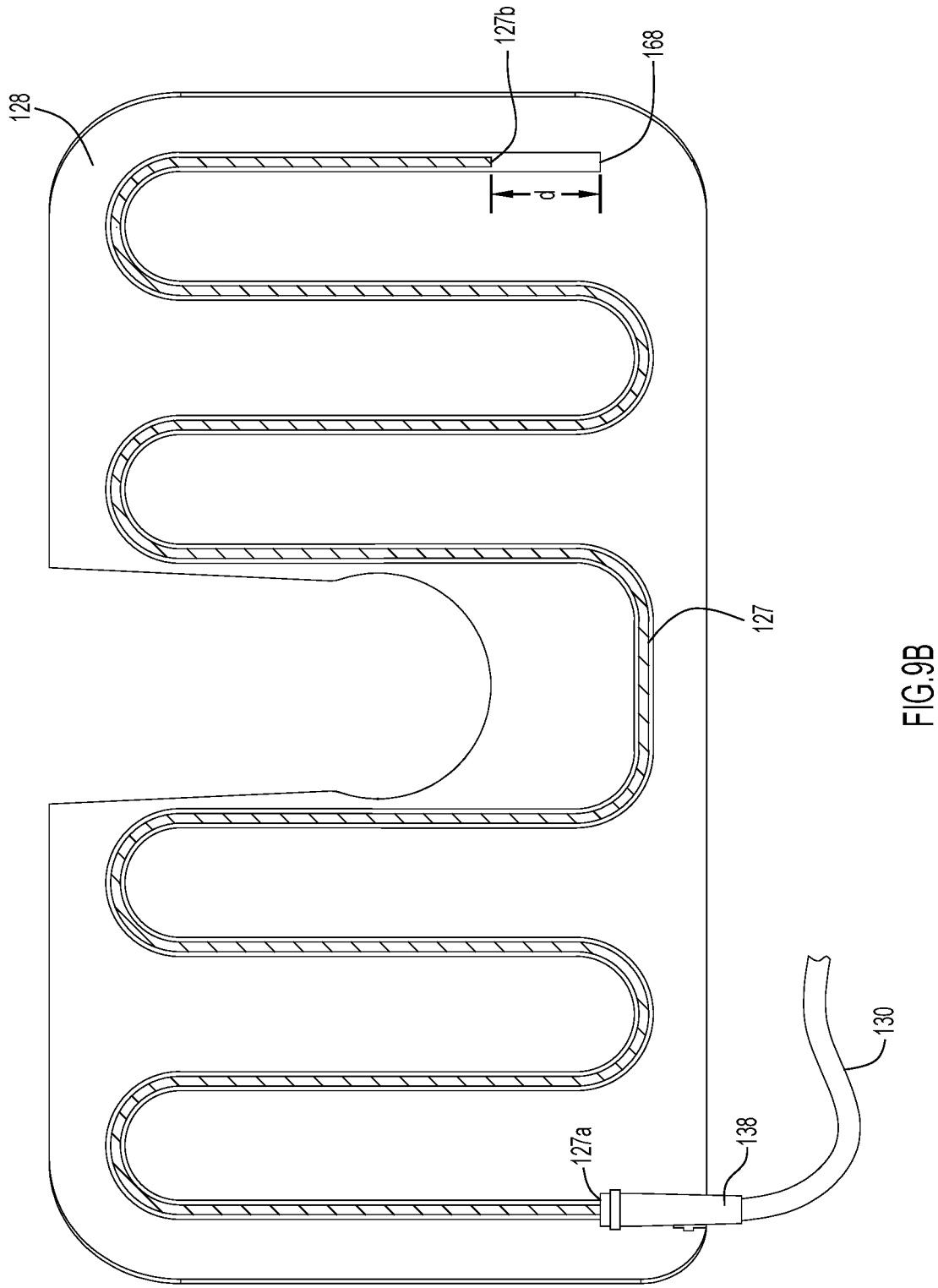
Figure 9C:
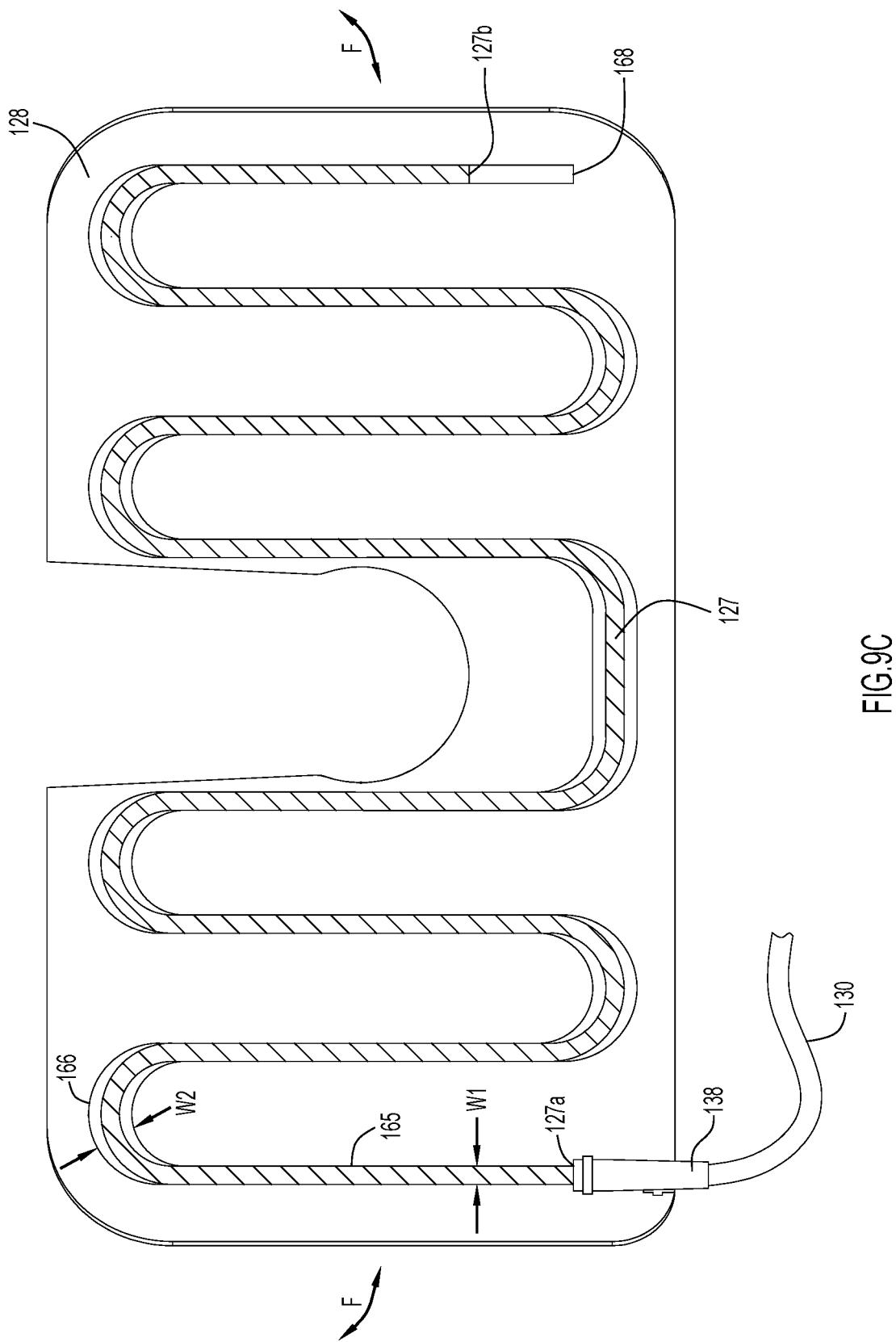

FIGS. 9A-C show implementations of lip guard subassemblies comprising a radially emitting fiber 127 positioned within a meandering recess 128c formed in the inner face 128a of the substrate 128. In the implementation of FIG. 9A, the radially emitting fiber 127 occupies the entirety, or substantially the entirety, of a recess 128 with the recess having substantially the same width along its length. According to some implementations the wall(s) of the recess and/or the outer surface of the radially emitting fiber 127 is provided with a lubricous coating that enables the fiber to slide within the recess. To facilitate such a sliding, the distal end 127b of the fiber 127 is positioned a distal "d" away from the distal end 168 of the recess. In the implementation of FIG. 9B the radially emitting fiber 127 occupies less than the entirety of the recess 128 with the recess having substantially the same width along its length. According to the implementation of FIG. 9B, the radially emitting fiber 127 has at least an axial freedom of movement that allows a sliding of the fiber inside the recess when the lip guard is flexed. To facilitate such a sliding, the distal end 127b of the fiber 127 is positioned a distal "d" away from the distal end 168 of the recess. In the implementation of FIG. 9C the bend sections 166 of the recess have a width W2 that is greater than the width W1 of the straight sections of the recess. As shown in FIG. 9C, according to one implementation the diameter of the radially emitting fiber 127 is less than the width W2 and is substantially equal to the width W1. Moreover, the portions of the radially emitting fiber located inside the bend sections 166 of the recess 128 are provided with slack. That is, the portions of the radially emitting fiber located inside the bends 166 are not held taut inside the bends. Because flexing of the substrate 128 will generally occur in the directions F shown in FIG. 9C, a bending of the radially emitting fiber 127 will predominately occur in the bend regions of the fiber. The provision of slack in the fiber inside the bend regions 166 of the recess 128 safeguards against undue tensile and/or bending stresses being applied to the fiber when the lip guard is bent as a result of slack being taken up during the bending. In each of the implementations of FIGS. 9A-C a proximal end 127a of the radially emitting fiber is connected to a distal end of a transport fiber 130 inside a strain relief member 138. Thus, according to some implementations the proximal end 127a of the radially emitting fiber 127 is fixed with respect to the flexible substrate 128 while the distal end 127b of the fiber is free to move in the gap existing between it and the distal end 168 of the recess 128.

FIGS. 10A-D respectively show the flexible substrate configurations of FIGS. 8A-D with the radially emitting fiber 127 residing in the respective recesses or channel and with the liner 129 formed over the front face 128a and back face 128b of the flexible substrate 128.

According to some implementations all or a portion of the inner face 128a of the flexible substrate 128 is provided with a light reflective coating or film, the coating or film being configured to direct light emitted by the radially emitting fiber 127 in a direction toward the front face 129a of the liner 129. A light reflective coating may be, for example, a light reflective paint interposed between the radially emitting fiber 127 and the flexible substrate 128. A light reflective film may be, for example, in the form of a light reflective metallic foil interposed between the radially emitting fiber 127 and the flexible substrate 128. According to some implementations, only all or a portion of the inner wall of the recesses 128c occupied by the radially emitting fiber 127 are provided with the light reflective coating or film.

FIG. 11 is an exploded perspective view of a lip guard 124 according to another implementation. The lip guard is similar in construction to that depicted in FIG. 6A and further includes a light reflector 134 abutting or applied to the back face 128b of the flexible substrate 128, and an optical diffuser 135 interposed between the radially emitting fiber 127 and the liner 129. According to another implementation the lip guard 124 includes the light reflector 134 and not the optical diffuser 135. According to another implementation the lip guard 124 includes the optical diffuser 135 and not the light reflector 134. In accordance with the latter, all or a portion (e.g. inner wall of recesses 128c) of the front face 128 may be provided with a light reflective coating or light reflective film as discussed above.

In the implementation of FIG. 11 the flexible substrate 128 is made of a material that is transparent to light at least in the visible spectrum. This enables light emitted by the radially emitting fiber 127 to pass through the back face 128b of the substrate 128 to impinge upon the front face 134a of the light reflector 134. The parts of the lip guard may be assembled by the use of adhesives and/or by injection molding processes like discussed above. In implementations wherein the front face 128a of the flexible substrate 128 comprises recesses 128c for housing the radially emitting fiber 127, the recesses 128c may take any of a variety of forms include the examples discussed above in conjunction with FIGS. 8A-D.

According to one implementation the light reflector 134 comprises a light reflective coating such as a light reflective paint or other reflective substance that is applied to the back face of the flexible substrate 128. The light reflector 134 may also comprise a light reflective foil, such as, for example, a metallic foil. The light reflector 134 may also comprise a metal sheet having a light reflective inner face 134a abutting the back face 128b of the substrate 128. According to some implementations the light reflector 134 is selectively applied to or shaped to cover or abut the back face 128b of the substrate 128 only in the vicinity located behind the meandering radially emitting fiber 127.

The lip guard of FIG. 11 may be assembled, for example, by the following methods. After a placement of the light reflector 134 (e.g. reflective foil, metal sheet, etc.) inside a mold, the material used to form the flexible substrate 128 is injection molded to envelope both the front face 134a and back face 134b of the light reflector 134. During this injection molding step the recesses 128c are also formed in the front face 128a of the flexible substrate 128. According to one implementation, the recesses 128c are constructed as described above to permit the radially emitting fiber 127 to be snapped into the recesses. According to such an implementation, after the flexible substrate 128 is formed the radially emitting fiber 127 is secured to the flexible substrate by being snapped into the recesses 128c. According to the other implementations the radially emitting fiber 127 is adhesively secured to the front face 128a of the substrate 128. According to such implementations the radially emitting fiber 127 may or may not be adhesively fixed inside a recess formed in the front face 128a of the substrate 128 In any event, upon the radially emitting fiber 127 being secured to the flexible substrate 128, a subassembly comprising the light reflector 134 enveloped in the flexible substrate 128 and the radially emitting fiber 127 secured to the front face 128a of the flexible substrate is produced. In implementations that do not incorporate the optical diffuser 135, the material from which the liner 129 is made is injection molded to envelop or substantially envelop the aforestated subassembly. In implementations that do incorporate the optical diffuser 135, the back face 135b of the optical diffuser is positioned over the radially emitting fiber 127 and the material from which the liner 129 is made is injection molded around the subassembly and front face 135a of the optical diffuser 135. An advantage of using the optical diffuser 135 is that it more uniformly distributes the light emitted by the radially emitting fiber 127 into that part of the liner 129 that is adapted to face the mouth area of the patient.

According to other implementations, the lip guard of FIG. 11 may be assembled by applying a light reflecting coating (e.g. light reflecting paint) or a light reflecting film (e.g. a light reflecting foil) to the back face 128b of the flexible substrate 128 after the formation of the flexible substrate. In implementations that do not incorporate the optical diffuser 135, upon the radially emitting fiber 127 being secured to or within the front face 128a, the subassembly including the substrate 128, light reflective coating or film and the radially emitting fiber 127 are placed in a mold and the material used to produce the liner 129 is injection molded to envelope or substantially envelope the subassembly. In implementations that do incorporate an optical diffuser 135, the back face 135b of the optical diffuser is positioned over the radially emitting fiber 127 and the material from which the liner 129 is made is injection molded over the subassembly and front face 135a of the optical diffuser 135.

Figure 12A:
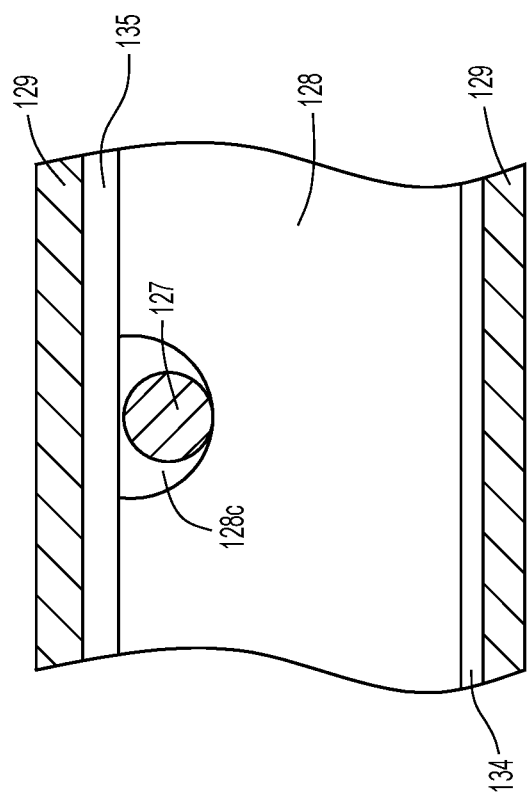
FIGS. 12A and 12B show cross-sectional views of the lip guard of FIG. 11 assembled according to some implementations.
Figure 12B:
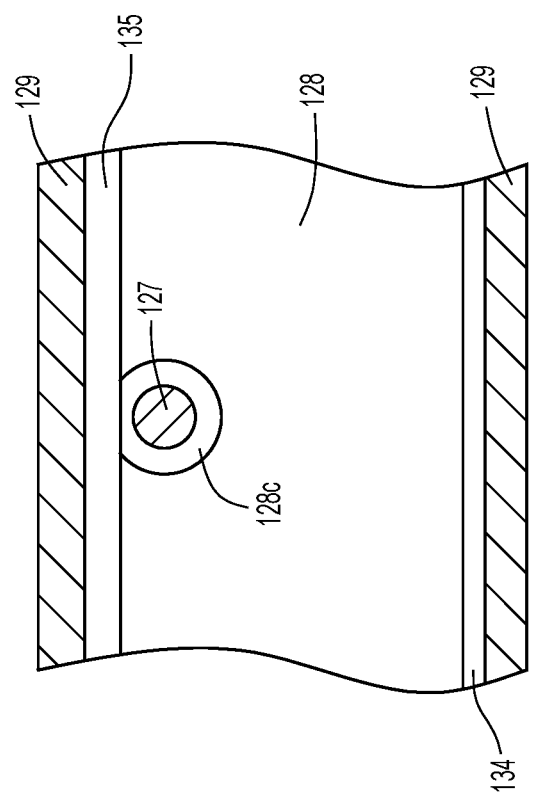

FIGS. 12A and 12B are cross-sectional views of lip guard portions according to some implementations. In the implementation of FIG. 12A, a U-shaped recess 128c is formed in the front face 128a of the flexible substrate 128 and has disposed therein a radially emitting fiber 127. The radially emitting fiber 127 has a diameter that is less than the diameter of the U-shaped recess 128c so that a space exists between the radially emitting fiber and the front face 128a of the substrate when the fiber is assembled in the recess. After the radially emitting fiber 127 is positioned in the recess 128c, the light diffuser 135 is positioned on the front face of the substrate 128 to form a closed housing wherein the radially emitting fiber 127 is housed. The configuration of the closed housing is such that the radially emitting fiber has freedom of movement in the axial direction of the fiber and/or in the radial direction of the fiber. In the implementation of FIG. 12A the back face 128b of the substrate 128 contains a light reflective coating or film 134 and the liner 129 covers both the front face 135a of the light diffuser 135 and the back face of the reflective coating or film 135.

The implementation of FIG. 12B has a similar construction to that of FIG. 12A with the exception that the recess 128c formed in the front face 128a of the substrate 128 has a form consistent with that of FIG. 8B. Like the implementation of FIG. 12A, the light diffuser 125 is positioned on the front face 128a of the substrate 128 so that a closed housing wherein the radially emitting fiber 127 is housed. The configuration of the closed housing is such that the radially emitting fiber has freedom of movement in the axial direction of the fiber and/or in the radial direction of the fiber. In the implementation of FIG. 12B the back face 128b of the substrate 128 contains a light reflective coating or film 134 and the liner 129 covers both the front face 135a of the light diffuser 135 and the back face of the reflective coating or film 135.

As explained above, providing a freedom of movement of the radially emitting fiber 127 inside the recess 128 prevents against breakage of the fiber when the lip guard is bent or otherwise deformed.

In regard to the implementations of FIGS. 11, 12A and 12B, it is important to note that the optical diffuser 135 may be substituted with a light transparent member that is not a light diffuser. In such an implementation the function of the light transparent member is to lie over the front face 128a of the substrate 128 to cause a closing of the recess 128c. The closing of the recess prevents the material that forms the liner 129 from entering the recess wherein resides the radially emitting fiber 127. As such, a freedom of movement of the fiber inside the recess is maintained after the injection molding of the liner.

In regard to each of the recesses disclosed or contemplated herein that house a radially emitting fiber, an index matching gel may be interposed between the radially emitting fiber and the inner wall of the recess to facilitate a coupling of light from the fiber into the material from which the lip guard is made. According to some implementations the index matching gel also allows the radially emitting fiber to more easily slide within the recess in comparison to the fiber's ability to slide in the recess absent the index matching gel. According to some implementations the radially emitting fiber comprises a core that is surrounded by a cladding with the cladding having a first refractive index and the inner wall of the recess comprising a material having a second refractive index, the index matching gel having a third refractive index that is between the first refractive index and the second refractive index.

In implementations in which a light reflector 134 is utilized, the substrate 128 is endowed with a thickness that provides a separation distance between the backside of the radially emitting fiber 127 and the front face 134a of the light reflector 134. According to one implementation the separation distance is between 1 to 5 times the diameter dimension of the radially emitting fiber. Maintaining such a separation distance between the backside of the radially emitting fiber 127 and the light reflector 134 results in a greater amount of light emitted from the backside of the radially emitting fiber being reflected in a forward direction toward the front face 129a of the liner 129.

Figure 13:
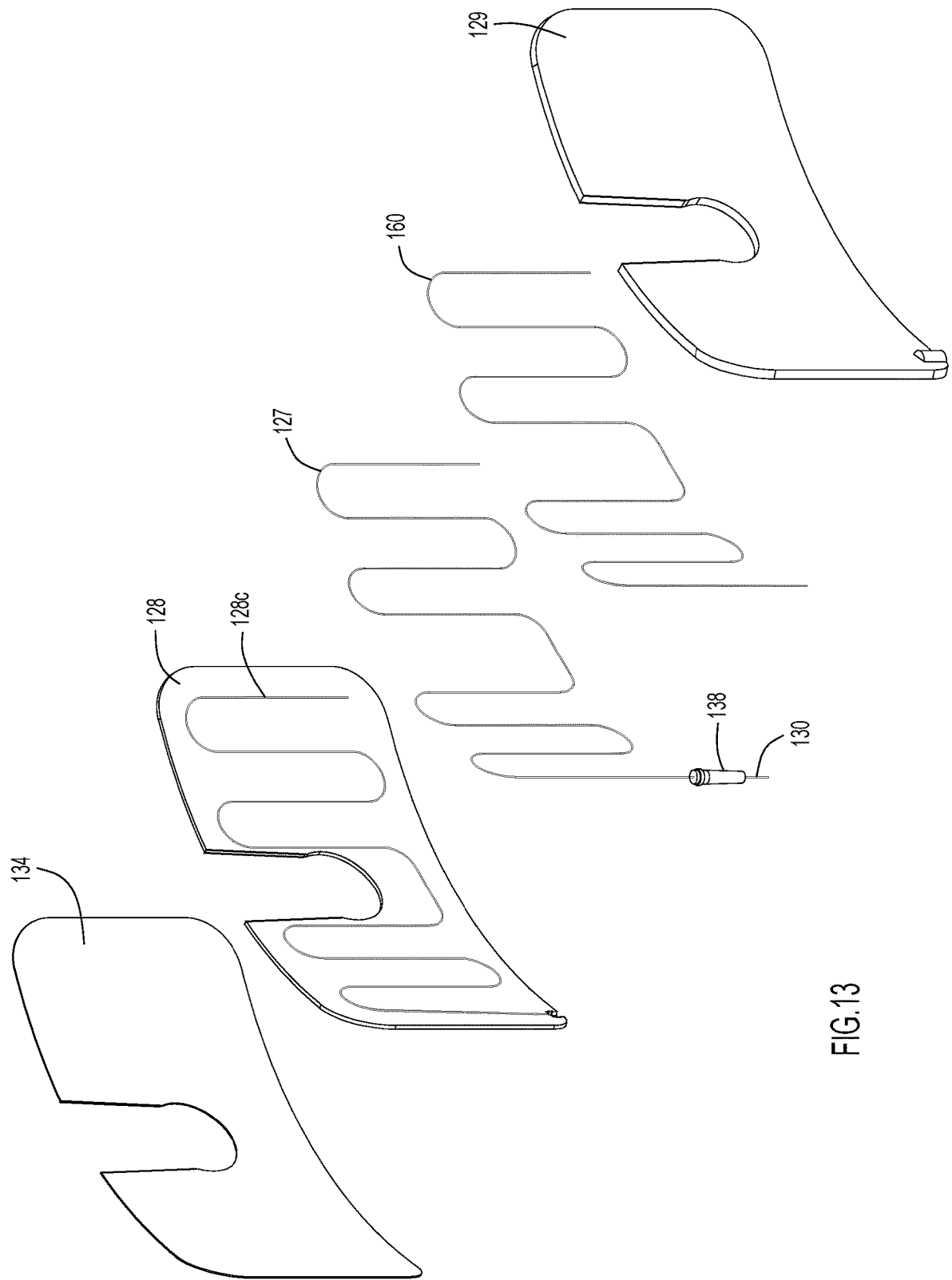
FIG. 13 is an exploded perspective view of a lip guard according to yet another implementation.
Figure 14:
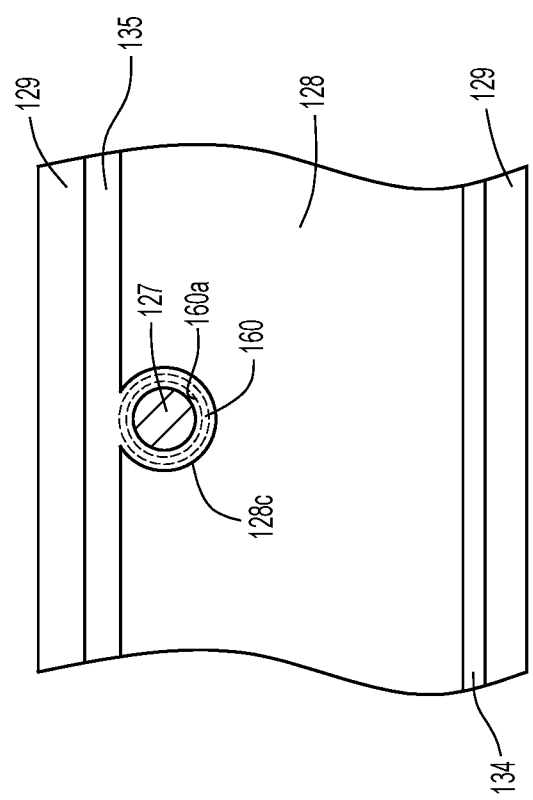
FIG. 14 is a cross-sectional view of the lip guard of FIG. 13 assembled according to one implementation.

FIG. 13 is an exploded perspective view of a lip guard 124 according to another implementation. The lip guard of FIG. 13 is similar to the construction of the lip guard of FIG. 11 and also includes a flexible tubular member 160 configured to house the radially emitting fiber 127. The tubular member 160 is made of a flexible material that is transparent to light at least in the visible spectrum. The tubular member 160 and the radially emitting fiber 127 are sized to permit axial and/or radial movement of the fiber inside the tubular member. To this end, one or both of the length and inside diameter of the tubular member 160 is respectively greater than the length and outer diameter of the radially emitting fiber 127. The implementation of FIG. 13 differs from the implementation of FIG. 11 in that the flexible tubular member 160 itself resides inside the recesses 128c of the substrate 128 with the radially emitting fiber 127 residing inside the tubular member. FIG. 14 illustrates a lip guard cross-section similar to that of FIG. 12B. However, in the implementations of FIG. 14, the radially emitting fiber 127 resides inside a tubular member 160 that is snap fit into the recess 128c. According to some implementations one or both of the inner wall 160a of the tubular member 160 and the outer wall of the radially emitting fiber 127 is provided with a light transparent lubricious coating to facilitate a sliding of the fiber inside the tubular member 160. According to some implementations a gap between the outer surface of the radially emitting fiber 127 and the inner wall 160a of the tubular member 160 is filled with an index matching gel that facilitates a coupling of light between the fiber and the wall of the tubular member. According to some implementations the index matching gel also allows the radially emitting fiber 127 to more easily slide within the lumen of the tubular member 160 in comparison to the fiber's ability to slide in the lumen absent the index matching gel. According to one implementation the radially emitting fiber comprises a core that is surrounded by a cladding with the cladding having a first refractive index and the tubular member 160 comprising a material having a second refractive index, the index matching gel having a third refractive index that is between the first refractive index and the second refractive index.

FIG. 15A is an exploded perspective view of a lip guard 124 according to another implementation. The lip guard includes a flexible substrate 128 in the form of a metal sheet that is fabricated to include protruding clip connectors 136 extending outward from the front face 128a of the metal sheet. Each of the clip connectors 136 is configured to receive therein a portion of the radially emitting fiber 127. According to one implementation each of the clip connectors 136 comprises a tab 136a having formed therein a slot 136b. According to one implementation, the slot 136b has a shape similar to that of the recesses 128c discussed above in conjunction with the description of FIG. 7A. That is, it comprises a semi-circular cavity having an inner wall that spans greater than 180 degrees but less than 360 degrees such that a transvers opening 136c of the slot has a width dimension that is less than the diameter of the semi-circular cavity. According to one implementation lips similar to the lips 137 of FIG. 7A are formed at the transverse opening 136c that are capable of flexing inward and then outward to receive and then retain the radially emitting fiber 127 inside the slot 136. In lieu of or in conjunction with the aforestated lip flexing feature, the walls 136d and 136e on each side of the slot 136 may be made to flex outward in the direction M as shown in FIG. 15B upon the radially emitting fiber 127 being pressed into the transverse opening 136c. According to one implementation the tab 136 and the slot 137 are formed by one or more stamping procedures. According to one example the slots 137 are made by a first stamping step to form a plurality of through holes that pass from the back face 128b of the metal sheet to the front face 128a of the metal sheet. After the slots 137 are made in the metal sheet, the tabs are cut via a second stamping operation and then bent to protrude from the front face 128a as most clearly shown in FIG. 15B.

Figure 15C:
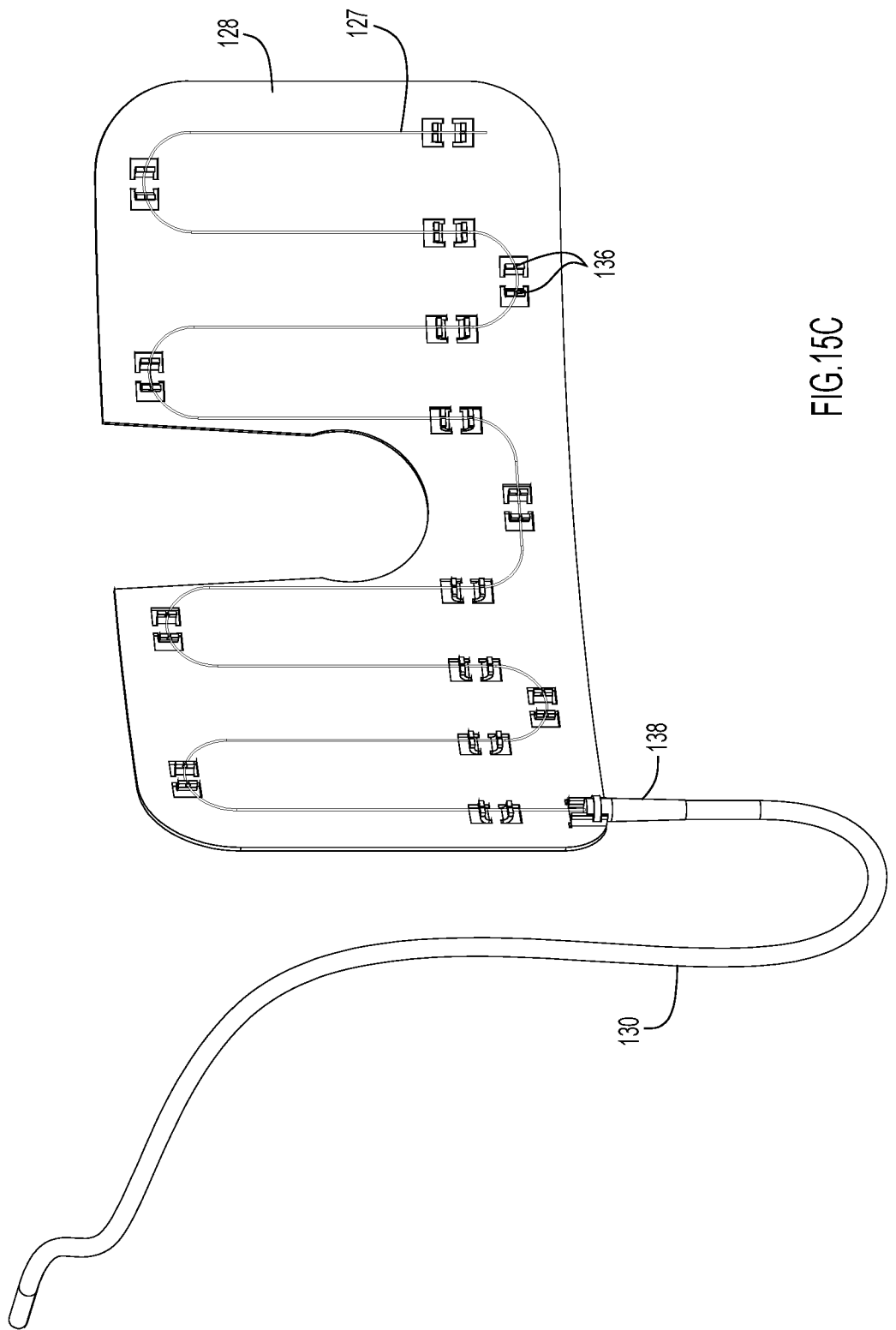
FIG. 15C shows the radially emitting fiber of FIG. 15A attached to the flexible substrate by use of the clip connectors.

As shown in FIG. 15C, according to some implementations the clip connectors 136 are arranged to facilitate a meandering placement of the radially emitting fiber 127 on the metal sheet 128.

As with each of the lip guard assemblies disclosed and contemplated herein, the radially emitting fiber 127 may be connectable to a bacterial disinfecting light source via a transport fiber 130. According to some implementations a strain relief member 138 is provided at or adjacent the juncture of the transport fiber 130 and the radially emitting fiber 127. As shown in FIG. 15B, the metal sheet 127 may possess a strain relief support structure that includes an opening 140 bound on two sides by tabs 141 having formed therein notches 142. As with the clip connectors 136, the tabs, opening and notches may be formed by one or more stamping procedures and thereafter bent to protrude from the front face 128 of the metal sheet as shown in FIG. 9B. According to one implementation the distal end portion of the strain relief 138 includes an annular part 138a that is configured for placement inside the notches 142 of the strain relief support structure.

After the radially emitting fiber 127 is attached to the metal sheet 127, the liner 129 is injection molded over the radially emitting fiber/metal sheet subassembly to partially or totally envelop the subassembly. As explained above, the liner 129 is made of a material that is transparent to light at least in the visible spectrum.

In the foregoing disclosure the substrate 128 and liner 129 are disclosed as being flexible such that when the lip guard 124 is fully assembled it has a degree of flexibility to enable it to at least partially conform to different sizes and shapes of the mouth regions of patients. However, according to other implementations one or both of the substrate 128 and liner 129 may be composed of a rigid material.

With continued reference to FIGS. 15A-C, according to some implementations the front face 128a of the metal sheet 128 is light reflective. According to other implementations all or portions of the front face 128a are provided with a light reflective coating or film. According to one implementation only portions of the front face underlying the radially emitting fiber 127 are provided with the light reflective coating or film. According to one implementation the width of the light reflective coating or film is 1 to 10 times the diameter of the radially emitting fiber 127.

According to some implementations the tabs 136 are constructed such that the radially emitting fiber 127 is suspended above the front face 128a of the metal sheet 128 when the radially emitting fiber is supported in the slots 136c. This advantageously spaces the backside of the radially emitting fiber 127 from the light reflective surface of the metal sheet 128 or of the light reflective coating or film disposed on the front face 128 of the metal sheet. As explained above, maintaining a separation distance between the backside of the radially emitting fiber 127 and the light reflective surface results in a greater amount of light emitted from the backside of the radially emitting fiber being reflected in a forward direction toward the front face 129a of the liner 129. According to some implementations, the separation distance is between 1 to 5 times the diameter dimension of the radially emitting fiber 127.

According to other implementations the radially emitting fiber 127 is not attached to the clip connectors 136 but resides inside a flexible tubular member 160 like that discussed above in conjunction with FIGS. 13 and 14. According to such implementations the tubular member 160 is itself attached to the clip connectors 136. An advantage of such a construction is that allows the radially emitting fiber 127 to be supported on the substrate 128 inside the tubular member with a freedom of movement in the axial direction and/or radial direction of the fiber. According to this latter implementation, the liner 129 is injection molded to envelop the substrate 128 and the tubular member 160 attached thereto.

Figure 16A:
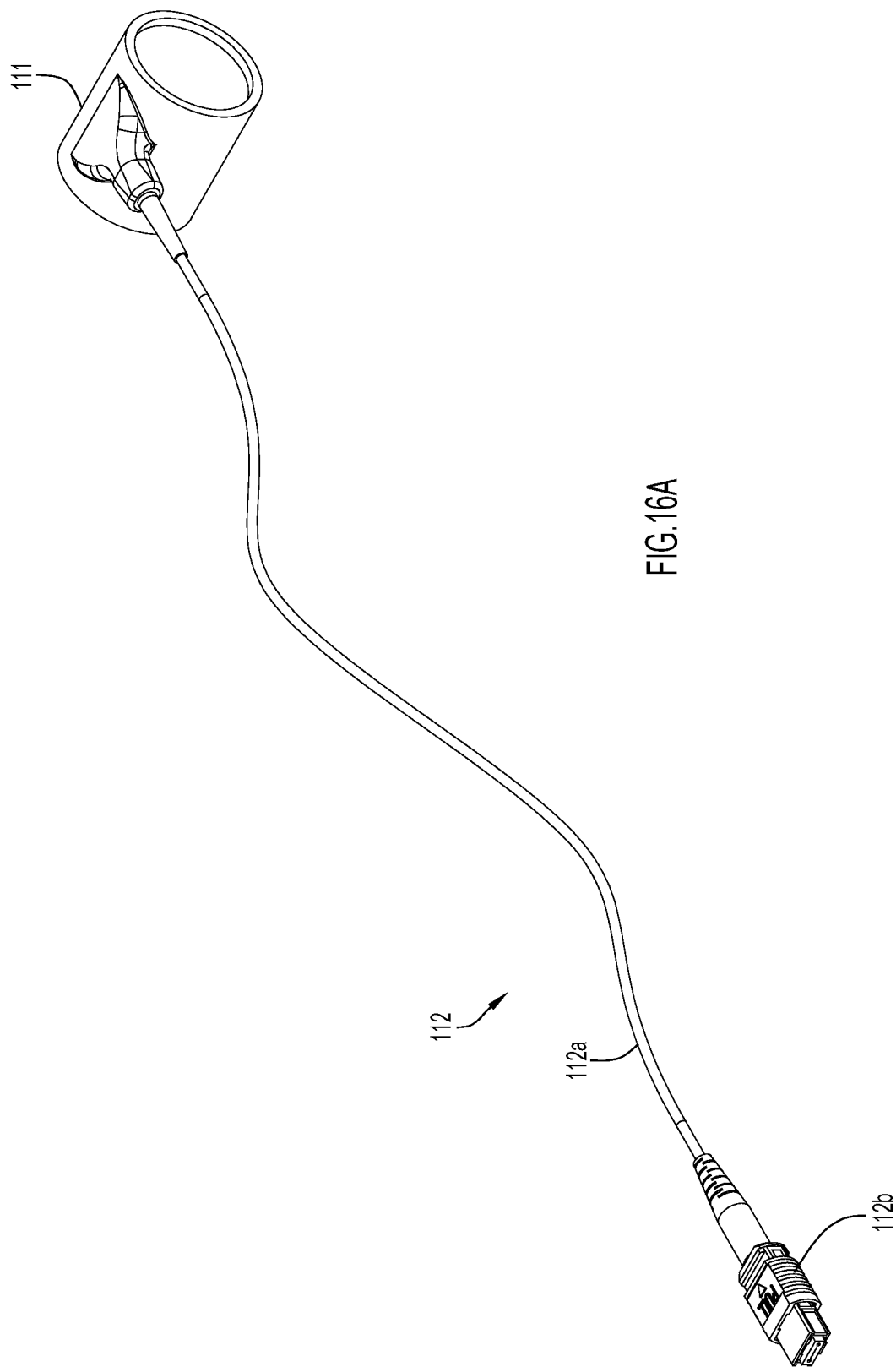
FIG. 16A is a perspective view of an assembled light disinfecting collar according to one implementation.
Figure 16B:
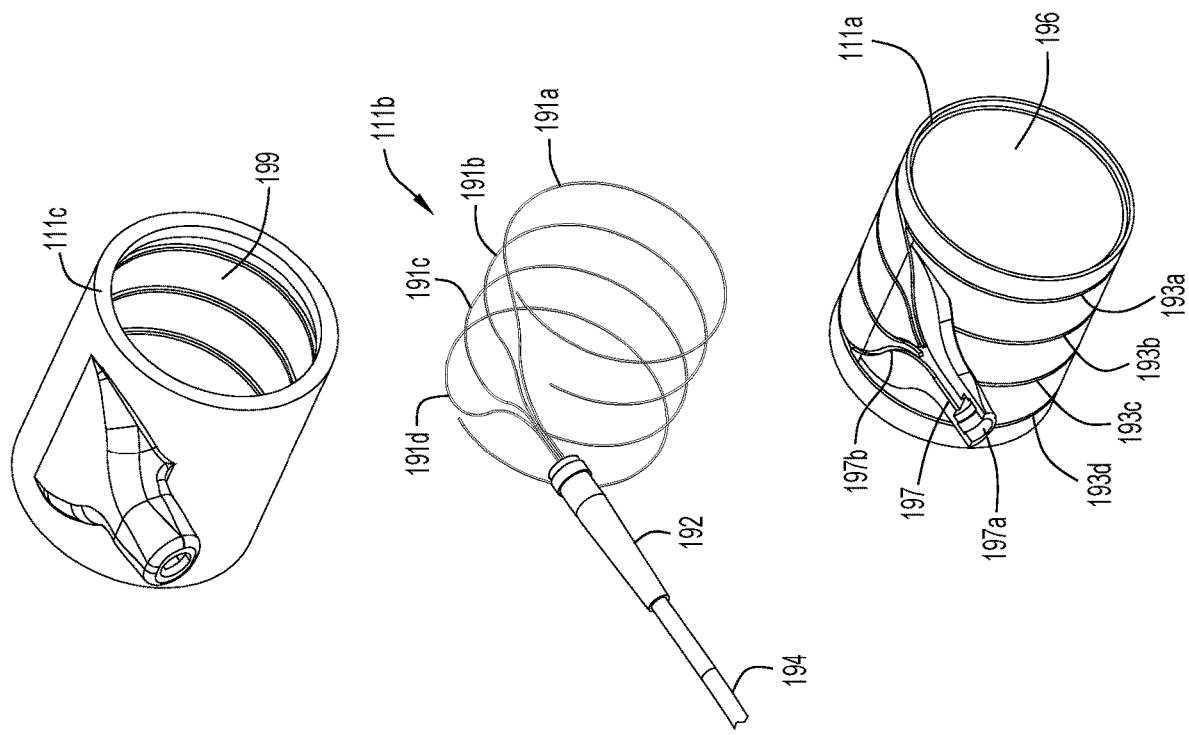
FIG. 16B is an exploded perspective view of the light disinfecting collar of FIG. 16A.

FIG. 16A shows a light disinfecting collar 111 adapted for disinfecting an area of connection between the proximal end portion 101a of the intubation tube 101 and the connector 103 that connects the intubation tube to the ventilator tube set 102. FIG. 16B shows an exploded perspective view of the light disinfecting collar of FIG. 16A.

Figure 17:
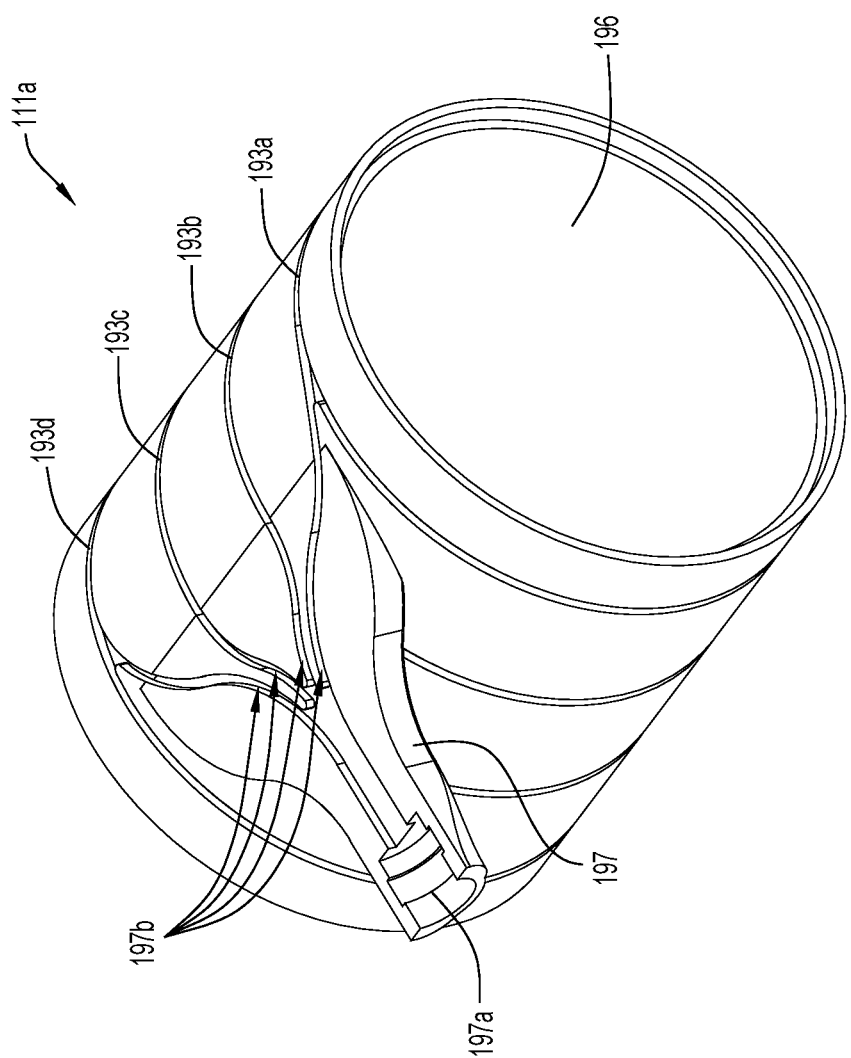
FIG. 17 is an enlarged perspective view of an inner member of the light disinfecting collar shown in FIG. 16A.

As explained above, according to one implementation bacterial disinfecting light is delivered to the light disinfecting collar 111 from a light source via an optical fiber set 112 that includes one or more transport fibers connected to an MPO connector 112a. According to one implementation the optical fiber tube set 112 includes a single transport fiber that is coupled at its distal end (the end opposite the connector 112a) to a single radially emitting fiber. The radially emitting fiber is supported on an inner member 111a that may or may not contain grooves that at least partially house the radially emitting fiber. According to one implementation the radially emitting fiber extends along the entire circumference of the inner member 111a in a coil-like or meandering configuration. In the implementation of FIG. 16B, the disinfecting light assembly 111b includes four transport fibers (located inside a common jacket 194) to which four radially emitting fibers 191a, 191b, 191c and 191d are connected inside a strain relief member 192. In the implementation of FIG. 16B the inner member 111a comprises four grooves 193a, 193b, 193c and 193d that are configured to respectively receive radially emitting fibers 191a, 191b, 191c and 191d. FIG. 17 shows an enlarged view of the inner member 111a. According to the implementation of FIG. 16B, each of the radially emitting fibers extends along the entire circumference or substantially the entire circumference of the inner member 111a. According to some implementations the inner member 111a is formed with a protruding tray 197 having a recess 197a that is configured to support the distal end of the strain relief 192. The protruding tray 197 is also equipped with a set of four diverging channels 197b that provide pathways for the four radially emitting fibers 191a-d into their respective grooves 193a-d. It is important to note that the assembly may include less than or more than four radially emitting fibers. The inner member 111a includes a through opening 196 in which the proximal end portion 101a of the intubation tube 101 and the distal end portion 103b of connector 102 reside when the collar 111 is integrated into the intubation tube system as shown in FIG. 3B.

According to one implementation, a light disinfecting collar subassembly is made by assembling the disinfecting light assembly 111b onto the disinfecting collar 111 such that the distal end of the strain relief 192 is supported in the recess 197a and the radially emitting fibers 191a-d respectively reside in grooves 193a-d. According to some implementations the strain relief 192 and the radially emitting fibers 191a-d are retained on the inner member 111a by use of an adhesive. The inner member 111a is made of a material that is transparent to light at least in the visual spectrum. The material may be, for example, polycarbonate.

The light disinfecting collar 111 may include an outer member 111c that is disposed about the aforementioned subassembly. According to one implementation the outer member 111c is injection molded over the subassembly so that the radially emitting fibers (or fiber) are encased inside the collar 111 as shown in FIG. 16A. According to one implementation a light reflective material or element is interposed between the radially emitting fibers 191a-d and the inside wall 199 of the outer member 111c so that the light emitted by the radially emitting fibers is directed inward toward the through opening 196 of the inner member 111a. According to one implementation the collar 111 is constructed by covering the radially emitting fibers 191a-d with a light reflecting member before the outer member 111c is injection molded over the aforementioned subassembly. According to other implementations a light reflecting member or light reflecting coating may be provided on an outer surface of the outer member 111c. According to such an implementation, the outer member 111c is made of a material that is transparent to light at least in the visual spectrum.

Figure 18A:
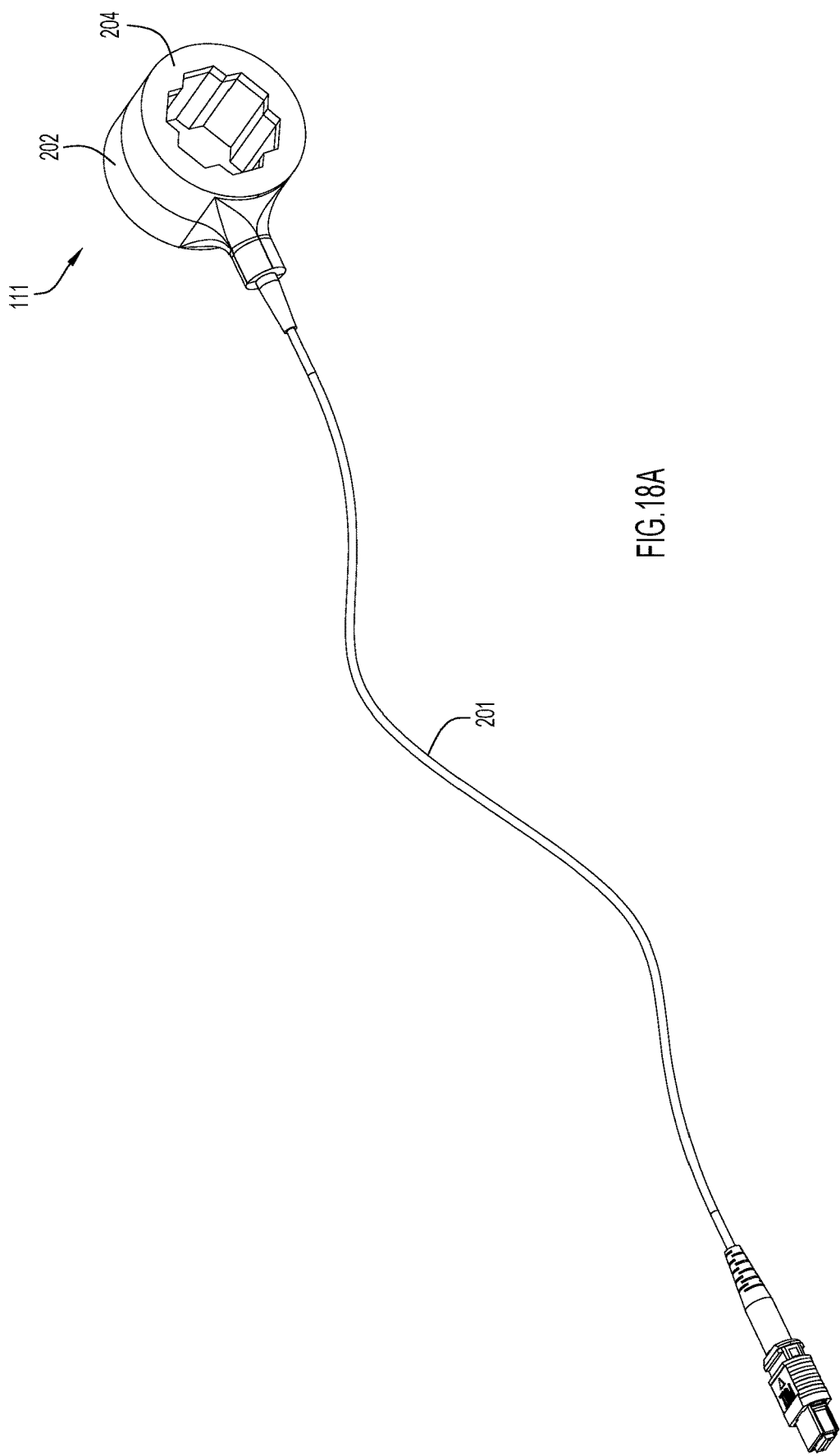
FIG. 18A is a perspective view of a light disinfecting collar according to another implementation.
Figure 18B:
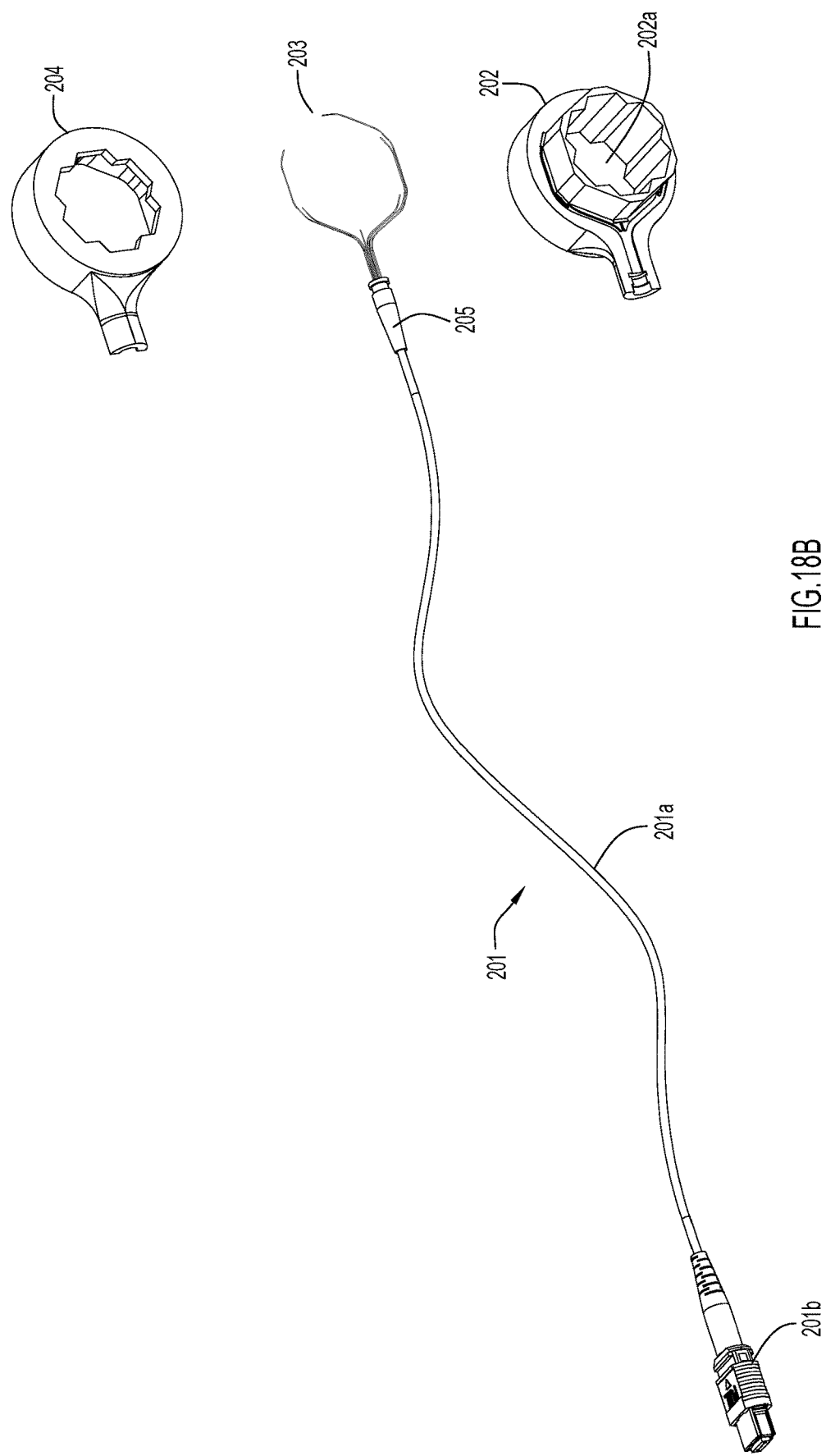
FIG. 18B is an exploded perspective view of the light disinfecting collar of FIG. 18A.

FIG. 18A shows a light disinfecting collar 111 according to another implementation wherein one or more side firing fibers and/or one or more end emitting fibers are used to direct bacterial disinfecting light at a connection location between an intubation tube 101 and an intubation tube set 102. In the following example one end emitting fiber 206 and five side firing fibers 207a-e are utilized. It is appreciated, however, that the disclosure is not limited to such a make-up and may include any of a number of end emitting fibers and side firing fibers. FIG. 18B is an exploded perspective view of the light disinfecting collar assembly of FIG. 18A.

In the context of the embodiment of FIGS. 18A and 18B, a side firing fiber is an optical fiber provided with an angled end face that is oriented to totally internally reflect a light beam out of the side surface of the fiber in a direction transverse to the longitudinal axis thereof. Examples of side firing optical fibers are found in U.S. Pat. Nos. 4,740,047 and 5,772,657.

According to one implementation bacterial disinfecting light is delivered to the light disinfecting collar 111 from a light source via an optical fiber set 201 that includes six optical fibers 206 and 207a-e whose proximal end portions are housed in a common jacket 201a. According to one implementation the proximal ends of the six optical fibers are optically coupled to a six port optical connector 201b. The optical connector 201b is in turn connectable to a bacterial disinfecting light source, such as a laser. The collar assembly 111 includes a first part 202 on which the fibers 206 and 207a-e are supported in a manner that results in light emitted by each of the fibers being directed inward toward a through opening 202a located therein like that shown in FIG. 21. According to one implementation each of the end emitting fiber 206 and side firing fibers 207a-e pass through a strain relief member 205 at their entry point into the first part 202.

Figure 19A:
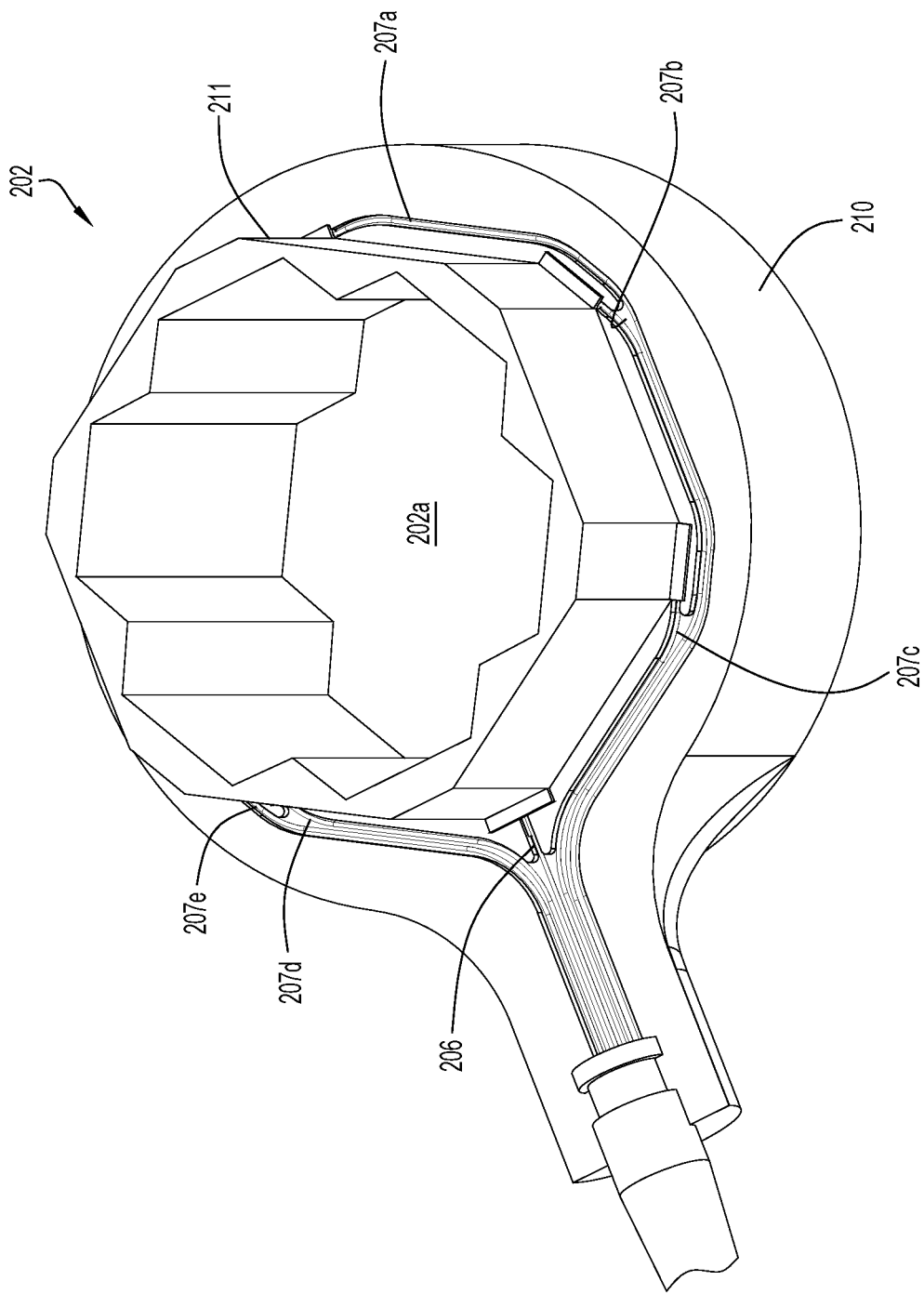
FIGS. 19A-C show various perspective views of a first part of the light disinfecting collar of FIG. 18B.
Figure 19B:
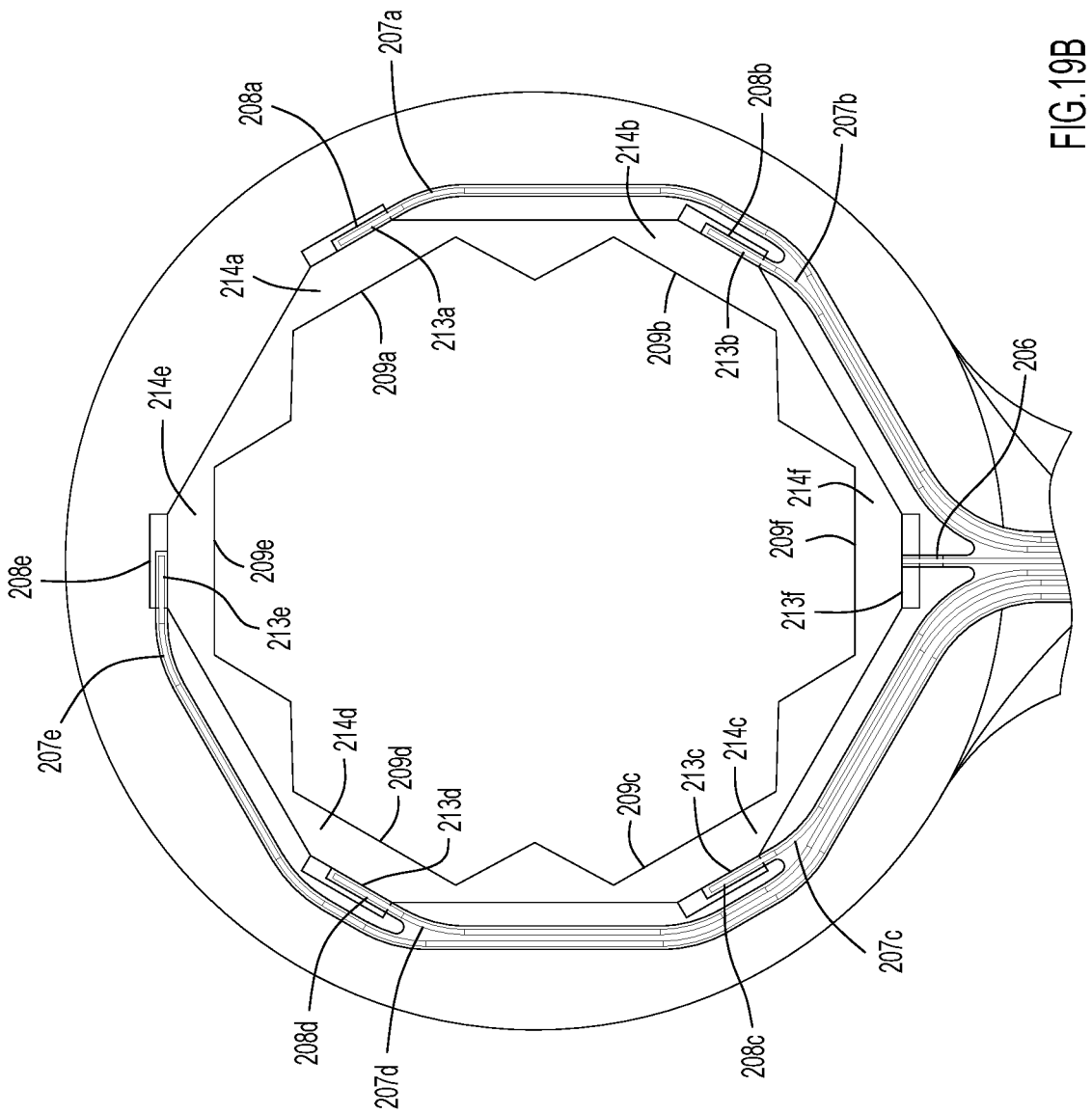
Figure 19C:
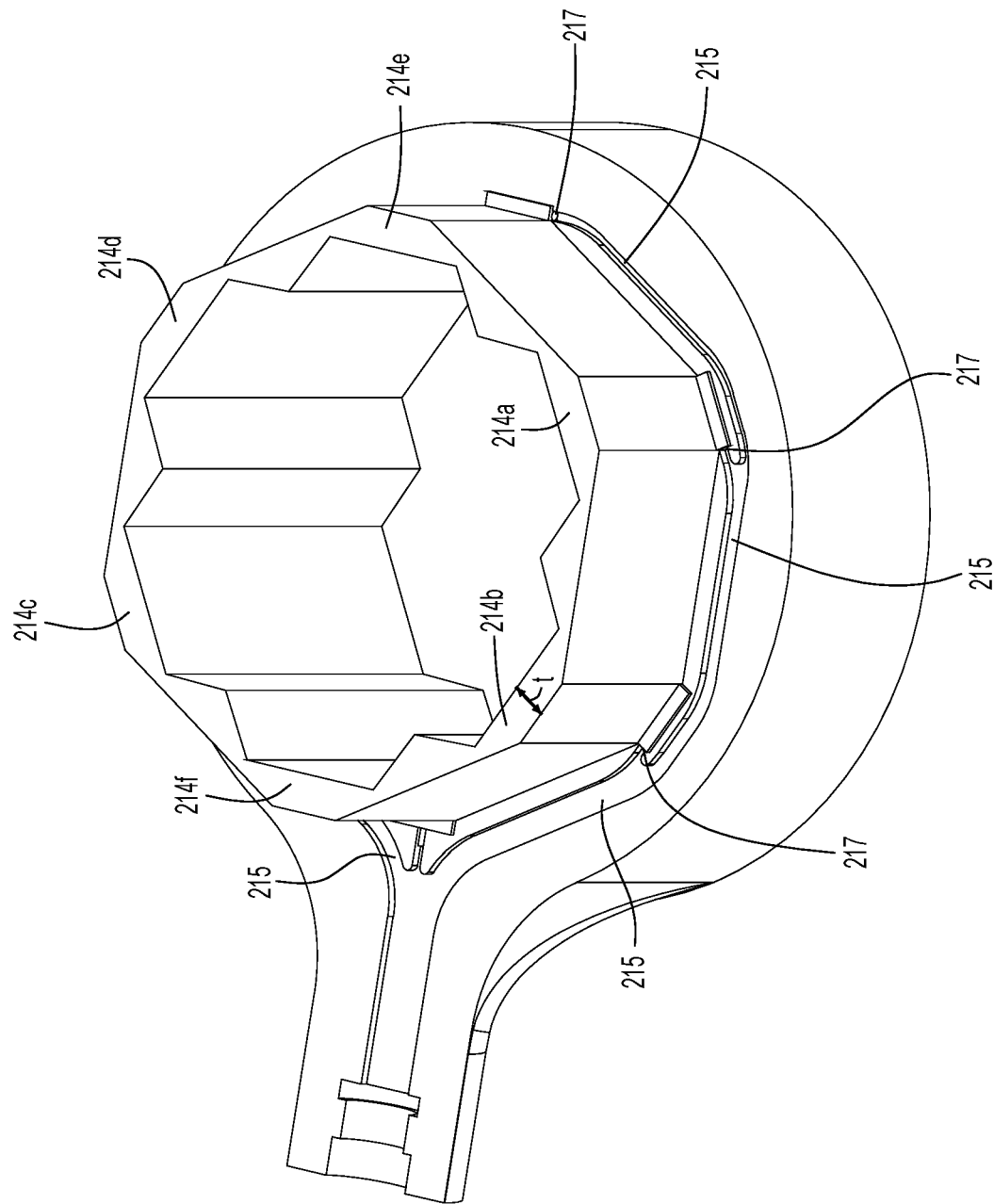

According to one implementation the first part 202 includes a base 210 from which extends a multi-face structure 211. The multi-face structure 211 includes six major internal faces 209a-f and respective external faces 213a-f. The internal faces 209a-f and the external faces 213a-f are separated by a respective wall 214a-f that is made of a material that is transparent to light at least in the visual spectrum. According to some implementations the thickness t of the walls 214a-f is between about 3 millimeters and about 6 millimeters According to one implementation the first part 202 is made of polycarbonate and formed via injection molding. Each of the side firing fibers 207a-e is respectively housed inside an air filled cavity 208a-e located adjacent external faces 213a-e. Trenches 215 located in the base 210 of the first part 202 facilitate a passage of the side firing optical fibers 207a-e about the perimeter of the multi-face structure 211 and lead to inlet openings 217 to the air filled cavities 208a-e as shown in FIG. 19C.

Figure 20B:
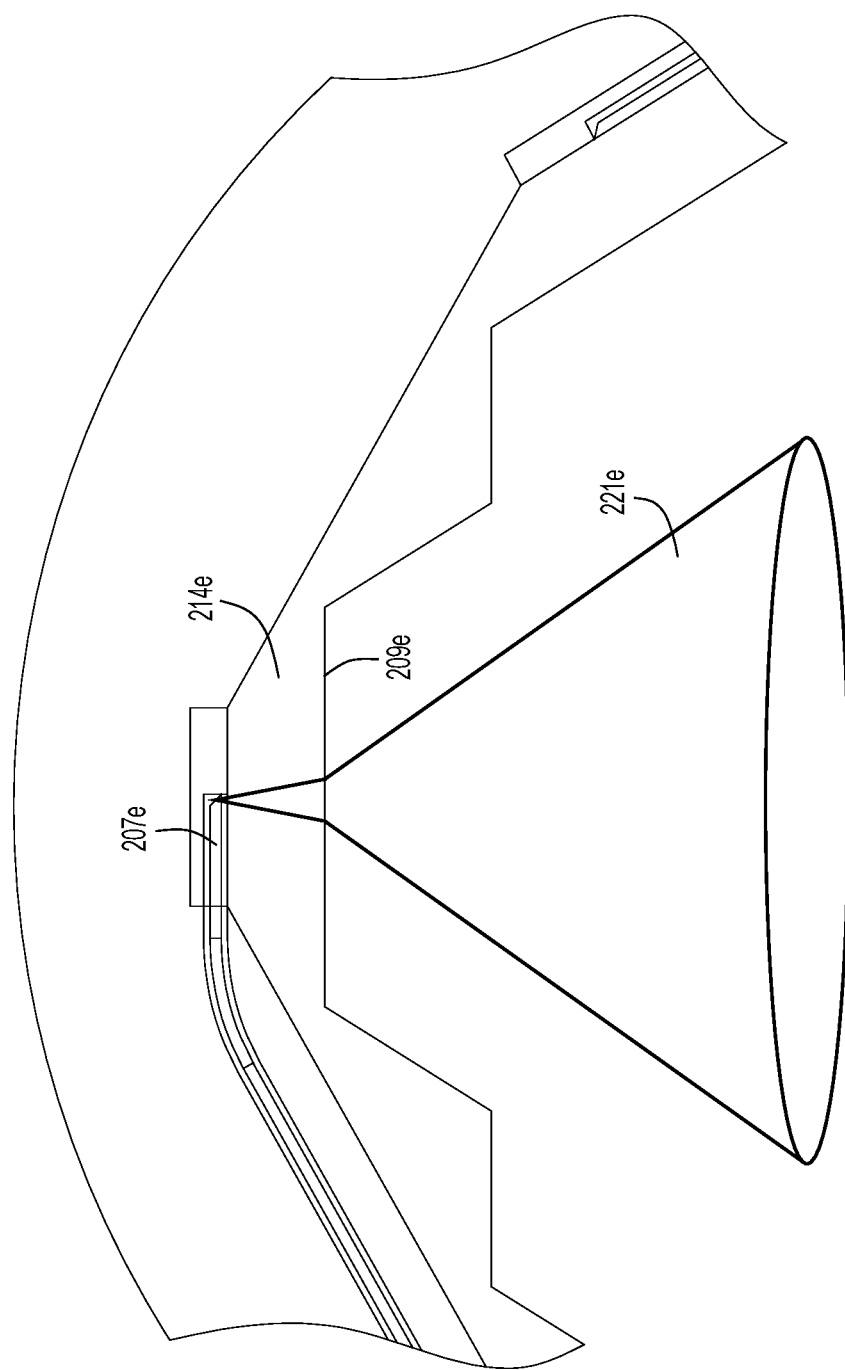
FIG. 20B shows the side firing fiber of FIG. 20A emitting a bacterial disinfecting light beam inward toward the through opening of the first part of the light disinfecting collar.

FIG. 20A shows an enlarged view of the side firing fiber 207e housed in the air filled cavity 208e. The side firing fiber 207e has an angled distal end 220e that is oriented to totally internally reflect a light beam passing through the fiber inward toward the central through opening 202a of the first part 202 as shown in FIG. 20B. The light beam 221e propagates through wall 214e and refracts at the internal face 209e due to the difference in the refractive indexes of the material that forms the wall 214e and of the air residing inside the through opening 202a. As noted above, according to some implementations the walls 214a-f are made of a plastic material such as polycarbonate.

Figure 21:
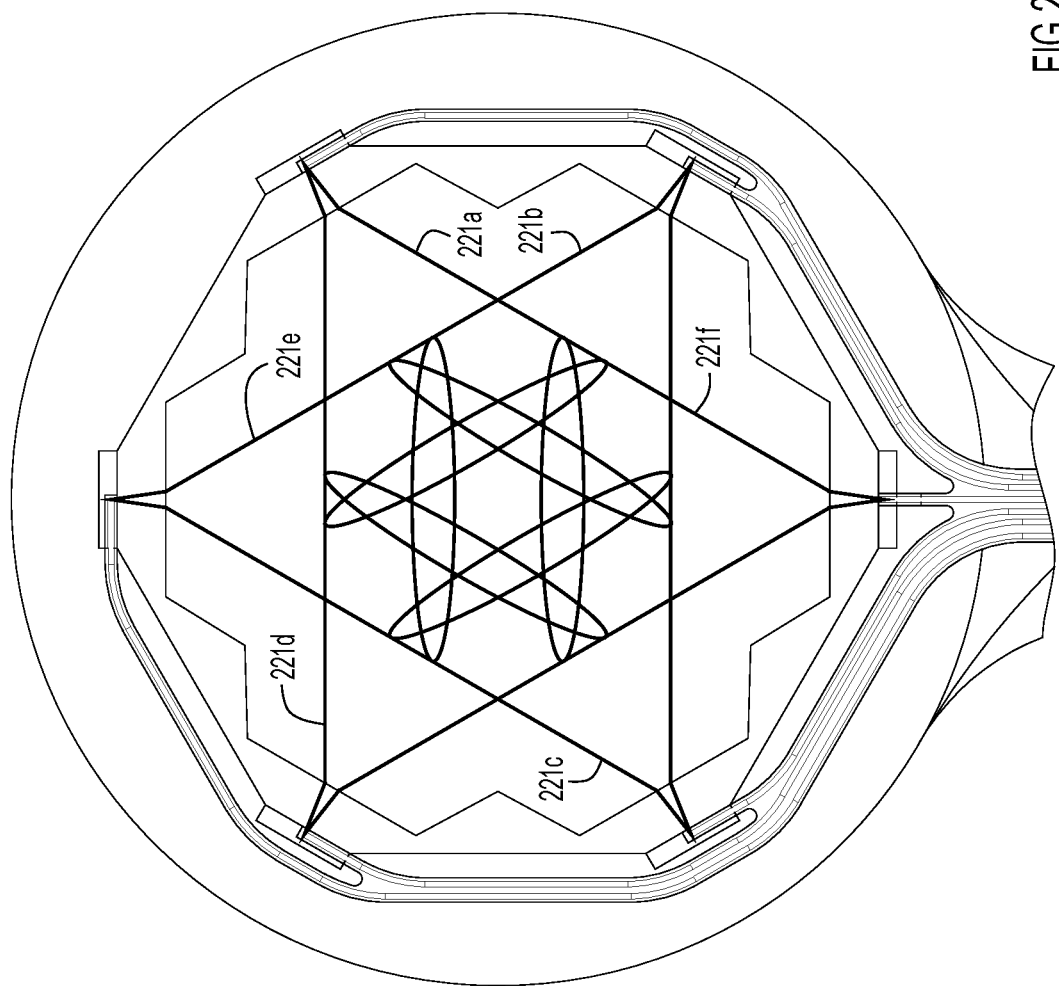
FIG. 21 is a cross-sectional top view of the first part shown in FIG. 19B with each of the optical fibers emitting a light beam inward toward the central through opening of the first part of the light disinfecting collar.

The end emitting fiber 206 is structured and oriented in a manner that results in the fiber core at the distal end of the fiber being butted against the external face 213f. According to one implementation the end of the fiber is attached to the external face 213f by use of an index matching adhesive that has a refractive index similar to that of the fiber core. According to such an implementation the distal end of the end emitting fiber may be spaced a short distance from the external face 213a with the gap separating the end of the fiber 206 and the external face being occupied by the index matching adhesive. As shown in FIG. 21, the light beam 221f emitted by the end emitting fiber 206 propagates through wall 214f and refracts at the internal face 209f due to the difference in the refractive indexes of the material that forms the wall 214f and of the air residing inside the through opening 202a. FIG. 21 also shows the light beams 221a-e respectively associated with side firing fibers 207a-e.

Figure 22:
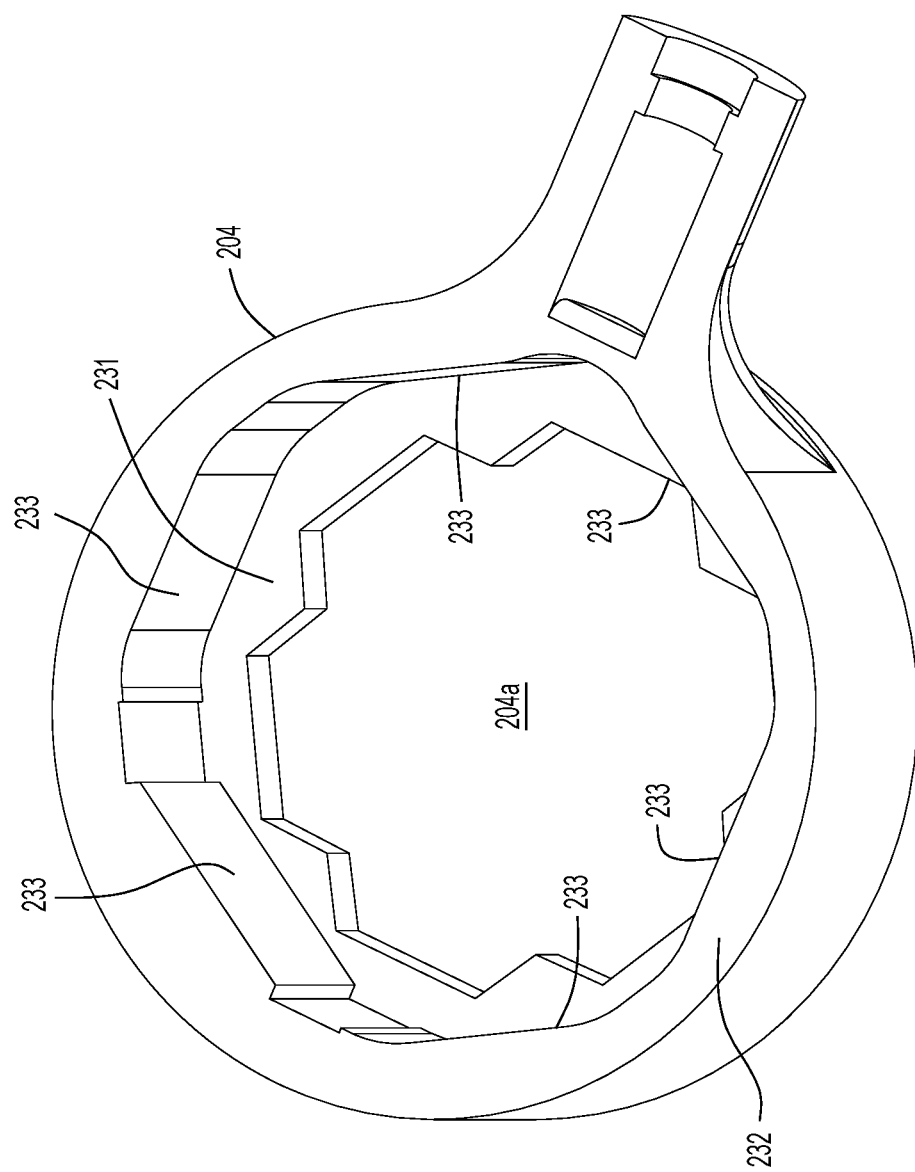
FIG. 22 shows the second part of the light disinfecting collar of FIG. 18B

FIGS. 18B and 22 illustrate a second part 204 of the collar 111 shown in FIG. 18A. The second part 204 has a though opening 204a that is concentric to the through opening 202a of the first part 202 when the first and second parts are assembled together. The second part 204 includes a cavity 231 defined by wall portions 233 that mimic the external shape of the multi-face structure 211 of the first part 202. According to one implementation the collar 111 is assembled by fitting the second part 204 over the first part 202 so that the multi-face structure 211 of the first part fits inside the cavity 231 of the second part. According to such an implementation, an inner face 232 of the second part rest on the base 210 of the first part 202 and resides over the trenches 215 through which the optical fibers 207a-e pass. According to some implementations the first and second parts are fitted with cooperating features that snap-fit the parts to one another in the assembled state. According to other implementations the second part is injection molded over the multi-face structure 211 of the first part 202.

According to yet other implementations the first and second parts 202 and 204 are attached together by use of an adhesive.

Figure 23:
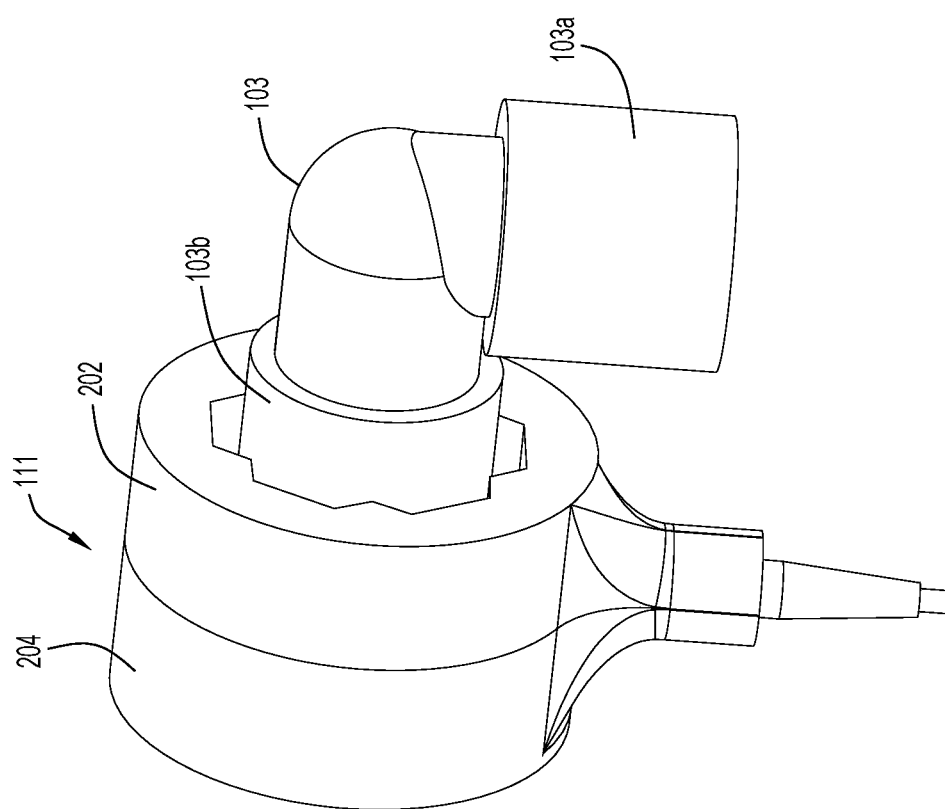
FIG. 23 shows a perspective view of the light disinfecting collar of FIG. 18A disposed about a portion of a connector that connects an end of the connector to the proximal end of an intubation tube.

FIG. 23 shows the collar 111 of FIG. 18A fitted over at least a portion of the connector 103 that couples the intubation tube 101 to the ventilator tube set 102.

Figure 24B:
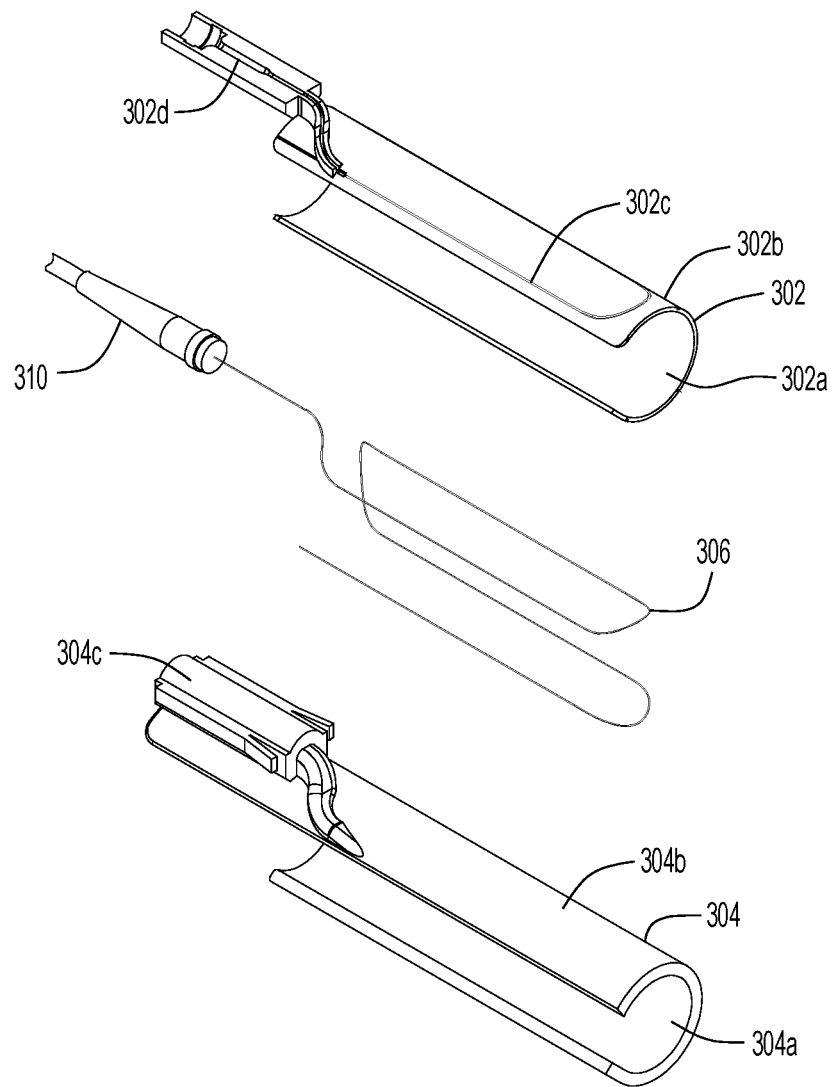
FIG. 24B is an exploded perspective view of a bite block according to one implementation.

FIG. 24A is a perspective view of a fully assembled self-disinfecting bite block 123 according to one implementation. FIG. 24A is an exploded perspective view of a first implementation of the bite block 123 of FIG. 24A. The bite block in this first implementation includes an inner member 302, an outer member 304 and a meandering radially emitting fiber 306. According to some implementations the inner and outer members 302 and 304 are C-shaped as shown in FIG. 24B. According to other implementations the inner and outer members 302 and 304 comprise a cylindrical shape. When assembled, the radially emitting fiber 306 is disposed between the inner surface of the 304a of the outer member 304 and the outer surface 304b of the inner member 302. According to some implementations the inner member 302 includes a recess 302c for housing at least a portion of the radially emitting fiber 306. The cross-sectional profile of the recess 302c may be similar in construction to any one of the recesses 128c shown in FIGS. 8A-C. In addition, the length of the radially emitting fiber 306 may be shorter than the length of the recess 302c to facilitate an axial movement of the fiber in the event the bite block is flexed or otherwise deformed during use by, for example, a biting down on the bite block 123 by the patient.

With continued reference to FIG. 24B, according to one implementation the bite block 123 is made by injection molding the inner member 302 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed, the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When the subassembly comprising the inner member 302 and radially emitting fiber 306 is complete, the outer member 304 is injection molded over the inner member 302 to cover at least the outer surface 302b of the inner member and the radially emitting fiber 306. According to some implementations the outer member 304 is injection molded over the subassembly to envelop the entirety of the inner member 302. According to such an implementation, the outer member 304 is produced to form a cap 304c that is formed over the projecting platform 302d of the inner member 302. In implementations where the outer member 304 covers the inner surface 302a of the inner member 302, the outer member is made of a material that is transparent to light at least in the visible spectrum. In such implementations, a light reflecting member, such as, for example, a light reflecting coating (e.g. light reflecting paint) or light reflecting film (e.g. a light reflecting metallic foil) may be disposed about the outer surface 304b of the outer member 304 to reflect light emitted by the radially emitting fiber in the direction of the outer surface 304b inward toward the axial through opening 312 of the bite block 123.

According to some implementations the outer member 304 is made of a light transparent material, at least in the visual spectrum, and no light reflective member is disposed about the outer surface 304b such that light emitted by the radially emitting fiber 306 is directed both inward toward the axial opening 312 of the bite block 123 and outward in a direction toward the mouth of the patient in which the bite block resides.

According to other implementations the light reflecting member is positioned within the bite block assembly to direct light outward in a direction toward the mouth of the patient in which the bite block resides.

Although not shown in the figures, the radially emitting fiber 306 to a bacterial disinfecting light source, such as a laser.

Figure 24C:
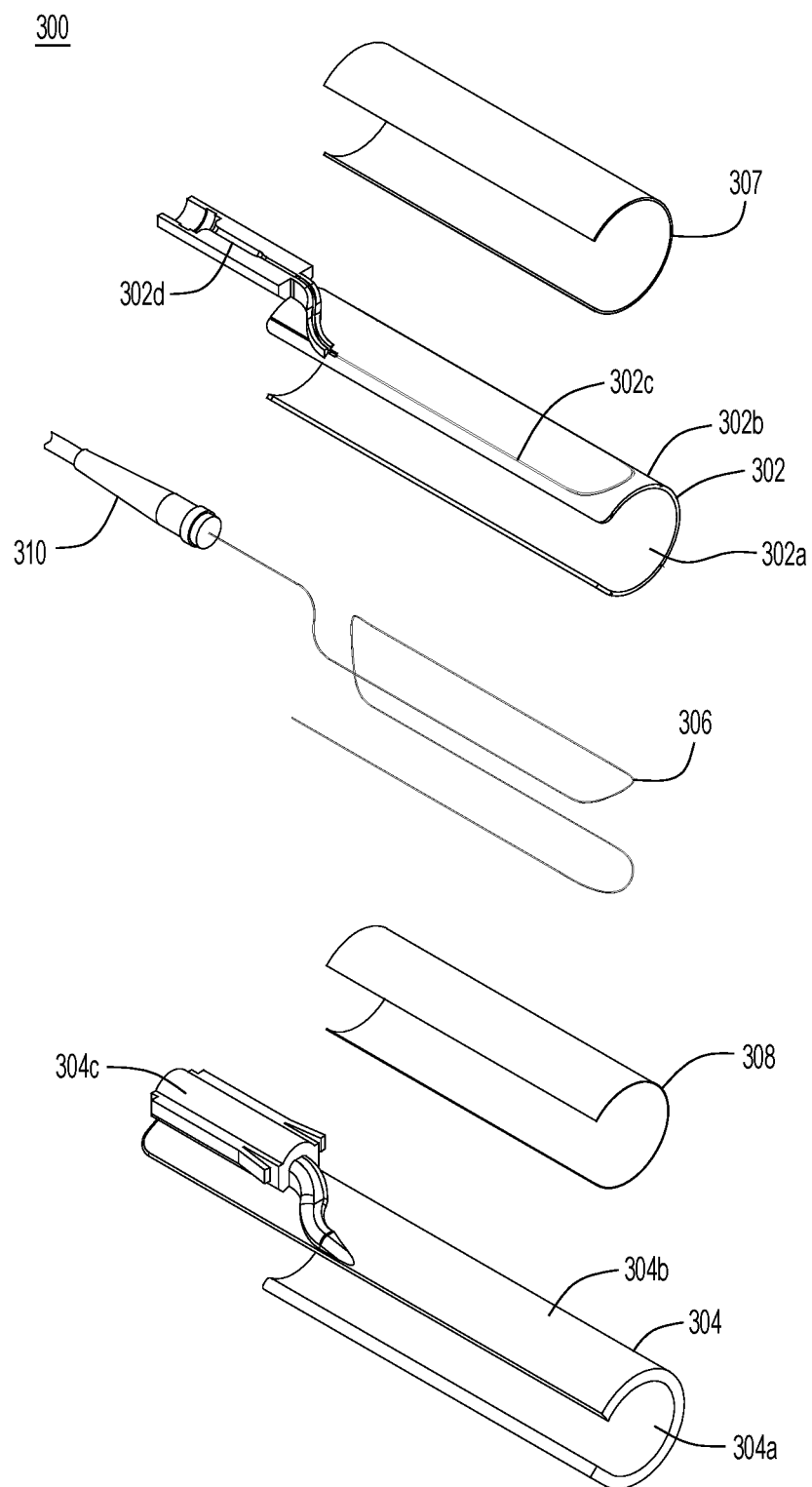
FIG. 24C is an exploded perspective view of a bite block according to another implementation.

FIG. 24C is an exploded view of a bite block 123 according to another implementation. The bite block is similar in construction to that of FIG. 24B and further includes a light reflecting member 307 interposed between the outer surface 302b of the inner member 302 and the inner surface 304a of the outer member 304. The bite block also includes an optical diffuser 308 that abuts the inner surface 302a of the inner member 302 and acts to more evenly distribute the light emitted by the radially emitting fiber into the axial through opening 312 of the bite block.

With continued reference to FIG. 24C, according to one implementation the bite block 123 is made by injection molding the inner member 302 over the optical diffuser 308 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed, the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When a first subassembly comprising the inner member 302, optical diffuser 308 and radially emitting fiber 306 is complete, the first subassembly is placed into a mold along with the light reflecting member 307, the light reflecting member 307 being disposed about the outer surface 302b of the inner member 302 to lie over the radially emitting fiber 306. The mold therefore holds therein a second subassembly that comprises the first subassembly and the light reflecting member 307. The outer member 304, which is made of a material transparent to light at least in the visual spectrum, is then injection molded to envelop portions of or the entirety of the second subassembly. According to some implementations, the outer member 304 is produced to form a cap 304c that is formed over the projecting platform 302d of the inner member 302.

Figure 25:
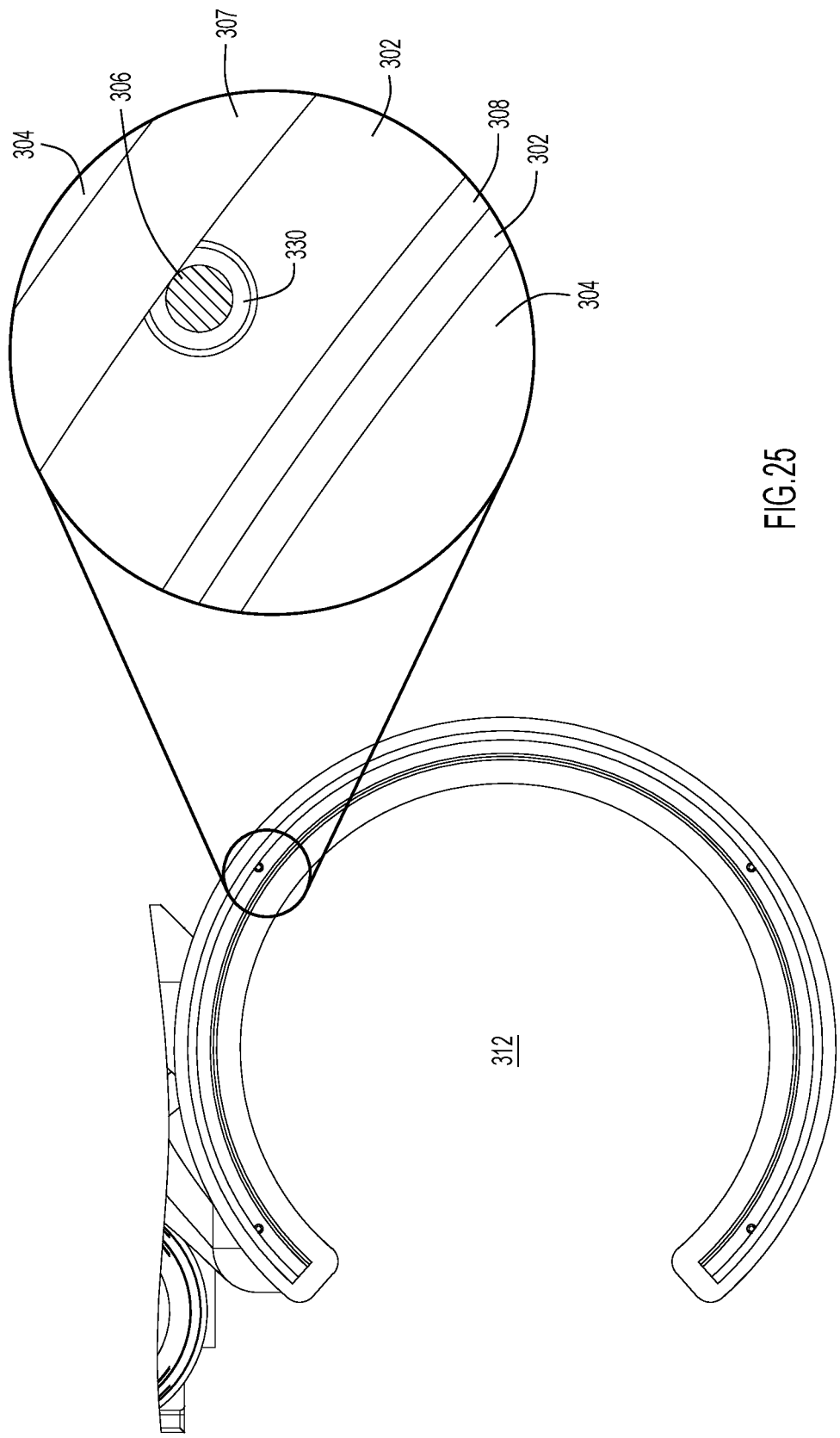
FIG. 25 shows a cross-sectional view of the assembled bite block of FIG. 24C.

According to some implementations the recess 302a has a construction similar to that of either FIG. 12A or 12B that results in the radially emitting fiber residing entirely inside the recess with a freedom of movement in both the radial direction and axial direction of the fiber. According to such an implementation, the light reflecting member 307 is sufficiently rigid to lie over the opening of the recess 302c (in a like manner to that of the optical diffuser 135 in FIGS. 12A and 12B) to prevent the material from which the outer member 304 is made from entering the recess during the injection molding of the outer member. As shown in FIG. 25, this construction results in an air gap 330 inside the recess 302c. According to some implementations the length of the radially emitting fiber 306 is also shorter than the length of the recess 302c to facilitate an axial movement of the fiber inside the recess when the bite block is flexed or otherwise deformed during use.

FIG. 25 illustrates a cross-sectional view of the bite block 123 of FIG. 24C in a fully assembled state.

Figure 24D:
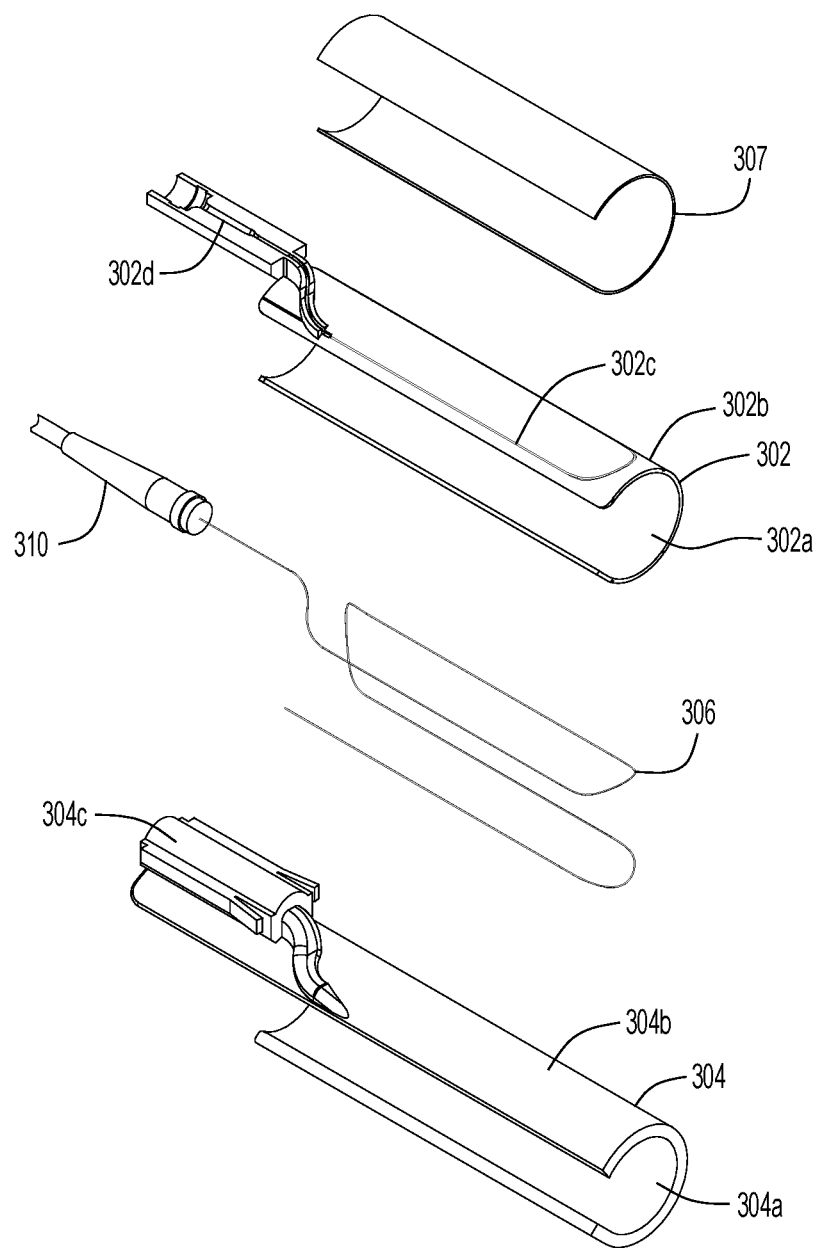
FIG. 24D is an exploded perspective view of a bite block according to another implementation.

FIG. 24D is an exploded perspective view of a bite block according to another implementation. The bite block is similar to the bite block of FIG. 24C absent the optical diffuser 308. According to one implementation the bite block 123 is made by injection molding the inner member 302 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed, the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When a first subassembly comprising the inner member 302 and radially emitting fiber 306 is complete, the first subassembly is placed into a mold along with the light reflecting member 307, the light reflecting member 307 being disposed about the outer surface 302b of the inner member 302 to lie over the radially emitting fiber 306. The mold therefore holds therein a second subassembly that comprises the first subassembly and the light reflecting member 307. The outer member 304, which is made of a material transparent to light at least in the visual spectrum, is then injection molded to envelop portions of or the entirety of the second subassembly. According to some implementations, the outer member 304 is produced to form a cap 304c that is formed over the projecting platform 302d of the inner member 302.

With continued reference to FIG. 24D, according to some implementations the recess 302a has a construction similar to that of either FIG. 12A or 12B that results in the radially emitting fiber residing entirely inside the recess with a freedom of movement in both the radial direction and axial direction of the fiber. According to such an implementation, the light reflecting member 307 is sufficiently rigid to lie over the opening of the recess 302c (in a like manner to that of the optical diffuser 135 in FIGS. 12A and 12B) to prevent the material from which the outer member 304 is made from entering the recess during the injection molding of the outer member. According to some implementations the length of the radially emitting fiber 306 is also shorter than the length of the recess 302c to facilitate an axial movement of the fiber inside the recess when the bite block is flexed or otherwise deformed during use.

Figure 24E:
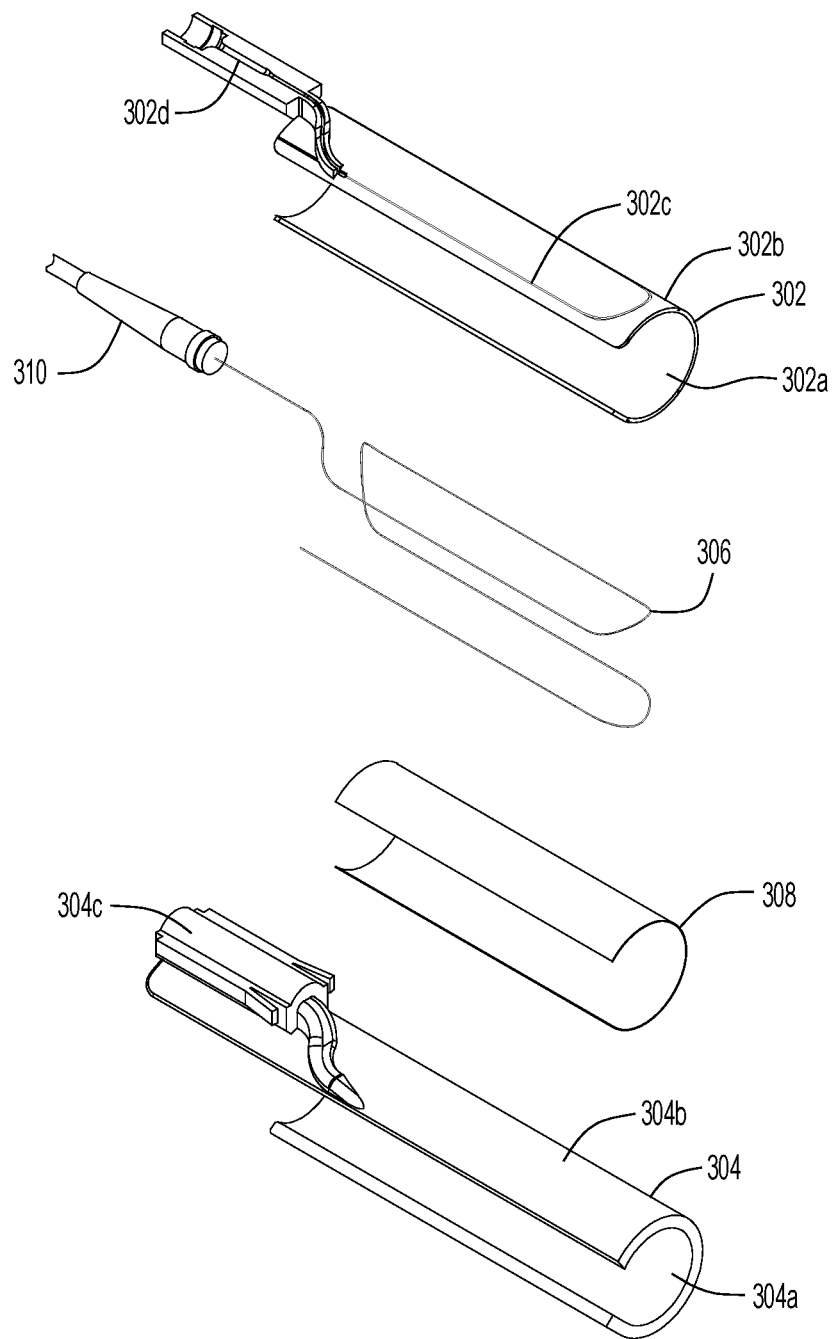
FIG. 24E is an exploded perspective view of a bite block according to another implementation.

FIG. 24E is an exploded perspective view of a bite block according to another implementation. The bite block is similar to the bite block of FIG. 24C absent the light reflecting member 307. According to one implementation the bite block 123 is made by injection molding the inner member 302 over the optical diffuser 308 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed, the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When a subassembly comprising the inner member 302, optical diffuser 308 and radially emitting fiber 306 is complete, the subassembly is placed into a mold and the outer member 304, which is made of a material transparent to light at least in the visual spectrum, is then injection molded to envelop portions of or the entirety of the subassembly. According to some implementations, the outer member 304 is produced to form a cap 304c that is formed over the projecting platform 302d of the inner member 302.

Figure 26A:
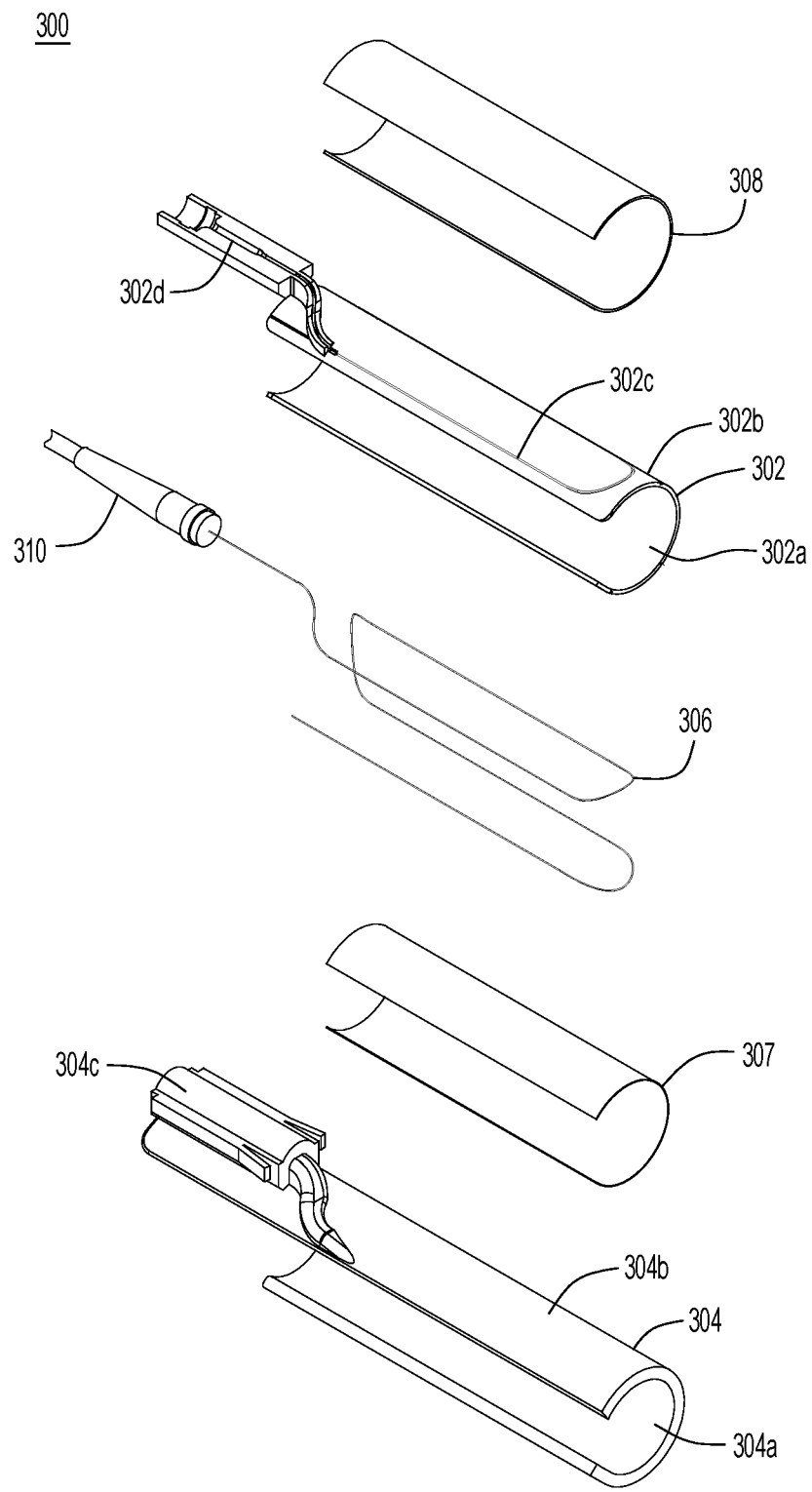
FIG. 26A is an exploded perspective view of a bite block according to another implementation.
Figure 27:
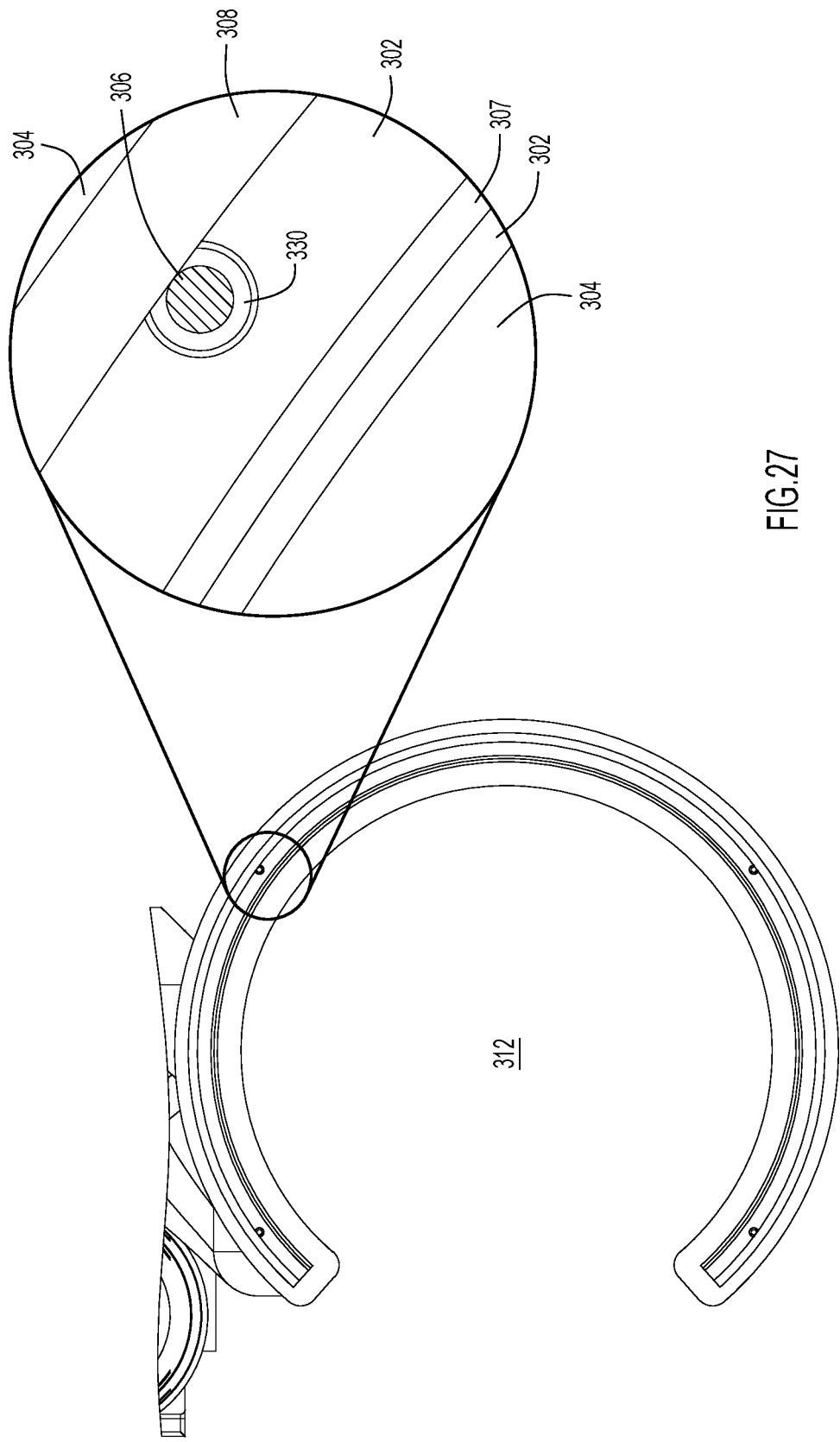
FIG. 27 shows a cross-sectional view of the assembled bite block of FIG. 26A.

FIG. 26A illustrates an exploded perspective view of a bite block according to another implementation. FIG. 27 shows a cross-sectional view of the parts of the bite block in an assembled state. According to one implementation the bite block 123 is made by injection molding the inner member 302 over the light reflecting member 307 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When a first subassembly comprising the inner member 302, light reflecting member 307 and radially emitting fiber 306 is complete, the first subassembly is placed into a mold along with the optical diffuser 307, the optical diffuser 308 being disposed about the outer surface 302b of the inner member 302 to lie over the radially emitting fiber 306. The mold therefore holds therein a second subassembly that comprises the first subassembly and the optical diffuser 308. The outer member 304, which is made of a material transparent to light at least in the visual spectrum, is then injection molded to envelop portions of or the entirety of the second subassembly. According to some implementations, the outer member 304 is produced to form a cap 304c that is formed over the projecting platform 302d of the inner member 302.

According to some implementations the recess 302a has a construction similar to that of either FIG. 12A or 12B that results in the radially emitting fiber residing entirely inside the recess with a freedom of movement in both the radial direction and axial direction of the fiber. According to such an implementation, the light reflecting member 307 is sufficiently rigid to lie over the opening of the recess 302c (in a like manner to that of the optical diffuser 135 in FIGS. 12A and 12B) to prevent the material from which the outer member 304 is made from entering the recess during the injection molding of the outer member. As shown in FIG. 25, this construction results in an air gap 330 inside the recess 302c. According to some implementations the length of the radially emitting fiber 306 is also shorter than the length of the recess 302c to facilitate an axial movement of the fiber inside the recess when the bite block is flexed or otherwise deformed during use.

FIG. 27 illustrates a cross-sectional view of the bite block 123 of FIG. 26A in a fully assembled state.

Figure 26B:
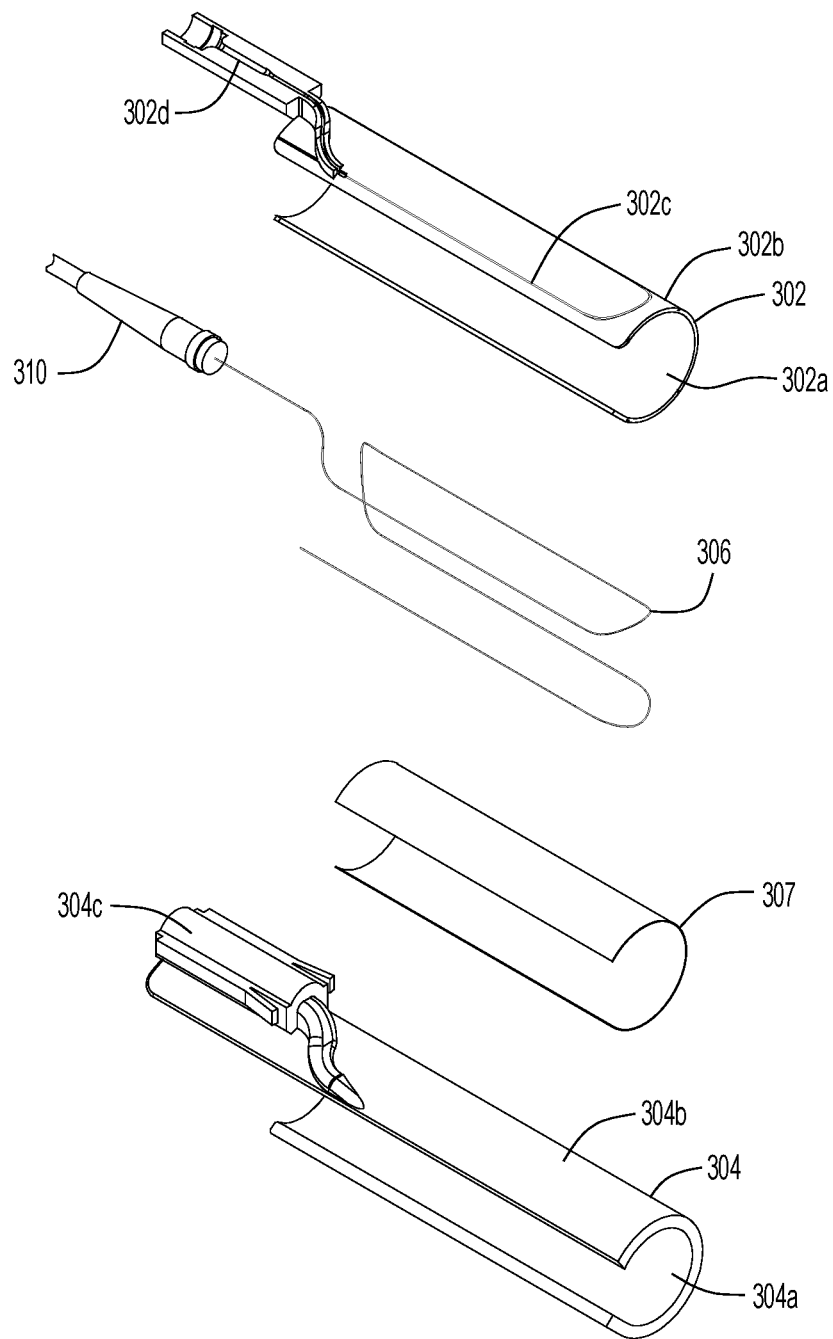
FIG. 26B is an exploded perspective view of a bite block according to another implementation.

FIG. 26B is an exploded perspective view of a bite block according to another implementation. The bite block is similar to the bite block of FIG. 26A absent the optical diffuser 308. According to one implementation the bite block 123 is made by injection molding the inner member 302 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed, the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When a first subassembly comprising the inner member 302 and radially emitting fiber 306 is complete, the first subassembly is placed into a mold along with the light reflecting member 7, the light reflecting member 307 being disposed about the inner surface 302a of the inner member 302. The mold therefore holds therein a second subassembly that comprises the first subassembly and the light reflecting member 307. The outer member 304, which is made of a material transparent to light at least in the visual spectrum, is then injection molded to envelop portions of or the entirety of the second subassembly. According to some implementations, the outer member 304 is produced to form a cap 304c that is formed over the projecting platform 302d of the inner member 302.

With continued reference to FIG. 26B according to some implementations the recess 302a has a construction similar to that of either FIG. 12A or 12B that results in the radially emitting fiber residing entirely inside the recess with a freedom of movement in both the radial direction and axial direction of the fiber. According to such an implementation, the light reflecting member 307 is sufficiently rigid to lie over the opening of the recess 302c (in a like manner to that of the optical diffuser 135 in FIGS. 12A and 12B) to prevent the material from which the outer member 304 is made from entering the recess during the injection molding of the outer member. According to some implementations the length of the radially emitting fiber 306 is also shorter than the length of the recess 302c to facilitate an axial movement of the fiber inside the recess when the bite block is flexed or otherwise deformed during use.

Figure 26C:
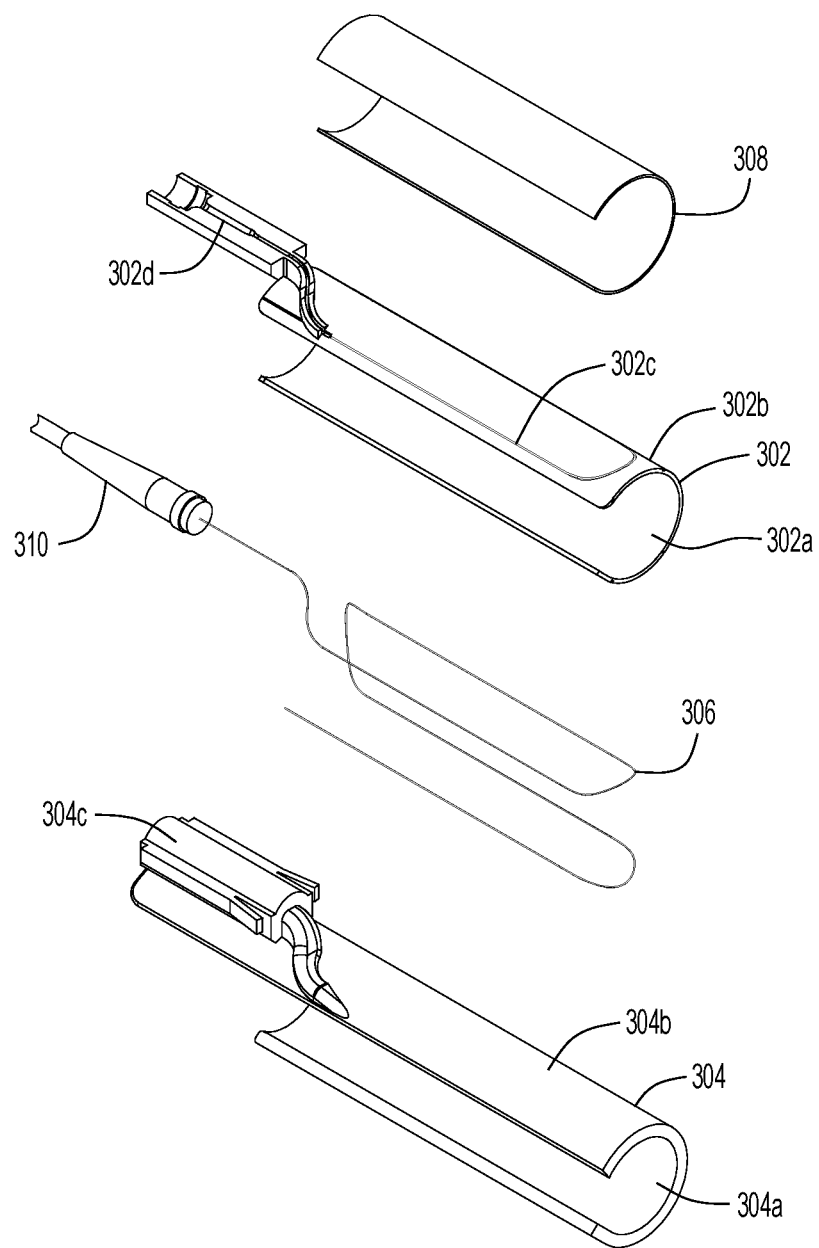
FIG. 26C is an exploded perspective view of a bite block according to another implementation.

FIG. 26C is an exploded perspective view of a bite block according to another implementation. The bite block is similar to the bite block of FIG. 24C absent the light reflecting member 307. According to one implementation the bite block 123 is made by injection molding the inner member 302 from a material that is transparent to light at least in the visual spectrum. In the injection molding process the recess 302c is formed along with a projecting platform 302d. The projecting platform 302d comprises features for receiving a distal end portion of a strain relief member 310 from which the proximal end of the radially emitting fiber 306 projects. Upon the inner member 302 being formed, the radially emitting fiber 306 is fitted into the recess 302c and may be held therein by the structure of the recess itself (as described above in conjunction with FIGS. 8B and 8C) or by use of an adhesive that is transparent to light at least in the visual spectrum. When a subassembly comprising the inner member 302 and radially emitting fiber 306 is complete, the subassembly is placed into a mold with an optical diffuser 308 lying over the radially emitting fiber 306. The outer member 304, which is made of a material transparent to light at least in the visual spectrum, is then injection molded to envelop portions of or the entirety of the subassembly. According to some implementations, the outer member 304 is produced to form a cap 304c that is formed over the projecting platform 302d of the inner member 302.

While specific implementations and applications have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

For example, the disclosure describes in detail various implementations of light disinfecting systems and of their individual components. It is appreciated, however, that the disclosed features are applicable to a host of other types of devices inside and outside the medical field. As mentioned above, the apparatus and methods disclosed herein can also be applied to equipment or components of water processing plants, food processing plants, dairies, livestock habitation facilities, etc. For example, the lip guard 128 disclosed herein may comprise a stand-alone device that may be applied over a wound or puncture site of a patient, or over any other surface or component in need of bacterial disinfection. Likewise, the collar 111 and bite block 123 configurations disclosed herein can each be stand-alone devices that may be fitted around an extremity of a patient, a fluid pipe in a food processing plant, etc.

The following clauses disclose in an unlimited way additional implementations, with each clause representing an implementation. Additional implementations are represented by one or more of the implementations of one group or groups of clauses with one or more implementations of another group or groups of clauses. Group A through J clauses are provided.

Group A Clauses:

Clause 1. An apparatus for bacterially disinfecting a planar surface and a non-planar surface, the apparatus comprising:
  a flexible body capable of assuming a planar state and a non-planar state, the flexible body being made of a material that is transparent to light and having formed therein a channel;
  a radially emitting fiber having a length and being disposed in the channel, the radially emitting fiber having a longitudinal axis and configured to radially emit bacterial disinfecting light, at least a portion of the radially emitting fiber having an axial and/or radial freedom of movement inside the channel when the flexible body transitions between the planar and non-planar states, the axial and/or radial freedom of movement reducing the amount of tensile stress applied along the length of the radially emitting fiber when the flexible body transitions between the planar and non-planar states as compared to an amount of tensile stress that would otherwise be applied to the radially emitting fiber in an absence of the axial and/or radial freedom of movement of the radially emitting fiber inside the channel.

Clause 2. The apparatus according to clause 1, wherein the radially emitting fiber has a proximal end and a distal end and the channel has an end wall, the distal end of the radially emitting fiber being spaced a distance from the end wall of the channel.

Clause 3. The apparatus according to clause 2, wherein the proximal end of the radially emitting fiber is fixed relative to the flexible body and the distal end of the radially emitting fiber is not fixed to the flexible body.

Clause 4. The apparatus according to clause 2, wherein the distance between the distal end of the radially emitting fiber and the end wall of the channel changes when the flexible body transitions between the planar and non-planar states.

Clause 5. The apparatus according to anyone of clauses 1 to 4, wherein the radially emitting fiber has an outer diameter and a corresponding cross-sectional area and the channel has a cross-sectional area, the cross-sectional area of the radially emitting fiber being less that the cross-sectional area of the channel.

Clause 6. The apparatus according to anyone of clauses 1 to 4, wherein the channel includes one or more straight sections and one or more curved sections, the one or more straight sections having a first cross-sectional area and the one or more curved sections having a second cross-sectional area that is greater than the first cross-sectional area.

Clause 7. The apparatus according to anyone of clauses 1 to 4, wherein the channel includes at least one straight section and at least one curved section, the curved section being defined by one or more walls, at least a portion of the radially emitting fiber residing in the curved section being spaced apart from the one or more walls.

Clause 8. The apparatus according to anyone of clauses 1 to 7, wherein the channel is located internal to the flexible body.

Clause 9. The apparatus according to anyone of clauses 1 to 8, wherein the radially emitting fiber has a minimum bending radius, the flexible body being sufficiently rigid to prevent a bending of the radially emitting fiber beyond the minimum bending radius.

Clause 10. The apparatus according to any one of clauses 1 to 9, wherein the flexible body has a front face and a back face, the channel being formed in the front face, the back face of the flexible body comprising a light reflecting coating that is configured to reflect the bacterial disinfecting light emitted from a backside of the radially emitting fiber in a direction toward the front face of the flexible body.

Clause 11. The apparatus according to anyone of clauses 1 to 9, wherein the flexible body has a front face and a back face, the channel being formed in the front face, the apparatus further comprising a light reflecting element disposed over the back face of the flexible body, the light reflecting element having a front face that faces the back face of the flexible body and a back face opposite the front face, the front face of the light reflecting element being configured to reflect the bacterial disinfecting light emitted from a backside of the radially emitting fiber in a direction toward the front face of the flexible body.

Clause 12. The apparatus according to clause 11, wherein the light reflecting element is a metallic foil.

Clause 13. The apparatus according to clause 11, wherein the light reflecting element is a metal sheet.

Clause 14. The apparatus according to anyone of clauses 1 to 13, further comprising a flexible liner that is transparent to light, the flexible liner enveloping the flexible body.

Clause 15. The apparatus according to anyone of clauses 1 to 13, further comprising a flexible liner that lies over the front face of the flexible body and the back face of the light reflecting element, the flexible liner being transparent to light.

Clause 16. The apparatus according to clause 14, further comprising an optical diffuser disposed between the front face of the flexible body and the flexible liner.

Clause 17. The apparatus according to clause 15, further comprising an optical diffuser disposed between the front face of the flexible body and the flexible liner.

Clause 18. The apparatus according to clause 1, further comprising an optical diffuser having a front face and a back face, the back face of the optical diffuser being disposed over the front face of the flexible body.

Clause 19. The apparatus according to clause 18, further comprising a flexible liner transparent to light that lies over the front face of the optical diffuser and the back face of the flexible body.

Clause 20. The apparatus according to clause 19, wherein a light reflecting coating or element is disposed between the back face of the flexible body and the flexible liner.

Clause 21. The apparatus according to clause 10, wherein the radially emitting fiber has a diameter dimension, the channel has a bottom surface, the bottom surface of the channel and the back face of the flexible body being separated by a wall having a thickness dimension that is greater than the diameter dimension of the radially emitting fiber.

Clause 22. The apparatus according to clause 11, wherein the radially emitting fiber has a diameter dimension, the channel has a bottom surface, the bottom surface of the channel and the front face of the light reflecting element being separated by a distance that is greater than or equal to the diameter dimension of the radially emitting fiber.

Clause 23. The apparatus according to clause 10, wherein the radially emitting fiber has a diameter dimension, the channel has a bottom surface, the bottom surface of the channel and the back face of the flexible body being separated by a wall having a thickness dimension that is greater than 2 to 5 times the diameter dimension of the radially emitting fiber.

Clause 24. The apparatus according to clause 11, wherein the radially emitting fiber has a diameter dimension, the channel has a bottom surface, the bottom surface of the channel and the front face of the light reflecting element being separated by a distance that is greater than 2 to 5 times the diameter dimension of the radially emitting fiber.

Clause 25. The apparatus according to clause 1, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 26. The apparatus according to clause 25, wherein the elongate tubular member is fixed inside the channel.

Clause 27. The apparatus according to clause 26, wherein the elongate tubular member is fixed inside the channel by use of a light transparent adhesive.

Clause 28. The apparatus according to clause 25, wherein the elongate tubular member is flexible.

Clause 29. The apparatus according to clause 25, wherein the elongate tubular member has a length that is greater than the length of the radially emitting fiber.

Clause 30. The apparatus according to clause 1, wherein a gap exists between an outer surface of the radially emitting fiber and an inner wall of the channel, the gap being occupied by an index matching gel that facilitates a coupling of light between the outer surface of the radially emitting fiber and the inner wall of the channel.

Clause 31. The apparatus according to clause 30, wherein the index matching gel allows the radially emitting fiber to more easily slide within the channel in comparison to the fiber's ability to slide in the channel absent the index matching gel.

Clause 32. The apparatus according to clause 30, wherein the radially emitting fiber comprises a core that is surrounded by a cladding, the cladding having a first refractive index, the inner wall of the channel comprising a material having a second refractive index, the index matching gel having a third refractive index that is between the first refractive index and the second refractive index.

Group B Clauses:

Clause 1. A lip guard for an endotracheal tube support assembly that comprises a bite block, the lip guard comprising:
- a flexible body made of a material that is transparent to light and having formed therein a channel, the flexible body having an as-manufactured state and a flexed state that occurs when the flexible body is bent away from its as-manufactured state;
- a radially emitting fiber having a length and configured to radially emit bacterial disinfecting light, the radially emitting fiber having a longitudinal axis that is disposed in the channel, at least a portion of the radially emitting fiber having an axial and/or radial freedom of movement inside the channel when the flexible body transitions between the as-manufactured state and the flexed state, the axial and or radial freedom of movement reducing the amount of tensile stress applied along the length of the radially emitting fiber when the flexible body is bent as compared to an amount of tensile stress that would otherwise be applied to the radially emitting fiber in an absence of the axial and/or radial freedom of movement of the radially emitting fiber inside the channel.

Clause 2. The lip guard according to clause 1, wherein the radially emitting fiber has a proximal end and a distal end and the channel has an end wall, the distal end of the radially emitting fiber being spaced a distance from the end wall of the channel.

Clause 3. The lip guard according to anyone of clauses 1 to 2, wherein the proximal end of the radially emitting fiber is fixed relative to the flexible body and the distal end of the radially emitting fiber is not fixed to the flexible body.

Clause 4. The lip guard according to clause 2, wherein the distance between the distal end of the radially emitting fiber and the end wall of the channel changes when the flexible body transitions between the as-manufactured and flexed states.

Clause 5. The lip guard according to anyone of clauses 1 to 4, wherein the radially emitting fiber has an outer diameter and a corresponding cross-sectional area and the channel has a cross-sectional area, the cross-sectional area of the radially emitting fiber being less that the cross-sectional area of the channel.

Clause 6. The lip guard according to anyone of clauses 1 to 5, wherein the channel includes one or more straight sections and one or more curved sections, the one or more straight sections having a first cross-sectional area and the one or more curved sections having a second cross-sectional area that is greater than the first cross-sectional area.

Clause 7. The lip guard according to clause 1, wherein the channel includes at least one straight section and at least one curved section, the curved section being defined by one or more walls, at least a portion of the radially emitting fiber residing in the curved section being spaced apart from the one or more walls.

Clause 8. The lip guard according to anyone of clauses 1 to 7, wherein the channel is located internal to the flexible body.

Clause 9. The lip guard according to anyone of clauses 1 to 8, wherein the radially emitting fiber has a minimum bending radius, the flexible body being sufficiently rigid to prevent a flexing of the flexible body inside the channel that would result in a bending of the radially emitting fiber beyond the minimum bending radius.

Clause 10. The lip guard according to clause 1, wherein the radially emitting fiber has a minimum bending radius, the lip guard being sufficiently rigid to prevent a bending of the radially emitting fiber beyond the minimum bending radius.

Clause 11. The lip guard according to any of clauses 1-10, wherein the flexible body has a front face and a back face, the channel being formed in the front face, the back face of the flexible body comprising a light reflecting coating that is configured to reflect a bacterial disinfecting light emitted from a backside of the radially emitting fiber in a direction toward the front face of the flexible body.

Clause 12. The lip guard according to anyone of clauses 1 to 10, wherein the flexible body has a front face and a back face, the channel being formed in the front face, the lip guard further comprising a light reflecting element disposed over the back face of the flexible body, the light reflecting element having a front face that faces the back face of the flexible body and a back face opposite the front face, the front face of the light reflecting element being configured to reflect a bacterial disinfecting light emitted from a backside of the radially emitting fiber in a direction toward the front face of the flexible body.

Clause 13. The lip guard according to clause 12, wherein the light reflecting element is a metallic foil.

Clause 14. The lip guard according to clause 12, wherein the light reflecting element is a metal sheet.

Clause 15. The lip guard according to clause 11, further comprising a flexible liner that is transparent to light, the flexible liner enveloping the flexible body.

Clause 16. The lip guard according to clause 12, further comprising a flexible liner that lies over the front face of the flexible body and the back face of the light reflecting element, the flexible liner being transparent to light.

Clause 17. The lip guard according to clause 15, further comprising an optical diffuser disposed between the front face of the flexible body and the flexible liner.

Clause 18. The lip guard according to clause 16, further comprising an optical diffuser disposed between the front face of the flexible body and the flexible liner.

Clause 19. The lip guard according to clause 1, further comprising an optical diffuser having a front face and a back face, the back face of the optical diffuser being disposed over the front face of the flexible body.

Clause 20. The lip guard according to clause 19, further comprising a liner that lies over the front face of the optical diffuser and the back face of the flexible body.

Clause 21. The lip guard according to clause 20, further comprising a light reflecting coating or light reflecting element that is disposed between the back face of the flexible body and the liner.

Clause 22. The lip guard according to clause 11, wherein the radially emitting fiber has a diameter dimension, the channel has a bottom surface, the bottom surface of the channel and the back face of the flexible body being separated by a wall having a thickness dimension that is greater than the diameter dimension of the radially emitting fiber.

Clause 23. The lip guard according to clause 12, wherein the radially emitting fiber has a diameter dimension, the channel has a bottom surface, the bottom surface of the channel and the front face of the light reflecting element being separated by a distance that is greater than or equal to the diameter dimension of the radially emitting fiber.

Clause 24. The lip guard according to clause 11, wherein the radially emitting fiber has a diameter dimension, the channel has a bottom surface, the bottom surface of the channel and the back face of the flexible body being separated by a wall having a thickness dimension that is greater than 2 to 5 times the diameter dimension of the radially emitting fiber.

Clause 25. The lip guard according to clause 12, wherein the radially emitting fiber has a diameter dimension, the channel has a bottom surface, the bottom surface of the channel and the front face of the light reflecting element being separated by a distance that is greater than 2 to 5 times the diameter dimension of the radially emitting fiber.

Clause 26. The lip guard according to clause 1, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 27. The lip guard according to clause 26, wherein the elongate tubular member is fixed inside the channel.

Clause 28. The lip guard according to clause 27, wherein the elongate tubular member is fixed inside the channel by use of a light transparent adhesive.

Clause 29. The lip guard according to clause 25, wherein the elongate tubular member is flexible.

Clause 30. The lip guard according to clause 25, wherein the elongate tubular member has a length that is greater than the length of the radially emitting fiber.

Clause 31. The lip guard according to clause 1, wherein the flexible body comprises a through opening configured to receive therein the bite block.

Group C Clauses:

Clause 1. A method for making an apparatus for bacterially disinfecting a surface, the method comprising:
  obtaining a light transparent body that has a front face and a back face with there being a channel formed in the front face;
  applying to the back face of the body a light reflecting element that is configured to reflect light in a direction toward the front face of the body;
  inserting a radially emitting fiber into the channel to form a subassembly that includes the light transparent body, the light reflecting element and the radially emitting fiber, the radially emitting fiber being configured to radially emit bacterial disinfecting light; and
  injection molding a light transparent liner over at least the front face of the light transparent body.

Clause 2. The method according to clause 1, wherein the liner is injection molded to envelop the subassembly.

Clause 3. The method according to clause 1, wherein each of the light transparent body and light transparent liner is flexible that results in the apparatus being flexible when the apparatus is fully assembled.

Clause 4. The method according to anyone of clauses 1 to 3, wherein the light transparent body and the light transparent liner are made of a same material.

Clause 5. The method according to anyone of clauses 1 to 3, wherein the light transparent body is made of a first material and the light transparent liner is made of a second material different than the first material.

Clause 6. The method according to anyone of clauses 1 to 5, wherein the process of applying to the back face of the light transparent body a light reflecting element comprises coating the back face with a light reflecting paint.

Clause 7. The method according to anyone of clauses 1 to 5, wherein the process of applying to the back face of the light transparent body a light reflecting element comprises applying a foil to the back face of the light transparent body, the foil having a light reflecting front face and a back face, the front face of the foil lying over the back face of the light transparent body.

Clause 8. The method according to clause 7, further comprising injection molding the light transparent liner over the back face of the foil.

Clause 9. The method according to anyone of clauses 1 to 5, wherein the process of applying to the back face of the light transparent body a light reflecting element comprises applying a metal sheet to the back face of the light transparent body, the metal sheet having a light reflecting front face and a back face, the front face of the metal sheet lying over the back face of the light transparent body.

Clause 10. The method according to clause 9, further comprising injection molding the light transparent liner over the back face of the metal sheet.

Clause 11. The method according to anyone of clauses 1 to 10, wherein obtaining a light transparent body that has a front face and a back face with there being a channel formed in the front face includes injection molding a polymeric material to form the light transparent body, the channel being formed in front face of the light transparent body during the injection molding.

Clause 12. The method according to anyone of clauses 1 to 11, wherein each of the light transparent body, light reflecting element and light transparent liner is made of a flexible material that results in the apparatus being flexible with an ability to transition between flat and curved configurations to respectively bacterially disinfect a flat surface and a curved surface.

Group D Clauses:

Clause 1. A method for making an apparatus for bacterially disinfecting a surface, the method comprising:
  obtaining a light transparent body that has a front face and a back face with there being a channel formed in the front face;
  applying to the back face of the body a light reflecting element that is configured to reflect light in a direction toward the front face of the body, the light reflecting element having a back face and a front face that faces the back face of the body;
  inserting a radially emitting fiber that is configured to radially emit bacterial disinfecting light into the channel;
  applying an optical diffuser element over the front face of the body and the radially emitting fiber to form a subassembly that includes the light transparent body, the light reflecting element, the radially emitting fiber and the optical diffuser element.
  injection molding a light transparent liner over at least the front face of the optical diffuser.

Clause 2. The method according to clause 1, wherein the light transparent liner is injection molded to envelop the subassembly.

Clause 3. The method according to anyone of clauses 1 to 2, wherein the light transparent body, optical diffuser and light transparent liner are made of flexible materials that results in the apparatus being flexible when fully assembled.

Clause 4. The method according to clause 3, wherein the light transparent body and light transparent liner are made of the same flexible material.

Clause 5. The method according to clause 3, wherein the light transparent body is made of a first flexible material and the light transparent liner is made of a second material different than the first flexible material.

Clause 6. The method according to anyone of clauses 1 to 5, wherein the process of applying to the back face of the light transparent body a light reflecting element comprises coating the back face with a light reflecting paint.

Clause 7. The method according to anyone of clauses 1 to 5, wherein the process of applying to the back face of the light transparent body a light reflecting element comprises applying a foil to the back face of the light transparent body, the foil having a light reflecting front face and a back face, the front face of the foil lying over the back face of the light transparent body.

Clause 8. The method according to clause 7, further comprising injection molding the light transparent liner over the back face of the foil.

Clause 9. The method according to anyone of clauses 1 to 5, wherein the process of applying to the back face of the light transparent body a light reflecting element comprises applying a metal sheet to the back face of the light transparent body, the metal sheet having a light reflecting front face and a back face, the front face of the metal sheet lying over the back face of the light transparent body.

Clause 10. The method according to clause 9, further comprising injection molding the light transparent liner over the back face of the metal sheet.

Clause 11. The method according to anyone of clauses 1 to 10, wherein obtaining the light transparent body that has a front face and a back face with there being a channel formed in the front face includes injection molding a polymeric material to form the light transparent body, the channel being formed in front face of the light transparent body during the injection molding.

Clause 12. The method according to anyone of clauses 1 to 11, wherein the light transparent body, light reflecting element, optical diffuser and light transparent liner are made of flexible materials that results in the apparatus being flexible with an ability to transition between flat and curved configurations to respectively bacterially disinfect a flat surface and a curved surface.

Group E Clauses:

Clause 1. A method for making an apparatus for bacterially disinfecting a surface, the method comprising:
  obtaining a light transparent body that has a front face and a back face with there being a channel formed in the front face;
  applying to the back face of the light transparent body a light reflecting element that is configured to reflect light in a direction toward the front face of the light transparent body, the light reflecting element having a back face and a front face that faces the back face of the light transparent body;
  inserting a radially emitting fiber into the channel to form a first subassembly that includes the light transparent body, the light reflecting element and the radially emitting fiber, the radially emitting fiber being configured to radially emit bacterial disinfecting light;
  injection molding a light transparent first liner over the first subassembly, the first liner including a first portion that lies over the front face of the light transparent body and a second portion that lies over the back face of the light reflecting element,
  applying an optical diffuser element over the first portion of the first liner to form a second subassembly that includes the light transparent body, the light reflecting element, the radially emitting fiber, the first liner and the optical diffuser; and
  injection molding a light transparent second liner over the second subassembly.

Clause 2. The method according to clause 1, wherein the first liner is injection molded to envelop the first subassembly.

Clause 3. The method according to clause 1, wherein the second liner is injection molded to envelop the second subassembly.

Clause 4. The method according to clause 2, wherein the second liner is injection molded to envelop the second subassembly.

Clause 5. The method according to anyone of clauses 1 to 4, wherein the light transparent body, light reflecting element, first liner, second liner and optical diffuser are made of a flexible material that results in the apparatus being flexible when fully assembled.

Clause 6. The method according to clause 5, wherein the light transparent body, first liner and second liner are made of the same flexible material.

Clause 7. The method according to clause 5, wherein the light transparent body is made of a first flexible material and the first and second liners are made of a second material different than the first flexible material.

Clause 8. The method according to anyone of clauses 1 to 7, wherein the process of applying to the back face of the light transparent body a light reflecting element comprises coating the back face with a light reflecting paint.

Clause 9. The method according to anyone of clauses 1 to 7, wherein the process of applying to the back face of the light transparent body a light reflecting element comprises applying a foil to the back face of the light transparent body, the foil having a light reflecting front face and a back face, the front face of the foil lying over the back face of the light transparent body.

Clause 10. The method according to anyone of clauses 1 to 7, wherein the process of applying to the back face of the light transparent body a light reflecting element comprises applying a metal sheet to the back face of the light transparent body, the metal sheet having a light reflecting front face and a back face, the front face of the metal sheet lying over the back face of the light transparent body.

Clause 11. The method according to anyone of clauses 1 to 10, wherein obtaining the light transparent body that has a front face and a back face with there being a channel formed in the front face includes injection molding a polymeric material to form the light transparent body, the channel being formed in front face of the light transparent body during the injection molding.

Clause 12. The method according to anyone of clauses 1 to 11, wherein the light transparent body, light reflecting element, optical diffuser, first liner and second liner are made of flexible materials that results in the apparatus being flexible with an ability to transition between flat and curved configurations to respectively bacterially disinfect a flat surface and a curved surface.

Group F Clauses:

Clause 1. An apparatus for bacterially disinfecting a surface, the apparatus comprising:
  a tube-like body having a length and including an inner face, an outer face and a through opening, the through opening extending along the length of the tube-like body, the tube-like body being made of a material that is transparent to light and having formed in the outer face a channel;
  a radially emitting fiber having a longitudinal axis that is disposed in the channel of the tube-like body, the radially emitting fiber having a length and configured to radially emit a bacterial disinfecting light along a majority of the length of the radially emitting fiber, the radially emitting fiber having an inner side that faces the toward the through opening and an outer side that faces away from the through opening; and a light reflecting element disposed over the outer face of the tube-like surface and the outer side of the radially emitting fiber, the light reflecting element configured to reflect the bacterial disinfecting light emitted from the outer side of the radially emitting fiber in a direction toward the through opening of the tube-like body.

Clause 2. The apparatus according to clause 1, wherein at least one or more portions of the radially emitting fiber has an axial and/or radial freedom of movement inside the channel.

Clause 3. The apparatus according to clause 1, wherein the tube-like body is elastically deformable so that the apparatus is transitional between non-deformed and deformed states, at least one or more portions of the radially emitting fiber having an axial and/or radial freedom of movement inside the channel when the apparatus transitions between the non-deformed and deformed states, the axial and/or radial freedom of movement reducing the amount of tensile stress applied along the length of the radially emitting fiber when the apparatus transitions between the non-deformed and deformed states as compared to an amount of tensile stress that would otherwise be applied to the radially emitting fiber in an absence of the axial and/or radial freedom of movement of the radially emitting fiber inside the channel.

Clause 4. The apparatus according to clause 2, wherein the radially emitting fiber has a proximal end and a distal end and the channel has a proximal end and a distal end, the distal end of the radially emitting fiber being spaced a distance from the distal end of the channel.

Clause 5. The apparatus according to clause 3, wherein the radially emitting fiber has a proximal end and a distal end and the channel has a proximal end and a distal end, the distal end of the radially emitting fiber being spaced a distance from the distal end of the channel.

Clause 6. The apparatus according to clause 2, wherein the proximal end of the radially emitting fiber is fixed relative to the tube-like body and the distal end of the radially emitting fiber is not fixed to the tube-like body.

Clause 7. The apparatus according to clause 3, wherein the proximal end of the radially emitting fiber is fixed relative to the tube-like body and the distal end of the radially emitting fiber is not fixed to the tube-like body.

Clause 8. The apparatus according to clause 2, wherein the distance between the distal end of the radially emitting fiber and the distal end of the channel changes when the tube-like body transitions between the non-deformed and deformed states.

Clause 9. The apparatus according to clause 3, wherein the distance between the distal end of the radially emitting fiber and the distal end of the channel changes when the tube-like body transitions between the non-deformed and deformed states.

Clause 10. The apparatus according to clause 1, wherein the radially emitting fiber has an outer diameter and a corresponding cross-sectional area and the channel has a cross-sectional area, the cross-sectional area of the radially emitting fiber being less that the cross-sectional area of the channel.

Clause 11. The apparatus according to clause 1, wherein the channel includes one or more straight sections and one or more curved sections, the one or more straight sections having a first cross-sectional area and the one or more curved sections having a second cross-sectional area that is greater than the first cross-sectional area.

Clause 12. The apparatus according to clause 1, wherein the channel includes at least one straight section and at least one curved section, the curved section being defined by one or more walls, at least a portion of the radially emitting fiber residing in the curved section being spaced apart from the one or more walls.

Clause 13. The apparatus according to clause 1, wherein the radially emitting fiber has a minimum bending radius, the tube-like body being sufficiently rigid to prevent a deformation of the tube-like body that would result in a bending of the radially emitting fiber beyond the minimum bending radius.

Clause 14. The apparatus according to clause 1, wherein the radially emitting fiber has a minimum bending radius, the apparatus being sufficiently rigid to prevent a bending of the radially emitting fiber beyond the minimum bending radius.

Clause 15. The apparatus according to clause 1, wherein the light reflecting element is a metallic foil.

Clause 16. The apparatus according to clause 1, wherein the light reflecting element is a metal sheet.

Clause 17. The apparatus according to clause 1, wherein the tube-like body, radially emitting fiber and light reflecting element comprise a subassembly, the apparatus further comprising a light transparent liner that envelopes the subassembly.

Clause 18. The apparatus according to clause 1, wherein the light reflecting element comprises a back face and a front face opposite the back face that faces the outer face of the tube-like body, the apparatus further comprising a liner that lies over the back face of the light reflecting element.

Clause 19. The apparatus according to clause 1, further comprising an optical diffuser having a front face and an opposite back face that lies over the front face of the tube-like body.

Clause 20. The apparatus according to clause 19, further comprising a light transparent liner that lies over the front face of the optical diffuser and the back face of the light reflecting element.

Clause 21. The apparatus according to clause 1, wherein the radially emitting fiber has a diameter dimension, the channel has a bottom surface, the bottom surface of the channel and the front face of the tube-line body being separated by a wall having a thickness dimension that is greater than the diameter dimension of the radially emitting fiber.

Clause 22. The apparatus according to clause 1, wherein the radially emitting fiber has a diameter dimension, the channel has a bottom surface, the bottom surface of the channel and the front face of the tube-like body being separated by a wall having a thickness dimension that is greater than 2 times the diameter dimension of the radially emitting fiber.

Clause 23. The apparatus according to clause 1, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 24. The apparatus according to clause 23, wherein the elongate tubular member is fixed inside the channel.

Clause 25. The apparatus according to clause 24, wherein the elongate tubular member is fixed inside the channel by use of a light transparent adhesive.

Clause 26. The apparatus according to clause 1, wherein the tube-like body has a C-shaped cross-section.

Clause 27. The apparatus according to clause 1, wherein the tube-like body has a circular-shaped cross-section.

Clause 28. The apparatus according to clause 1, wherein the tube-like body has a semicircular-shaped cross-section.

Clause 29. The apparatus according to clause 1, wherein the tube-like body has a rectangular-shaped cross-section.

Clause 30. The apparatus according to clause 1, wherein the tube-like body has a semi-rectangular-shaped cross-section.

Group G Clauses:

Clause 1. An apparatus for bacterially disinfecting a surface, the apparatus comprising:
- a light transparent tube-like body having a length and including an outer surface, an inner surface and a through opening, the through opening extending along the length of the tube-like body and being bound by the inner surface;
- a side firing fiber disposed adjacent a first part of the outer surface of the tube-like body, the side firing fiber having a longitudinal axis and an angled end face that is oriented to totally internally reflect a bacterially disinfecting light beam out of a side surface of the side firing fiber in a direction transverse to the longitudinal axis in a direction toward the through opening of the tube-like body.

Clause 2. The apparatus according to clause 1, wherein the through opening has a central axis, the side firing fiber being oriented to totally internally reflect a bacterially disinfecting light beam out of a side surface of the side firing fiber in a direction transverse to the longitudinal axis in a direction toward the central axis of the through opening.

Clause 3. The apparatus according to clause 1 including a plurality of side firing fibers that each has a longitudinal axis and an angled end face that is oriented to totally internally reflect a bacterially disinfecting light beam out of a side surface of the side firing fiber in a direction transverse to the longitudinal axis in a direction toward the through opening of the tube-like body, each of the side firing fibers being located adjacent different parts of the outer surface of the tube-like body than of the other side firing fibers.

Clause 4. The apparatus according to clause 3, wherein the through opening of the tube-like body has a central axis and each of the plurality side firing fibers being configured to emit a bacterial disinfecting light beam directed toward the central axis of through opening.

Clause 5. The apparatus according to clause 3, wherein the plurality of side firing fibers are disposed equidistantly about the outer surface of the tube-like body.

Clause 6. The apparatus according to clause 1, wherein the side firing fiber resides in an air-filled cavity.

Clause 7. The apparatus according to clause 3, wherein each of the side firing fibers resides in an air-filled cavity.

Clause 8. The apparatus according to clause 1, further comprising an end emitting fiber that is configured to end emit a bacterial disinfecting light beam from a distal end of the end emitting fiber, the distal end of the end emitting fiber abutting a second part of the surface of the tube-like body and oriented to direct the bacterial disinfecting light beam in a direction toward the through opening of the tube-like body.

Clause 9. The apparatus according to clause 1, further comprising an end emitting fiber that is configured to end emit a bacterial disinfecting beam from a distal end of the end emitting fiber, the distal end of the end emitting fiber being attached to a second part of the outer surface of the tube-like body by use of an index matching adhesive and oriented to direct the bacterial disinfecting light beam in a direction toward the through opening of the tube-like body.

Clause 10. The apparatus according to clause 9, wherein the end emitting fiber has a core having a first index of refraction and the tube-like body is composed of a material that has a second index of refraction, the index matching adhesive have an index of refraction that is greater than or equal to the first index of refraction and less than or equal to the second index of refraction.

Clause 11. The apparatus according to clause 1, wherein the through opening of the tube-like body includes a central axis, the apparatus further comprising an end emitting fiber that is configured to end emit a bacterial disinfecting light beam from a distal end of the end emitting fiber, the distal end of the end emitting fiber abutting a second part of the surface of the tube-like body and oriented to direct the bacterial disinfecting light beam in a direction toward the central axis of the through opening of the tube-like body.

Clause 12. The apparatus according to clause 1, wherein the through opening of the tube-like body includes a central axis, the apparatus further comprising an end emitting fiber that is configured to end emit a bacterial disinfecting beam from a distal end of the end emitting fiber, the distal end of the end emitting fiber being attached to a second part of the outer surface of the tube-like body by use of an index matching adhesive and oriented to direct the bacterial disinfecting light beam in a direction toward the central axis of the through opening of the tube-like body.

Clause 13. The apparatus according to clause 3, further comprising an end emitting fiber that is configured to end emit a bacterial disinfecting beam from a distal end of the end emitting fiber, the distal end of the end emitting fiber abutting a portion of the outer surface of the tube-like body and oriented to direct the bacterial disinfecting light beam in a direction toward the through opening of the tube-like body.

Clause 14. The apparatus according to clause 3, further comprising an end emitting fiber that is configured to end emit a bacterial disinfecting beam from a distal end of the end emitting fiber, the distal end of the end emitting fiber being attached to a portion of the outer surface of the tube-like body by use of an index matching adhesive and oriented to direct the bacterial disinfecting light beam in a direction toward the through opening of the tube-like body.

Clause 15. The apparatus according to clause 3 wherein the different parts of the outer surface of the tube-like body are each arranged at different circumferential locations of the exterior surface, the plurality of side firing fibers being respectively disposed adjacent the plurality of planar surfaces.

Clause 16. An apparatus for bacterially disinfecting a surface, the apparatus comprising:
- a light transparent tube-like body having a length and including an outer surface, an inner surface and a through opening, the through opening extending along the length of the tube-like body and being bound by the inner surface, the outer surface comprising a plurality of sides located at different circumferential locations;
- a plurality of side firing fibers respectively disposed adjacent the plurality of sides of the outer surface of the tube-like body, each of the side firing fibers having a longitudinal axis and an angled end face that is oriented to totally internally reflect a bacterially disinfecting light beam out of a side surface of the side firing fiber in a direction transverse to the longitudinal axis in a direction toward the through opening of the tube-like body.

Clause 17. The apparatus according to clause 16, wherein the outer surface comprises at least two sides and at least two side firing fibers.

Clause 18. The apparatus according to clause 16, wherein the outer surface comprises at least three sides and at least three side firing fibers.

Clause 19. The apparatus according to clause 16, wherein the outer surface comprises at least three sides and at least three side firing fibers.

Clause 20. The apparatus according to clause 16, wherein the outer surface comprises at least four sides and at least four side firing fibers.

Group H Clauses:

Clause 1. An endotracheal tube support assembly comprising:
- a headband configured for placement around the head of a patient;
- a bite block supported on the headband, the bite block being configured to support at least a portion of an intubation tube;
- a lip guard supported on the headband, the lip guard comprising:
- a flexible body made of a material that is transparent to light and having formed therein a channel, the flexible body having an as-manufactured state and a flexed state that occurs when the flexible body is bent away from its as-manufactured state;
- a radially emitting fiber having a length and configured to radially emit bacterial disinfecting light, the radially emitting fiber having a longitudinal axis that is disposed in the channel, at least a portion of the radially emitting fiber having an axial and/or radial freedom of movement inside the channel when the flexible body transitions between the as-manufactured state and the flexed state, the axial and or radial freedom of movement reducing the amount of tensile stress applied along the length of the radially emitting fiber when the flexible body is bent as compared to an amount of tensile stress that would otherwise be applied to the radially emitting fiber in an absence of the axial and/or radial freedom of movement of the radially emitting fiber inside the channel.

Clause 2. The endotracheal tube support assembly according to clause 1, wherein the radially emitting fiber has a proximal end and a distal end and the channel has an end wall, the distal end of the radially emitting fiber being spaced a distance from the end wall of the channel.

Clause 3. The endotracheal tube support assembly according to clause 2, wherein the proximal end of the radially emitting fiber is fixed relative to the flexible body and the distal end of the radially emitting fiber is not fixed to the flexible body.

Clause 4. The endotracheal tube support assembly according to clause 2, wherein the distance between the distal end of the radially emitting fiber and the end wall of the channel changes when the flexible body transitions between the as-manufactured and flexed states.

Clause 5. The endotracheal tube support assembly according to clause 1, wherein the radially emitting fiber has an outer diameter and a corresponding cross-sectional area and the channel has a cross-sectional area, the cross-sectional area of the radially emitting fiber being less that the cross-sectional area of the channel.

Clause 6. The endotracheal tube support assembly according to clause 1, wherein the channel includes one or more straight sections and one or more curved sections, the one or more straight sections having a first cross-sectional area and the one or more curved sections having a second cross-sectional area that is greater than the first cross-sectional area.

Clause 7. The endotracheal tube support assembly according to clause 1, wherein the channel includes at least one straight section and at least one curved section, the curved section being defined by one or more walls, at least a portion of the radially emitting fiber residing in the curved section being spaced apart from the one or more walls.

Clause 8. The endotracheal tube support assembly according to clause 1, wherein the channel is located internal to the flexible body.

Clause 9. The endotracheal tube support assembly according to clause 1, wherein the radially emitting fiber has a minimum bending radius, the flexible body being sufficiently rigid to prevent a flexing of the flexible body inside the channel that would result in a bending of the radially emitting fiber beyond the minimum bending radius.

Clause 10. The endotracheal tube support assembly according to clause 1, wherein the radially emitting fiber has a minimum bending radius, the lip guard being sufficiently rigid to prevent a bending of the radially emitting fiber beyond the minimum bending radius.

Clause 11. The endotracheal tube support assembly according to clause 1, wherein the flexible body has a front face and a back face, the channel being formed in the front face, the back face of the flexible body comprising a light reflecting coating that is configured to reflect a bacterial disinfecting light emitted from a backside of the radially emitting fiber in a direction toward the front face of the flexible body.

Clause 12. The endotracheal tube support assembly according to clause 1, wherein the flexible body has a front face and a back face, the channel being formed in the front face, the lip guard further comprising a light reflecting element disposed over the back face of the flexible body, the light reflecting element having a front face that faces the back face of the flexible body and a back face opposite the front face, the front face of the light reflecting element being configured to reflect a bacterial disinfecting light emitted from a backside of the radially emitting fiber in a direction toward the front face of the flexible body.

Clause 13. The endotracheal tube support assembly according to clause 12, wherein the light reflecting element is a metallic foil.

Clause 14. The endotracheal tube support assembly according to clause 12, wherein the light reflecting element is a metal sheet.

Clause 15. The endotracheal tube support assembly according to clause 11, further comprising a flexible liner that is transparent to light, the flexible liner enveloping the flexible body.

Clause 16. The endotracheal tube support assembly according to clause 12, further comprising a flexible liner that lies over the front face of the flexible body and the back face of the light reflecting element, the flexible liner being transparent to light.

Clause 17. The endotracheal tube support assembly according to clause 15, further comprising an optical diffuser disposed between the front face of the flexible body and the flexible liner.

Clause 18. The endotracheal tube support assembly according to clause 16, further comprising an optical diffuser disposed between the front face of the flexible body and the flexible liner.

Clause 19. The endotracheal tube support assembly according to clause 1, further comprising an optical diffuser having a front face and a back face, the back face of the optical diffuser being disposed over the front face of the flexible body.

Clause 20. The endotracheal tube support assembly according to clause 19, further comprising a liner that lies over the front face of the optical diffuser and the back face of the flexible body.

Clause 21. The endotracheal tube support assembly according to clause 20, further comprising a light reflecting coating or light reflecting element that is disposed between the back face of the flexible body and the liner.

Clause 22. The endotracheal tube support assembly according to clause 11, wherein the radially emitting fiber has a diameter dimension, the channel has a bottom surface, the bottom surface of the channel and the back face of the flexible body being separated by a wall having a thickness dimension that is greater than the diameter dimension of the radially emitting fiber.

Clause 23. The endotracheal tube support assembly according to clause 12, wherein the radially emitting fiber has a diameter dimension, the channel has a bottom surface, the bottom surface of the channel and the front face of the light reflecting element being separated by a distance that is greater than or equal to the diameter dimension of the radially emitting fiber.

Clause 24. The endotracheal tube support assembly according to clause 11, wherein the radially emitting fiber has a diameter dimension, the channel has a bottom surface, the bottom surface of the channel and the back face of the flexible body being separated by a wall having a thickness dimension that is greater than 2 to 5 times the diameter dimension of the radially emitting fiber.

Clause 25. The endotracheal tube support assembly according to clause 12, wherein the radially emitting fiber has a diameter dimension, the channel has a bottom surface, the bottom surface of the channel and the front face of the light reflecting element being separated by a distance that is greater than 2 to 5 times the diameter dimension of the radially emitting fiber.

Clause 26. The endotracheal tube support assembly according to clause 1, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 27. The endotracheal tube support assembly according to clause 26, wherein the elongate tubular member is fixed inside the channel.

Clause 28. The endotracheal tube support assembly according to clause 27, wherein the elongate tubular member is fixed inside the channel by use of a light transparent adhesive.

Clause 29. The endotracheal tube support assembly according to clause 25, wherein the elongate tubular member is flexible.

Clause 30. The endotracheal tube support assembly according to clause 25, wherein the elongate tubular member has a length that is greater than the length of the radially emitting fiber.

Clause 31. The endotracheal tube support assembly according to clause 1, wherein the flexible body comprises a through opening configured to receive therein the bite block.

Clause 32. The endotracheal tube support assembly according to clause 1, wherein the bite block comprises:
  a tube-like body having a length and including an inner face, an outer face and a through opening, the through opening extending along the length of the tube-like body, the tube-like body being made of a material that is transparent to light and having formed in the outer face a channel;
  a radially emitting fiber having a longitudinal axis that is disposed in the channel of the tube-like body, the radially emitting fiber having a length and configured to radially emit a bacterial disinfecting light along a majority of the length of the radially emitting fiber, the radially emitting fiber having an inner side that faces the toward the through opening and an outer side that faces away from the through opening; and
  a light reflecting element disposed over the outer face of the tube-like surface and the outer side of the radially emitting fiber, the light reflecting element configured to reflect the bacterial disinfecting light emitted from the outer side of the radially emitting fiber in a direction toward the through opening of the tube-like body.

Clause 33. The endotracheal tube support assembly according to clause 32, wherein at least one or more portions of the radially emitting fiber has an axial and/or radial freedom of movement inside the channel.

Clause 34. The endotracheal tube support assembly according to clause 32, wherein the tube-like body is elastically deformable so that the bite block is transitional between non-deformed and deformed states, at least one or more portions of the radially emitting fiber having an axial and/or radial freedom of movement inside the channel when the bite block transitions between the non-deformed and deformed states, the axial and/or radial freedom of movement reducing the amount of tensile stress applied along the length of the radially emitting fiber when the bite block transitions between the non-deformed and deformed states as compared to an amount of tensile stress that would otherwise be applied to the radially emitting fiber in an absence of the axial and/or radial freedom of movement of the radially emitting fiber inside the channel.

Clause 35. The endotracheal tube support assembly according to clause 33, wherein the radially emitting fiber has a proximal end and a distal end and the channel has a proximal end and a distal end, the distal end of the radially emitting fiber being spaced a distance from the distal end of the channel.

Clause 36. The endotracheal tube support assembly according to clause 34, wherein the radially emitting fiber has a proximal end and a distal end and the channel has a proximal end and a distal end, the distal end of the radially emitting fiber being spaced a distance from the distal end of the channel.

Clause 37. The endotracheal tube support assembly according to clause 33, wherein the proximal end of the radially emitting fiber is fixed relative to the tube-like body and the distal end of the radially emitting fiber is not fixed to the tube-like body.

Clause 38. The endotracheal tube support assembly according to clause 34, wherein the proximal end of the radially emitting fiber is fixed relative to the tube-like body and the distal end of the radially emitting fiber is not fixed to the tube-like body.

Clause 39. The endotracheal tube support assembly according to clause 33, wherein the distance between the distal end of the radially emitting fiber and the distal end of the channel changes when the tube-like body transitions between the non-deformed and deformed states.

Clause 40. The endotracheal tube support assembly according to clause 34, wherein the distance between the distal end of the radially emitting fiber and the distal end of the channel changes when the tube-like body transitions between the non-deformed and deformed states.

Clause 41. The endotracheal tube support assembly according to clause 32, wherein the radially emitting fiber has an outer diameter and a corresponding cross-sectional area and the channel has a cross-sectional area, the cross-sectional area of the radially emitting fiber being less that the cross-sectional area of the channel.

Clause 42. The endotracheal tube support assembly according to clause 32, wherein the channel includes one or more straight sections and one or more curved sections, the one or more straight sections having a first cross-sectional area and the one or more curved sections having a second cross-sectional area that is greater than the first cross-sectional area.

Clause 43. The endotracheal tube support assembly according to clause 32, wherein the channel includes at least one straight section and at least one curved section, the curved section being defined by one or more walls, at least a portion of the radially emitting fiber residing in the curved section being spaced apart from the one or more walls.

Clause 44. The endotracheal tube support assembly according to clause 32, wherein the radially emitting fiber has a minimum bending radius, the tube-like body being sufficiently rigid to prevent a deformation of the tube-like body that would result in a bending of the radially emitting fiber beyond the minimum bending radius.

Clause 45. The endotracheal tube support assembly according to clause 32, wherein the radially emitting fiber has a minimum bending radius, the bite block being sufficiently rigid to prevent a bending of the radially emitting fiber beyond the minimum bending radius.

Clause 46. The endotracheal tube support assembly according to clause 32, wherein the light reflecting element is a metallic foil.

Clause 47. The endotracheal tube support assembly according to clause 32, wherein the light reflecting element is a metal sheet.

Clause 48. The endotracheal tube support assembly according to clause 32, wherein the tube-like body, radially emitting fiber and light reflecting element comprise a subassembly, the bite block further comprising a light transparent liner that envelopes the subassembly.

Clause 49. The endotracheal tube support assembly according to clause 32, wherein the light reflecting element comprises a back face and a front face opposite the back face that faces the outer face of the tube-like body, the bite block further comprising a liner that lies over the back face of the light reflecting element.

Clause 50. The endotracheal tube support assembly according to clause 32, further comprising an optical diffuser having a front face and an opposite back face that lies over the front face of the tube-like body.

Clause 51. The endotracheal tube support assembly according to clause 50, further comprising a light transparent liner that lies over the front face of the optical diffuser and the back face of the light reflecting element.

Clause 52. The endotracheal tube support assembly according to clause 32, wherein the radially emitting fiber has a diameter dimension, the channel has a bottom surface, the bottom surface of the channel and the front face of the tube-line body being separated by a wall having a thickness dimension that is greater than the diameter dimension of the radially emitting fiber.

Clause 53. The endotracheal tube support assembly according to clause 32, wherein the radially emitting fiber has a diameter dimension, the channel has a bottom surface, the bottom surface of the channel and the front face of the tube-like body being separated by a wall having a thickness dimension that is greater than 2 times the diameter dimension of the radially emitting fiber.

Clause 54. The endotracheal tube support assembly according to clause 32, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 55. The endotracheal tube support assembly according to clause 54, wherein the elongate tubular member is fixed inside the channel.

Clause 56. The endotracheal tube support assembly according to clause 55, wherein the elongate tubular member is fixed inside the channel by use of a light transparent adhesive.

Clause 57. The endotracheal tube support assembly according to clause 32, wherein the tube-like body has a C-shaped cross-section.

Clause 58. The endotracheal tube support assembly according to clause 32, wherein the tube-like body has a circular-shaped cross-section.

Clause 59. The endotracheal tube support assembly according to clause 32, wherein the tube-like body has a semicircular-shaped cross-section.

Clause 60. The endotracheal tube support assembly according to clause 32, wherein the tube-like body has a rectangular-shaped cross-section.

Clause 61. The endotracheal tube support assembly according to clause 32, wherein the tube-like body has a semi-rectangular-shaped cross-section.

Clause 62. The endotracheal tube support assembly according to clause 1, wherein the lip guard comprises a though opening through which the bite block passes.

Group I Clauses:

Clause 1. An endotracheal tube support assembly comprising:
- a headband configured for placement around the head of a patient;
- a bite block supported on the headband, the bite block being configured to support at least a portion of an intubation tube, the bite block comprising:
- a tube-like body having a length and including an inner face, an outer face and a through opening, the through opening extending along the length of the tube-like body, the tube-like body being made of a material that is transparent to light and having formed in the outer face a channel;
- a radially emitting fiber having a longitudinal axis that is disposed in the channel of the tube-like body, the radially emitting fiber having a length and configured to radially emit a bacterial disinfecting light along a majority of the length of the radially emitting fiber, the radially emitting fiber having an inner side that faces the toward the through opening and an outer side that faces away from the through opening; and a light reflecting element disposed over the outer face of the tube-like surface and the outer side of the radially emitting fiber, the light reflecting element configured to reflect the bacterial disinfecting light emitted from the outer side of the radially emitting fiber in a direction towards the through opening of the tube-like body.

Clause 2. The endotracheal tube support assembly according to clause 1, wherein at least one or more portions of the radially emitting fiber has an axial and/or radial freedom of movement inside the channel.

Clause 3. The endotracheal tube support assembly according to clause 1, wherein the tube-like body is elastically deformable so that the bite block is transitional between non-deformed and deformed states, at least one or more portions of the radially emitting fiber having an axial and/or radial freedom of movement inside the channel when the bite block transitions between the non-deformed and deformed states, the axial and/or radial freedom of movement reducing the amount of tensile stress applied along the length of the radially emitting fiber when the bite block transitions between the non-deformed and deformed states as compared to an amount of tensile stress that would otherwise be applied to the radially emitting fiber in an absence of the axial and/or radial freedom of movement of the radially emitting fiber inside the channel.

Clause 4. The endotracheal tube support assembly according to clause 2, wherein the radially emitting fiber has a proximal end and a distal end and the channel has a proximal end and a distal end, the distal end of the radially emitting fiber being spaced a distance from the distal end of the channel.

Clause 5. The endotracheal tube support assembly according to clause 3, wherein the radially emitting fiber has a proximal end and a distal end and the channel has a proximal end and a distal end, the distal end of the radially emitting fiber being spaced a distance from the distal end of the channel.

Clause 6. The endotracheal tube support assembly according to clause 2, wherein the proximal end of the radially emitting fiber is fixed relative to the tube-like body and the distal end of the radially emitting fiber is not fixed to the tube-like body.

Clause 7. The endotracheal tube support assembly according to clause 3, wherein the proximal end of the radially emitting fiber is fixed relative to the tube-like body and the distal end of the radially emitting fiber is not fixed to the tube-like body.

Clause 8. The endotracheal tube support assembly according to clause 2, wherein the distance between the distal end of the radially emitting fiber and the distal end of the channel changes when the tube-like body transitions between the non-deformed and deformed states.

Clause 9. The endotracheal tube support assembly according to clause 3, wherein the distance between the distal end of the radially emitting fiber and the distal end of the channel changes when the tube-like body transitions between the non-deformed and deformed states.

Clause 10. The endotracheal tube support assembly according to clause 1, wherein the radially emitting fiber has an outer diameter and a corresponding cross-sectional area and the channel has a cross-sectional area, the cross-sectional area of the radially emitting fiber being less that the cross-sectional area of the channel.

Clause 11. The endotracheal tube support assembly according to clause 1, wherein the channel includes one or more straight sections and one or more curved sections, the one or more straight sections having a first cross-sectional area and the one or more curved sections having a second cross-sectional area that is greater than the first cross-sectional area.

Clause 12. The endotracheal tube support assembly according to clause 1, wherein the channel includes at least one straight section and at least one curved section, the curved section being defined by one or more walls, at least a portion of the radially emitting fiber residing in the curved section being spaced apart from the one or more walls.

Clause 13. The endotracheal tube support assembly according to clause 1, wherein the radially emitting fiber has a minimum bending radius, the tube-like body being sufficiently rigid to prevent a deformation of the tube-like body that would result in a bending of the radially emitting fiber beyond the minimum bending radius.

Clause 14. The endotracheal tube support assembly according to clause 1, wherein the radially emitting fiber has a minimum bending radius, the bite block being sufficiently rigid to prevent a bending of the radially emitting fiber beyond the minimum bending radius.

Clause 15. The endotracheal tube support assembly according to clause 1, wherein the light reflecting element is a metallic foil.

Clause 16. The endotracheal tube support assembly according to clause 1, wherein the light reflecting element is a metal sheet.

Clause 17. The endotracheal tube support assembly according to clause 1, wherein the tube-like body, radially emitting fiber and light reflecting element comprise a subassembly, the bite block further comprising a light transparent liner that envelopes the subassembly.

Clause 18. The endotracheal tube support assembly according to clause 1, wherein the light reflecting element comprises a back face and a front face opposite the back face that faces the outer face of the tube-like body, the bite block further comprising a liner that lies over the back face of the light reflecting element.

Clause 19. The endotracheal tube support assembly according to clause 1, further comprising an optical diffuser having a front face and an opposite back face that lies over the front face of the tube-like body.

Clause 20. The endotracheal tube support assembly according to clause 19, further comprising a light transparent liner that lies over the front face of the optical diffuser and the back face of the light reflecting element.

Clause 21. The endotracheal tube support assembly according to clause 1, wherein the radially emitting fiber has a diameter dimension, the channel has a bottom surface, the bottom surface of the channel and the front face of the tube-line body being separated by a wall having a thickness dimension that is greater than the diameter dimension of the radially emitting fiber.

Clause 22. The endotracheal tube support assembly according to clause 1, wherein the radially emitting fiber has a diameter dimension, the channel has a bottom surface, the bottom surface of the channel and the front face of the tube-like body being separated by a wall having a thickness dimension that is greater than 2 times the diameter dimension of the radially emitting fiber.

Clause 23. The endotracheal tube support assembly according to clause 1, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 24. The endotracheal tube support assembly according to clause 23, wherein the elongate tubular member is fixed inside the channel.

Clause 25. The endotracheal tube support assembly according to clause 24, wherein the elongate tubular member is fixed inside the channel by use of a light transparent adhesive.

Clause 26. The endotracheal tube support assembly according to clause 1, wherein the tube-like body has a C-shaped cross-section.

Clause 27. The endotracheal tube support assembly according to clause 1, wherein the tube-like body has a circular-shaped cross-section.

Clause 28. The endotracheal tube support assembly according to clause 1, wherein the tube-like body has a semicircular-shaped cross-section.

Clause 29. The endotracheal tube support assembly according to clause 1, wherein the tube-like body has a rectangular-shaped cross-section.

Clause 30. The endotracheal tube support assembly according to clause 1, wherein the tube-like body has a semi-rectangular-shaped cross-section.

Clause 31. The endotracheal tube support assembly according to clause 1, further comprising a lip guard supported on the headband, the lip guard comprising:
- a flexible body made of a material that is transparent to light and having formed therein a channel, the flexible body having an as-manufactured state and a flexed state that occurs when the flexible body is bent away from its as-manufactured state;
- a radially emitting fiber having a length and configured to radially emit bacterial disinfecting light, the radially emitting fiber having a longitudinal axis that is disposed in the channel, at least a portion of the radially emitting fiber having an axial and/or radial freedom of movement inside the channel when the flexible body transitions between the as-manufactured state and the flexed state, the axial and or radial freedom of movement reducing the amount of tensile stress applied along the length of the radially emitting fiber when the flexible body is bent as compared to an amount of tensile stress that would otherwise be applied to the radially emitting fiber in an absence of the axial and/or radial freedom of movement of the radially emitting fiber inside the channel.

Clause 32. The endotracheal tube support assembly according to clause 31, wherein the radially emitting fiber has a proximal end and a distal end and the channel has an end wall, the distal end of the radially emitting fiber being spaced a distance from the end wall of the channel.

Clause 33. The endotracheal tube support assembly according to clause 32, wherein the proximal end of the radially emitting fiber is fixed relative to the flexible body and the distal end of the radially emitting fiber is not fixed to the flexible body.

Clause 34. The endotracheal tube support assembly according to clause 32, wherein the distance between the distal end of the radially emitting fiber and the end wall of the channel changes when the flexible body transitions between the as-manufactured and flexed states.

Clause 35. The endotracheal tube support assembly according to clause 31, wherein the radially emitting fiber has an outer diameter and a corresponding cross-sectional area and the channel has a cross-sectional area, the cross-sectional area of the radially emitting fiber being less that the cross-sectional area of the channel.

Clause 36. The endotracheal tube support assembly according to clause 31, wherein the channel includes one or more straight sections and one or more curved sections, the one or more straight sections having a first cross-sectional area and the one or more curved sections having a second cross-sectional area that is greater than the first cross-sectional area.

Clause 37. The endotracheal tube support assembly according to clause 31, wherein the channel includes at least one straight section and at least one curved section, the curved section being defined by one or more walls, at least a portion of the radially emitting fiber residing in the curved section being spaced apart from the one or more walls.

Clause 38. The endotracheal tube support assembly according to clause 31, wherein the channel is located internal to the flexible body.

Clause 39. The endotracheal tube support assembly according to clause 31, wherein the radially emitting fiber has a minimum bending radius, the flexible body being sufficiently rigid to prevent a flexing of the flexible body inside the channel that would result in a bending of the radially emitting fiber beyond the minimum bending radius.

Clause 40. The endotracheal tube support assembly according to clause 31, wherein the radially emitting fiber has a minimum bending radius, the lip guard being sufficiently rigid to prevent a bending of the radially emitting fiber beyond the minimum bending radius.

Clause 41. The endotracheal tube support assembly according to clause 31, wherein the flexible body has a front face and a back face, the channel being formed in the front face, the back face of the flexible body comprising a light reflecting coating that is configured to reflect a bacterial disinfecting light emitted from a backside of the radially emitting fiber in a direction toward the front face of the flexible body.

Clause 42. The endotracheal tube support assembly according to clause 31, wherein the flexible body has a front face and a back face, the channel being formed in the front face, the lip guard further comprising a light reflecting element disposed over the back face of the flexible body, the light reflecting element having a front face that faces the back face of the flexible body and a back face opposite the front face, the front face of the light reflecting element being configured to reflect a bacterial disinfecting light emitted from a backside of the radially emitting fiber in a direction toward the front face of the flexible body.

Clause 43. The endotracheal tube support assembly according to clause 42, wherein the light reflecting element is a metallic foil.

Clause 44. The endotracheal tube support assembly according to clause 42, wherein the light reflecting element is a metal sheet.

Clause 45. The endotracheal tube support assembly according to clause 41, further comprising a flexible liner that is transparent to light, the flexible liner enveloping the flexible body.

Clause 46. The endotracheal tube support assembly according to clause 42, further comprising a flexible liner that lies over the front face of the flexible body and the back face of the light reflecting element, the flexible liner being transparent to light.

Clause 47. The endotracheal tube support assembly according to clause 45, further comprising an optical diffuser disposed between the front face of the flexible body and the flexible liner.

Clause 48. The endotracheal tube support assembly according to clause 46, further comprising an optical diffuser disposed between the front face of the flexible body and the flexible liner.

Clause 49. The endotracheal tube support assembly according to clause 31, further comprising an optical diffuser having a front face and a back face, the back face of the optical diffuser being disposed over the front face of the flexible body.

Clause 50. The endotracheal tube support assembly according to clause 49, further comprising a liner that lies over the front face of the optical diffuser and the back face of the flexible body.

Clause 51. The endotracheal tube support assembly according to clause 40, further comprising a light reflecting coating or light reflecting element that is disposed between the back face of the flexible body and the liner.

Clause 52. The endotracheal tube support assembly according to clause 41, wherein the radially emitting fiber has a diameter dimension, the channel has a bottom surface, the bottom surface of the channel and the back face of the flexible body being separated by a wall having a thickness dimension that is greater than the diameter dimension of the radially emitting fiber.

Clause 53. The endotracheal tube support assembly according to clause 42, wherein the radially emitting fiber has a diameter dimension, the channel has a bottom surface, the bottom surface of the channel and the front face of the light reflecting element being separated by a distance that is greater than or equal to the diameter dimension of the radially emitting fiber.

Clause 54. The endotracheal tube support assembly according to clause 41, wherein the radially emitting fiber has a diameter dimension, the channel has a bottom surface, the bottom surface of the channel and the back face of the flexible body being separated by a wall having a thickness dimension that is greater than 2 to 5 times the diameter dimension of the radially emitting fiber.

Clause 55. The endotracheal tube support assembly according to clause 32, wherein the radially emitting fiber has a diameter dimension, the channel has a bottom surface, the bottom surface of the channel and the front face of the light reflecting element being separated by a distance that is greater than 2 to 5 times the diameter dimension of the radially emitting fiber.

Clause 56. The endotracheal tube support assembly according to clause 31, further comprising an elongate tubular member in which the radially emitting fiber resides, the elongate tubular member residing in the channel, the radially emitting fiber having a first diameter and the elongate tubular member having a second diameter that is greater than the first diameter, the elongate tubular member being made of a material that is transparent to light.

Clause 57. The endotracheal tube support assembly according to clause 56, wherein the elongate tubular member is fixed inside the channel.

Clause 58. The endotracheal tube support assembly according to clause 57, wherein the elongate tubular member is fixed inside the channel by use of a light transparent adhesive.

Clause 59. The endotracheal tube support assembly according to clause 55, wherein the elongate tubular member is flexible.

Clause 60. The endotracheal tube support assembly according to clause 55, wherein the elongate tubular member has a length that is greater than the length of the radially emitting fiber.

Clause 61. The endotracheal tube support assembly according to clause 31, wherein the flexible body comprises a through opening configured to receive therein the bite block.

Clause 62. The endotracheal tube support assembly according to clause 31, wherein the lip guard comprises a though opening through which the bite block passes.

Group J Clauses:

Clause 1. An endotracheal tube assembly comprising:
an intubation tube having a proximal end and a distal end;
a ventilator tube;
a connector that fluidly connects the proximal end of the intubation tube with the ventilator tube, the connector having a first end and a second end the first end of the connector being coupled with the ventilator tube at a first connection location and the second end of the connector being coupled with the proximal end of the intubation tube at a second connection location; and
a bacterial disinfecting light apparatus disposed about one or both of the first and second connection locations, the bacterial light disinfecting apparatus comprising one or more optical fibers that are configured to emit bacterial disinfecting light toward one or both of the first and second connection locations.

Clause 2. The endotracheal tube assembly according to clause 1, wherein the one or more optical fibers include one or more radially emitting fibers.

Clause 3. The endotracheal tube assembly according to clause 1, wherein the one or more optical fibers include one or more side firing fibers.

Clause 4. The endotracheal tube assembly according to clause 1, wherein the one or more optical fibers include at least one side firing fiber and at least one end emitting fiber.

Clause 5. The endotracheal tube assembly according to clause 1, wherein the bacterial disinfecting light apparatus comprises:
a tube-like body having a length and including an inner face, an outer face and a through opening, the through opening extending along the length of the tube-like body, the tube-like body being made of a material that is transparent to light and having formed in the outer face a channel, at least a portion of the connector residing inside the through opening;
the one or more optical fibers including a radially emitting fiber having a longitudinal axis that is disposed in the channel of the tube-like body, the radially emitting fiber having a length and configured to radially emit a bacterial disinfecting light along a majority of the length of the radially emitting fiber, the radially emitting fiber having an inner side that faces towards the through opening and an outer side that faces away from the through opening; and
a light reflecting element disposed over the outer face of the tube-like surface and the outer side of the radially emitting fiber, the light reflecting element configured to reflect the bacterial disinfecting light emitted from the outer side of the radially emitting fiber in a direction towards the through opening of the tube-like body.

Clause 6. The endotracheal tube assembly according to clause 1, wherein the bacterial disinfecting light apparatus comprises:
a light transparent tube-like body having a length and including an outer surface, an inner surface and a through opening, the through opening extending along the length of the tube-like body and being bound by the inner surface, at least a portion of the connector residing in the through opening;

a side firing fiber disposed adjacent a first part of the outer surface of the tube-like body, the side firing fiber having a longitudinal axis and an angled end face that is oriented to totally internally reflect a bacterially disinfecting light beam out of a side surface of the side firing fiber in a direction transverse to the longitudinal axis in a direction toward the through opening of the tube-like body.

Clause 7. The endotracheal tube assembly according to clause 6, wherein the through opening has a central axis, the side firing fiber being oriented to totally internally reflect a bacterially disinfecting light beam out of a side surface of the side firing fiber in a direction transverse to the longitudinal axis in a direction toward the central axis of the through opening.

Clause 8. The endotracheal tube assembly according to clause 6 including a plurality of side firing fibers that each has a longitudinal axis and an angled end face that is oriented to totally internally reflect a bacterially disinfecting light beam out of a side surface of the side firing fiber in a direction transverse to the longitudinal axis in a direction toward the through opening of the tube-like body, each of the side firing fibers being located adjacent different parts of the outer surface of the tube-like body than of the other side firing fibers.

Clause 9. The endotracheal tube assembly according to clause 8, wherein the through opening of the tube-like body has a central axis and each of the plurality side firing fibers being configured to emit a bacterial disinfecting light beam directed toward the central axis of through opening.

Clause 10. The endotracheal tube assembly according to clause 8, wherein the plurality of side firing fibers are disposed equidistantly about the outer surface of the tube-like body.

Clause 11. The endotracheal tube assembly according to clause 6, wherein the side firing fiber resides in an air-filled cavity.

Clause 12. The endotracheal tube assembly according to clause 8, wherein each of the side firing fibers resides in an air-filled cavity.

Clause 13. The endotracheal tube assembly according to clause 6, further comprising an end emitting fiber that is configured to end emit a bacterial disinfecting light beam from a distal end of the end emitting fiber, the distal end of the end emitting fiber abutting a second part of the surface of the tube-like body and oriented to direct the bacterial disinfecting light beam in a direction toward the through opening of the tube-like body.

Clause 14. The endotracheal tube assembly according to clause 6, further comprising an end emitting fiber that is configured to end emit a bacterial disinfecting beam from a distal end of the end emitting fiber, the distal end of the end emitting fiber being attached to a second part of the outer surface of the tube-like body by use of an index matching adhesive and oriented to direct the bacterial disinfecting light beam in a direction toward the through opening of the tube-like body.

Clause 15. The endotracheal tube assembly according to clause 14, wherein the end emitting fiber has a core having a first index of refraction and the tube-like body is composed of a material that has a second index of refraction, the index matching adhesive have an index of refraction that is greater than or equal to the first index of refraction and less than or equal to the second index of refraction.

Clause 16. The endotracheal tube assembly according to clause 6, wherein the through opening of the tube-like body includes a central axis, the bacterial disinfecting light apparatus further comprising an end emitting fiber that is configured to end emit a bacterial disinfecting light beam from a distal end of the end emitting fiber, the distal end of the end emitting fiber abutting a second part of the surface of the tube-like body and oriented to direct the bacterial disinfecting light beam in a direction toward the central axis of the through opening of the tube-like body.

Clause 17. The endotracheal tube assembly according to clause 6, wherein the through opening of the tube-like body includes a central axis, the bacterial disinfecting light apparatus further comprising an end emitting fiber that is configured to end emit a bacterial disinfecting beam from a distal end of the end emitting fiber, the distal end of the end emitting fiber being attached to a second part of the outer surface of the tube-like body by use of an index matching adhesive and oriented to direct the bacterial disinfecting light beam in a direction toward the central axis of the through opening of the tube-like body.

Clause 18. The endotracheal tube assembly according to clause 8, further comprising an end emitting fiber that is configured to end emit a bacterial disinfecting beam from a distal end of the end emitting fiber, the distal end of the end emitting fiber abutting a portion of the outer surface of the tube-like body and oriented to direct the bacterial disinfecting light beam in a direction toward the through opening of the tube-like body.

Clause 19. The endotracheal tube assembly according to clause 8, further comprising an end emitting fiber that is configured to end emit a bacterial disinfecting beam from a distal end of the end emitting fiber, the distal end of the end emitting fiber being attached to a portion of the outer surface of the tube-like body by use of an index matching adhesive and oriented to direct the bacterial disinfecting light beam in a direction toward the through opening of the tube-like body.

Clause 20. The endotracheal tube assembly according to clause 8 wherein the different parts of the outer surface of the tube-like body are each arranged at different circumferential locations of the exterior surface, the plurality of side firing fibers being respectively disposed adjacent the plurality of planar surfaces.

Clause 21. The endotracheal tube assembly of clause 1, wherein the bacterial disinfecting light apparatus comprises:
a light transparent tube-like body having a length and including an outer surface, an inner surface and a through opening, the through opening extending along the length of the tube-like body and being bound by the inner surface, the outer surface comprising a plurality of sides located at different circumferential locations;
a plurality of side firing fibers respectively disposed adjacent the plurality of sides of the outer surface of the tube-like body, each of the side firing fibers having a longitudinal axis and an angled end face that is oriented to totally internally reflect a bacterially disinfecting light beam out of a side surface of the side firing fiber in a direction transverse to the longitudinal axis in a direction toward the through opening of the tube-like body.

Clause 22. The endotracheal tube assembly according to clause 21, wherein the outer surface comprises at least two sides and at least two side firing fibers.

Clause 23. The endotracheal tube assembly according to clause 21, wherein the outer surface comprises at least three sides and at least three side firing fibers.

Clause 24. The endotracheal tube assembly according to clause 21, wherein the outer surface comprises at least three sides and at least three side firing fibers.

Clause 25. The endotracheal tube assembly according to clause 21, wherein the outer surface comprises at least four sides and at least four side firing fibers.

In the context of the present application the term "axial freedom of movement" refers to an object's ability to move in a direction corresponding to a longitudinal axis of the body inside a channel or other housing in which the object is disposed. The term "radial freedom of movement" refers to an object's ability to move in a direction orthogonal to the longitudinal axis of the body inside a channel or other housing in which the object is disposed.

What is claimed is:

1. An endotracheal tube assembly comprising:
an intubation tube having a proximal end and a distal end;
a ventilator tube;
a connector that fluidly connects the proximal end of the intubation tube with the ventilator tube, the connector having a first end and a second end the first end of the connector being coupled with the ventilator tube at a first connection location and the second end of the connector being coupled with the proximal end of the intubation tube at a second connection location; and
a bacterial disinfecting light apparatus disposed fully or partially around one or both of the first and second connection locations, the bacterial light disinfecting apparatus comprising one or more optical fibers that are configured to emit a bacterial disinfecting light toward one or both of the first and second connection locations, the one or more optical fibers including at least one side firing fiber and at least one end emitting fiber.

2. An endotracheal tube assembly comprising:
an intubation tube having a proximal end and a distal end;
a ventilator tube;
a connector that fluidly connects the proximal end of the intubation tube with the ventilator tube, the connector having a first end and a second end the first end of the connector being coupled with the ventilator tube at a first connection location and the second end of the connector being coupled with the proximal end of the intubation tube at a second connection location; and
a bacterial disinfecting light apparatus disposed fully or partially around one or both of the first and second connection locations, the bacterial light disinfecting apparatus comprising one or more optical fibers that are configured to emit a bacterial disinfecting light toward one or both of the first and second connection locations, the bacterial disinfecting light apparatus including:
a tube-like body having a length and including an inner face, an outer face and a through opening, the through opening extending along the length of the tube-like body, the tube-like body being made of a material that is transparent to light and having formed in the outer face a channel, at least a portion of the connector residing inside the through opening;
the one or more optical fibers including a radially emitting fiber having a longitudinal axis that is disposed in the channel of the tube-like body, the radially emitting fiber having a length and configured to radially emit the bacterial disinfecting light along a majority of the length of the radially emitting fiber, the radially emitting fiber having an inner side that faces towards the through opening and an outer side that faces away from the through opening; and
a light reflecting element disposed over the outer face of the tube-like surface and the outer side of the radially emitting fiber, the light reflecting element configured to reflect the bacterial disinfecting light emitted from the outer side of the radially emitting fiber in a direction towards the through opening of the tube-like body.

3. An endotracheal tube assembly comprising:
an intubation tube having a proximal end and a distal end;
a ventilator tube;
a connector that fluidly connects the proximal end of the intubation tube with the ventilator tube, the connector having a first end and a second end the first end of the connector being coupled with the ventilator tube at a first connection location and the second end of the connector being coupled with the proximal end of the intubation tube at a second connection location; and
a bacterial disinfecting light apparatus disposed fully or partially around one or both of the first and second connection locations, the bacterial light disinfecting apparatus comprising one or more optical fibers that are configured to emit a bacterial disinfecting light toward one or both of the first and second connection locations, the bacterial disinfecting light apparatus comprising:
a light transparent tube-like body having a length and including an outer surface, an inner surface and a through opening, the through opening extending along the length of the tube-like body and being bound by the inner surface, at least a portion of the connector residing in the through opening;
a side firing fiber disposed adjacent a first part of the outer surface of the tube-like body, the side firing fiber having a longitudinal axis and an angled end face that is oriented to totally internally reflect a bacterially disinfecting light beam out of a side surface of the side firing fiber in a direction transverse to the longitudinal axis in a direction toward the through opening of the tube-like body.

4. The endotracheal tube assembly according to claim 3, wherein the through opening has a central axis, the side firing fiber being oriented to totally internally reflect the bacterially disinfecting light beam out of the side surface of the side firing fiber in the direction transverse to the longitudinal axis in a direction toward the central axis of the through opening.

5. The endotracheal tube assembly according to claim 3 including a plurality of side firing fibers that each has a longitudinal axis and an angled end face that is oriented to totally internally reflect a bacterially disinfecting light beam out of a side surface of the side firing fiber in a direction transverse to the longitudinal axis in a direction toward the through opening of the tube-like body, each of the side firing fibers being located adjacent different parts of the outer surface of the tube-like body than of the other side firing fibers.

6. The endotracheal tube assembly according to claim 5, wherein the through opening of the tube-like body has a central axis and each of the plurality of side firing fibers being configured to emit the bacterially disinfecting light beam directed toward the central axis of the through opening.

7. The endotracheal tube assembly according to claim 5, wherein the plurality of side firing fibers are disposed equidistantly about the outer surface of the tube-like body.

8. The endotracheal tube assembly according to claim 5, wherein each of the side firing fibers resides in an air-filled cavity.

9. The endotracheal tube assembly according to claim 5, further comprising an end emitting fiber that is configured to end emit a bacterial disinfecting beam from a distal end of the end emitting fiber, the distal end of the end emitting fiber abutting a portion of the outer surface of the tube-like body and oriented to direct the bacterial disinfecting light beam in a direction toward the through opening of the tube-like body.

10. The endotracheal tube assembly according to claim 5, further comprising an end emitting fiber that is configured to end emit a bacterial disinfecting beam from a distal end of the end emitting fiber, the distal end of the end emitting fiber being attached to a portion of the outer surface of the tube-like body by use of an index matching adhesive and oriented to direct the bacterial disinfecting light beam in a direction toward the through opening of the tube-like body.

11. The endotracheal tube assembly according to claim 5 wherein the different parts of the outer surface of the tube-like body are each arranged at different circumferential locations of an exterior surface, the plurality of side firing fibers being respectively disposed adjacent a plurality of planar surfaces.

12. The endotracheal tube assembly according to claim 3, wherein the side firing fiber resides in an air-filled cavity.

13. The endotracheal tube assembly according to claim 3, further comprising an end emitting fiber that is configured to end emit a bacterial disinfecting light beam from a distal end of the end emitting fiber, the distal end of the end emitting fiber abutting a second part of the surface of the tube-like body and oriented to direct the bacterial disinfecting light beam in a direction toward the through opening of the tube-like body.

14. The endotracheal tube assembly according to claim 3, further comprising an end emitting fiber that is configured to end emit a bacterial disinfecting beam from a distal end of the end emitting fiber, the distal end of the end emitting fiber being attached to a second part of the outer surface of the tube-like body by use of an index matching adhesive and oriented to direct the bacterial disinfecting light beam in a direction toward the through opening of the tube-like body.

15. The endotracheal tube assembly according to claim 14, wherein the end emitting fiber has a core having a first index of refraction and the tube-like body is composed of a material that has a second index of refraction, the index matching adhesive have an index of refraction that is greater than or equal to the first index of refraction and less than or equal to the second index of refraction.

16. The endotracheal tube assembly according to claim 3, wherein the through opening of the tube-like body includes a central axis, the bacterial disinfecting light apparatus further comprising an end emitting fiber that is configured to end emit a bacterial disinfecting light beam from a distal end of the end emitting fiber, the distal end of the end emitting fiber abutting a second part of the surface of the tube-like body and oriented to direct the bacterial disinfecting light beam in a direction toward the central axis of the through opening of the tube-like body.

17. The endotracheal tube assembly according to claim 3, wherein the through opening of the tube-like body includes a central axis, the bacterial disinfecting light apparatus further comprising an end emitting fiber that is configured to end emit a bacterial disinfecting beam from a distal end of the end emitting fiber, the distal end of the end emitting fiber being attached to a second part of the outer surface of the tube-like body by use of an index matching adhesive and oriented to direct the bacterial disinfecting light beam in a direction toward the central axis of the through opening of the tube-like body.

18. An endotracheal tube assembly comprising:
an intubation tube having a proximal end and a distal end;
a ventilator tube;
a connector that fluidly connects the proximal end of the intubation tube with the ventilator tube, the connector having a first end and a second end the first end of the connector being coupled with the ventilator tube at a first connection location and the second end of the connector being coupled with the proximal end of the intubation tube at a second connection location; and
a bacterial disinfecting light apparatus disposed fully or partially around one or both of the first and second connection locations, the bacterial light disinfecting apparatus comprising one or more optical fibers that are configured to emit a bacterial disinfecting light toward one or both of the first and second connection locations, the bacterial disinfecting light apparatus comprising:
a light transparent tube-like body having a length and including an outer surface, an inner surface and a through opening, the through opening extending along the length of the tube-like body and being bound by the inner surface, the outer surface comprising a plurality of sides located at different circumferential locations;
a plurality of side firing fibers respectively disposed adjacent the plurality of sides of the outer surface of the tube-like body, each of the side firing fibers having a longitudinal axis and an angled end face that is oriented to totally internally reflect a bacterially disinfecting light beam out of a side surface of the side firing fiber in a direction transverse to the longitudinal axis in a direction toward the through opening of the tube-like body.

19. The endotracheal tube assembly according to claim 18, wherein the outer surface comprises at least two sides and at least two side firing fibers.

20. The endotracheal tube assembly according to claim 18, wherein the outer surface comprises at least three sides and at least three side firing fibers.

21. The endotracheal tube assembly according to claim 18, wherein the outer surface comprises at least three sides and at least three side firing fibers.

22. The endotracheal tube assembly according to claim 18, wherein the outer surface comprises at least four sides and at least four side firing fibers.

* * * * *